United States Patent
Christiano et al.

(10) Patent No.: US 9,109,204 B2
(45) Date of Patent: Aug. 18, 2015

(54) METHODS FOR COMPACT AGGREGATION OF DERMAL CELLS

(75) Inventors: Angela M. Christiano, Upper Saddle River, NJ (US); Colin A. B. Jahoda, Durham (GB)

(73) Assignees: THE TRUSTEES OF COLUMBIA UNIVERSITY IN THE CITY OF NEW YORK, New York, NY (US); DURHAM UNIVERSITY, Durham (GB)

(*) Notice: Subject to any disclaimer, the term of this patent is extended or adjusted under 35 U.S.C. 154(b) by 1908 days.

(21) Appl. No.: 12/280,661

(22) PCT Filed: Feb. 28, 2007

(86) PCT No.: PCT/US2007/005193
§ 371 (c)(1),
(2), (4) Date: Aug. 16, 2010

(87) PCT Pub. No.: WO2007/100870
PCT Pub. Date: Sep. 7, 2007

(65) Prior Publication Data
US 2010/0303767 A1    Dec. 2, 2010

Related U.S. Application Data

(60) Provisional application No. 60/778,083, filed on Feb. 28, 2006.

(51) Int. Cl.
C12N 5/071 (2010.01)

(52) U.S. Cl.
CPC .......... *C12N 5/0627* (2013.01); *C12N 2501/70* (2013.01); *C12N 2501/905* (2013.01); *C12N 2533/74* (2013.01)

(58) Field of Classification Search
None
See application file for complete search history.

(56) References Cited

U.S. PATENT DOCUMENTS

| | | | |
|---|---|---|---|
| 4,919,664 A | 4/1990 | Oliver et al. | |
| 4,921,475 A | 5/1990 | Sibalis | |
| 5,008,110 A | 4/1991 | Benecke et al. | |
| 5,087,240 A | 2/1992 | Sibalis | |
| 5,088,977 A | 2/1992 | Sibalis | |
| 5,163,899 A | 11/1992 | Sibalis | |
| 5,164,189 A | 11/1992 | Farhadieh et al. | |
| 5,254,346 A | 10/1993 | Tucker et al. | |
| 5,290,561 A | 3/1994 | Farhadieh et al. | |
| 5,332,213 A | 7/1994 | Klose et al. | |
| 5,336,168 A | 8/1994 | Sibalis | |
| 5,352,456 A | 10/1994 | Fallon et al. | |
| 5,407,713 A | 4/1995 | Wilfong et al. | |
| 5,641,670 A | 6/1997 | Treco et al. | |
| 6,159,950 A | 12/2000 | Crystal et al. | |
| 6,884,427 B1 | 4/2005 | Barrows | |
| 2002/0172705 A1* | 11/2002 | Murphy et al. | 424/422 |
| 2003/0119107 A1 | 6/2003 | Dang et al. | |
| 2003/0198646 A1 | 10/2003 | Stenn | |
| 2004/0023356 A1 | 2/2004 | Krumlauf et al. | |
| 2004/0057937 A1 | 3/2004 | Jahoda et al. | |
| 2004/0096432 A1 | 5/2004 | Fleischmann et al. | |
| 2004/0248492 A1 | 12/2004 | Baker | |
| 2005/0014254 A1 | 1/2005 | Kruse | |
| 2005/0054100 A1 | 3/2005 | Rennard et al. | |
| 2005/0214344 A1 | 9/2005 | Barrows et al. | |
| 2005/0233450 A1 | 10/2005 | Goetinck et al. | |
| 2005/0271632 A1 | 12/2005 | Morgan et al. | |
| 2005/0272150 A1 | 12/2005 | Teumer et al. | |
| 2005/0287127 A1* | 12/2005 | Li et al. | 424/93.21 |
| 2006/0039896 A1 | 2/2006 | Kleinsek et al. | |
| 2006/0134074 A1 | 6/2006 | Naughton | |

FOREIGN PATENT DOCUMENTS

| | | |
|---|---|---|
| EP | 0236014 | 9/1987 |
| EP | 1757307 | 2/2007 |
| JP | 11-180878 | 7/1999 |
| JP | 2003-146893 | 5/2003 |
| JP | 2003-146894 | 5/2003 |
| WO | WO-95/17416 | 6/1995 |
| WO | WO-98/47471 | 10/1998 |
| WO | WO-00/45736 | 8/2000 |
| WO | WO-01/32840 | 5/2001 |
| WO | WO-01/74164 | 10/2001 |
| WO | WO-2004/044188 | 5/2004 |
| WO | WO-2005/059119 | 6/2005 |
| WO | WO-2005/097221 | 10/2005 |

OTHER PUBLICATIONS

Csoka et al., FEBS Letters 417 (1997) pp. 307-310.*
Kramer et al., Cellular and Molecular Life Sciences, vol. 63 (2006) pp. 616-626.*
Reynolds AJ, 1989, from Ph.D. Thesis: in vivo and in vitro studies of isolated and interacting dermal and epidermal components of the integument.
Moore, A.G. et al. "Extracellular matrix molecules and follicle morphogenesis in ovine skin," Reprod. Fertil. Dev., 2001, 13, 143-149.
Underhill, C.B. "Hyaluronan Is Inversely Correlated with the Expression of CD44 in the Dermal Condensation of the Embryonic Hair Follicle," The Journal of Investigative Dermatology, vol. 101, No. 6, Dec. 1993.
International Search Report and Written Opinion issued for corresponding International Patent Application No. PCT/US2007/005193.
Higgins et al., "Initial Characterisation of a New Model of Dermal Papilla Cell Culture," Dermatology, vol. 213, pp. 64 (Jun. 2006).
Higgins et al., "Modelling the hair follicle dermal papilla using spheroid cell cultures," Experimental Dermatology, vol. 19, pp. 546-548 (Apr. 2010).

(Continued)

*Primary Examiner* — Allison Fox
*Assistant Examiner* — Yvonne Pyla
(74) *Attorney, Agent, or Firm* — Baker Botts L.L.P.

(57) ABSTRACT

The invention provides for a method for aggregating dermal papilla cells or dermal sheath cells or a combination thereof, the method comprising: growing dermal papilla cells or dermal sheath cells or a combination thereof in suspension culture; and contacting the culture with an effective amount of an enzyme, wherein a substrate of the enzyme is an extracellular matrix molecule in the suspension culture, so as to aggregate dermal papilla cells or dermal sheath cells. The culture may be a hanging drop culture and the enzyme may be a hyaluronidase.

56 Claims, 32 Drawing Sheets

(56) References Cited

OTHER PUBLICATIONS

Ihara et al., "Formation of hair follicles from a single-cell suspension of embryonic rat skin by a teo-step procedure in vitro," Cell and Tissue Research, vol. 266, No. 1, pp. 65-73 (Oct. 1991).

Inamatsu et al., "Establishment of rat dermal papilla cell lines that sustain the potency to induce hair follicles from afollicular skin," the journal of investigative dermatology, vol. 111, pp. 767-775 (Nov. 1998).

Jamie E. Davies, "Cell Migration: Condensation," mechanisms of morphogenesis: The creation of Biological form, pp. 185-196 (Jan. 2005).

Ouji et al., "Wnt-10b secreted from lymphocytes promotes differentiation of skin epithelial cells," Biochemical and biophysical research communications, vol. 342, pp. 1063-1069 (Feb. 2006).

Supplementary European Search Report mailed on Jun. 22, 2010 for European Patent Application No. EP.07751924.

Takeda A. et al., "Histodifferentiation of Hair follicles in grafting of cell aggregates obtained by rotation culture of embryonic rat skin," Scandinavian Journal of Plastic and reconstructive Surgery and hand Surgery, vol. 32, pp. 359-364 (Dec. 1998).

Andl T, et al., "WNT signals are required for the initiation of hair follicle development," Dev Cell, 2(5):pp. 643-653 (2002).

*Animal Cell Culture: A Practical Approach 2nd Ed.*, Rickwood, D. and Hames, B. D., eds. (Oxford University Press: New York, 1992.

Arias AM, et al., "Wnt signalling: pathway or network?," Curr Opin Genet Dev, vol. 9: pp. 447-454 (1999).

Armstrong and Armstrong, "An Instructive role for the Interstitial Matrix in Tissue Patterning Tissue Segregation and Intercellular Invasion," J Cell Biol, vol. 110: pp. 1439-1455 (1990).

Bao S, et al., "Periostin potently promotes metastatic growth of colon cancer by augmenting cell survival via the AKT/PKB pathway," Cancer Cell, vol. 5: pp. 329-339 (Apr. 2004).

Beaudoin GM, et al., "Hairless triggers reactivation of hair growth by promoting Wnt signaling," PNAS, vol. 102(41): pp. 14653-14658 (2005).

Bejsovec A, "Wnt Pathway Activation: New Relations and Locations," Cell, vol. 120(1):11-14 (2005).

Brembeck FH, et al., "Balancing cell adhesion and Wnt signaling the key role of β-catenin," Curr Opin Genet Dev, vol. 16(1): pp. 51-59 (2006).

Brennan KR et al., "Wnt Proteins in mammary Development and Cancer,", J Mammary Gland Biol Neoplasia, 9(2): pp. 119-131 (2004).

Brown et al., "Regulation of hyaluranan binding by F-actin and colocalization of CD44 and phosphorylated ezrin/radixin/moesin (ERM) proteins in myeloid cell," Experimental Cell research, vol. 303, pp. 400-414 (2005).

Bunger et al.,"Deletion of the tissue response against alginate-pll capsules by temporary release of co-encapsulated steroids," Biomaterials, vol. 26:pp. 2353-2360 (2005).

Burkitt HG, et al, Wheater's Functional Histology, $3^{rd}$ Edition, Churchill Livingstone, 1996: Chapter 9.

Burrus LW et al.,"Biochemical Analysis of Murine Wnt Proteins Reveals both shared ans distinct properties,", Exp Cell Res, vol. 220: pp. 363-373 (1995).

Chapter 8 of the Handbook in Practical Animal Cell Biology: Epithelial Cell Culture (Cambridge Univ. Press, Great Britain; 1996).

Charpentier et al., "Plakoglobin Suppresses Epithelial Proliferation and Hair Growth in vivo," The Journal of Cell Biology, vol. 149, pp. 503-519 (Apr. 2000).

Christiansen JH, et al., "Murine Wnt-11 and Wnt-12 have temporally and spatially restected expression petters during embryonic development," Mech Dev, vol. 51(2-3):pp. 341-350 (1995).

Cleveland WL, et al., "Routine large-Scale Production of Monoclonal Antibodies in a Protein-Free Culture Medium," J Immunol Methods, vol. 56(2): pp. 221-234 (1983).

Couchman, "Hair Follicle Proteoglycans," J Invest Dermatol. 101(1 Suppl): pp. 60S-64S (1993).

Csoka et al., "The Six Hyaluronidase-like genes in the human and mouse genomes," Matrix Biology, vol. 20: pp. 499-508 (2001).

Do et al., "Role of CD44 and Hyaluronic Acid (HA) in Activation of Alloreactive and Antigen-Specific T Cells by bone Marrow-Derived Dentritic cells," J. Immunother, vol. 27, pp. 1-12 (2004).

F. M. Ausubel et al., 1989,*Current Protocols in Molecular Biology*, John Wiley & Sons, New York, N.Y.

Fainsod A, et al., "The Dorsalizing and neural inducing gene follistatin is an antagonist of BmP-4," Mech Dev, vol. 63: pp. 39-50 (1997).

Fiers, et al., "Complete nucleotide sequence of SV40 DNA,", Nature 273: pp. 113-120 (1978).

Gamer LW, et al., "A Novel BMP Expressed in Developping Mouse Limb, Spinal Cord, and Tail Bud is a potent Mesoderm Inducer in *Xenopus* Embryos," Dev Biol., vol. 208: pp. 222-232 (1999).

Gavin BJ, et al., "Expression of multiple novel Wnt-1/int-1-related genes during fetal and adult mouse development," Genes Dev, vol. 4(12B):2319-32 (1990).

Goeddel, *Gene Expression Technology: Methods in Enzymology* 185, Academic Press, San.Diego, Calif. (1990).

Gregorieff A et al., "Wnt signaling in the intestinal epithelium: from endoderm to cancer," Genes Dev, vol. 19(8): pp. 877-890 (2005).

Gunthert U et al., "A new Variant of Glycoprotein CD44 confers Metastatic Potential to Rat Carcinoma Cells," Cell, vol. 65, pp. 13-24 (1991).

Guo Q, et al., "Overexpression of mouse Follistatin Causes Reproductive defects in Transgenic Mice", Mol Endocrinol, vol. 12:pp. 96-106 (1997).

Haertel-Wiesmann M, et al., J Biol Chem, Regulation of Cyclooxygenase-2 and Periostin by Wnt-3 in Mouse Mammary Epithelial Cells, vol. 275(41): pp. 32046-32051 (2000).

Hage JJ et al., "Surgical Depilation of the Treatment of Pseudofolliculitis or local Hirsutism of the face: Experience in the First 40 Patients," Plast Reconstr Surg, vol. 88:pp. 446-451 (1991).

Hager GL, et al., Protein dynamics in the nuclear compartment, Curr Opin Genet Dev, vol. 12(2): pp. 137-141 (2002).

Hall et al., "All for one and one for all: condensations and the initiation of skeletal development," Bioessays, vol. 22, pp. 138-147 (2000).

Hardingham et al., "Proteoglycans: many forms and many functions," FASEB J. vol. 6(3): pp. 861-870 (1992).

Hibino et al., "Role of TGF-β2 in the human hair cycle,", J Dermatol Sci, vol. 35(1):pp. 9-18 (2004).

Higashi et al., "A Novel Transfection Method for Mammalian cells using Calcium Alginate Microbeads," J Biosci and Bioeng, vol. 97:pp. 191-195 (2004).

Hoffman, A. S., "Hydrogels for biomedical applications," Adv Drug Deliv Rev. vol. 43: pp. 3-12 (2002).

Hoffman, A. S., "Hydrogels for Biomedical Applications," Ann NY Acad Sci , vol. 944: pp. 62-73 (2001).

Horiuchi K, et al., "Identification and Characterization of a Novel Protein, Periostin, with Restricted Expression to Periosteum and Periodontal ligament and increased Expression by transforming Growth factor β," J Bone Miner Res, vol. 14(7):pp. 1239-1249 (1999).

Iemura S, et al., "Direct binding of follistatin to a complex of bone-morphogenetic protein and its receptor inhibits ventral and epidermal cell fates in early *Xenopus* embryo," PNAS, vol. 95:pp. 9337-9342 (1998).

Inaba M and Y Inaba, *Human Body Odor, Etiology, Treatment and Related Factors*, Springer-Verlag [Tokyo], 1992: Chapter 16.

Itasaki N, et al., "Wise, a context-dependent activator and inhibitor of Wnt signalling," Development, vol. 130:pp. 4295-4305 (2003).

J. Sambrook et al., 1989, *Molecular Cloning, A Laboratory Manual*, Cold Spring Harbor Press, Plainview, N.Y.

Jahoda CA, "Induction of follicle formation and hair growth by vibrissa dermal papillae implanted into rat ear wounds: vibrissa-type fibres are specified," Development, vol. 115: pp. 1103-1109 (1992).

Jahoda CA, et al. "Human Hair Follicle Regeneration Following Amputation and Grafting into the Nude Mouse," J Invest Dermatol, vol. 107:pp. 804-807 (1996).

Jahoda et al., "Hair Follicle dermal sheath cells: unsung participants in wound healing," The Lancet, vol. 358, pp. 1445-1448 (Oct. 2001).

Jahoda et al., "Induction of hair growth by implantation of cultured dermal papilla cells," Nature, vol. 311, pp. 560-562 (Oct. 1984).

(56) References Cited

OTHER PUBLICATIONS

Jahoda et al., "Induction of hair Growth in Ear wounds by cultured Dermal papilla cells," J Invest Dermatol, vol. 101:pp. 584-590 (1993).
Jahoda et al., "The growth of vibrassa dermal papilla cell in vitro," B J Dermatol, vol. 105: pp. 623-627 (1981).
Jahoda, "Cell Movement in the Hair Follicle Dermis—more than a two-way street?," The Journal of investigative dermatology, vol. 121, pp. IX-XI (Dec. 2003).
Johnson ML, et al., "LRP5 and Wnt Signaling: A Union made for Bone," Bone Miner Res, vol. 19(11):pp. 1749-1757 (2004).
Kashiwagi M, et al., "Specification inhibition of hair follicle formation by epidermal growth factor in an organ culture of developping mouse skin," Dev Biol, vol. 189(1):pp. 22-32 (1997).
Kim et al., "Periostin is down-regulated in high grade human bladder cancers and suppresses in vitro cell invasiveness and in vivo metastasis of cancer cells," Int. J. Cancer, vol. 117, pp. 51-58 (2005).
Kishimoto et al., "Wnt signaling maintains the hair-inducing activity of the dermal papilla," Genes & Development, vol. 14, pp. 1181-1185 (2000).
Kruzynska-Frejtag A, et al., "Periostin is Expressed Within the developping teeth at the sites of Epithelial-Mesenchymal Interaction," Dev Dyn,vol. 229:pp. 857-868 (2004).
Kudo et al, "Zebrafish periostin is required for the adhesion of muscle fiber bundles to the myoseptum and for the differentiation of muscle fibers," Development Biology, vol. 267, pp. 473-487 (2004).
Kuhnert F, et al., "Essential requirement for Wnt signaling in proliferation of adult small intestine and colon revealed by adenoviral expression of Dickkopf-1," Proc Natl Acad Sci U S A, vol. 101(1):pp. 266-271 (2004).
Lavker et al., "Hair Follicle stem cells," JID Symposium Proceedings, Vil 8, pp. 28-38 (2003).
Lee et al., "Controlled degradation of hydrogels using multi-functional cross-linking molecules," Biomaterials, vol. 25: pp. 2461-2466 (2004).
Lee FS, et al., "Insertional mutagenesis identified a member of the Wnt gene family as a candidate oncogene in the mammary epithelium of int-2/Fgf-3 transgenic mice," Proc Natl Acad Sci U S A, vol. 92(6):pp. 2268-2272 (1995).
Li et al., "Culture of Neural Stem Cells in Calcium Alginate beads," Biotechnol Prog., vol. 22(6): pp. 1683-1689 (2006).
Li et al., "Reconstruction of Humain hair dermal papilla with microencapsulation in vitro," J Dermatol Sci , vol. 38:pp. 107-109 (2005).
Lichti U, et al., "In vivo regulation of murine hair growth: Insights from grafting defined cell populations onto nude mice," J Invest Dermatol, vol. 101:pp. 124s-129s (1993).
Lindner V, et al., "Vascular injury induces expression of periostin: implication for vascular cell differentiation and migration," Arterioscler Throm Vasc Biol, vol. 25: pp. 77-83 (2005).
Litvin J, et al., "Expression and function of periostin-Isoforms in bone," J Cell Biochem, vol. 92: pp. 1044-1061 (2004).
Litvin J, et al., "Periostin and periostin-like factor in the human heart: possible therapeutic targets," Cardiovas Path, vol. 15: pp. 24-32 (2006).
Litvin J, et al., "Periostin family of proteins: Therapeutic targets for heart disease," Anat Record Part A, vol. 287: pp. 1025-12 (2005).
Logan CY et al., "The Wnt signaling pathway in development and disease," Annu Rev Cell Dev Biol, vol. 20: pp. 781-810 (2004).
Malkinson FD et al., "Hair matrix cell kinetics: a selective review," Int J Dermatol, vol. 17:pp. 536-551 (1978).
Mason JO, et al., "Mutational Analysis of Mouse Wnt-1 identifies two temperature-sensitive alleles and attributes of Wnt-1 protein essential for transformation of a mammary cell line," Mol Biol Cell, vol. 3: pp. 521-533 (1992).
Matzuk MM, et al., "Multiple defects and perinatal death in mice deficient in follistatin," Nature, vol. 374:pp. 360-363 (1995).
Millar et al., Wnt signaling in the control of hair growth and structure, Developmental biology, vol. 207, pp. 133-149 (1999).

Molecular Probes, The Handbook: A Guide to Fluorescent Probes and Labelling Technologies, $10^{th}$ edition (Invitrogen Corp., CA), 2005.
Moon RT, et al., "Wnt and β-Catenin signalling: diseases and therapies," Nat Rev Genet, 5(9):689-699 (2004).
Nakamura M, et al., "Control of pelage hair follicle development and cycling by complex ineractions between follistatin and activin," FASEB J, vol. 17(3):pp. 497-499 (2003).
Nakamura T et al., "Activin-binding Protein from Rat Ovary is Follistatin," Science, vol. 247 (4944), pp. 836-838 (1990).
Nelson WJ and R Nusse,"Convergence of Wnt, β-Catenin, and Cadherin Pathways," Science, vol. 303:1483-7 (2004).
Nusse R, "Relays at the membrane," Nature, vol. 438:pp. 747-749 (2005).
Nusse R, "Wnts and hedgehogs: lipid-modified proteins and similarities in signaling mechanisms at the cell surface," Development, vol. 130(22):5297-305 (2003).
O'Shaughnessy et al., "The Wnt signalling modulator, wise, is expressed in an interaction-Dependent manner during hair-follicle cycling," J Invest Dermatol, vol. 123, pp. 613-621 (2004).
O'Shaughnessy RF, et al., "The role of BMP signalling in the control of ID3 expression in the hair follicle." Experimental Dermatology, vol. 13, pp. 621-629 (2004).
Ohyama M, et al., "Characterization and isolation of stem cell-enriched human hair follicle bulge cells," J Clin Invest, vol. 116(1): pp. 249-260 (2006).
Oliver RF and CA Jahoda, *Biology of Wool and Hair* (eds Roger et al.), 1989, Cambridge University Press:51-67.
Oliver RF, "The dermal papilla and the development and gowth of hair," J Soc Cosmet Chem, vol. 22:pp. 741-755 (1971).
Oliver RF, In the Skin of Vertebrates [Ed. Spearman RIC], London Academy Press, 1980: 199-210.
Oshima A, et al., "A Novel Mechanism for the regulation of Osteoblast differentiation: Transcription of Periostin, a member of the fasciclin I family, is Regulated by the bHIH transcription Factor, Twist," J Cell Biochem, vol. 86: pp. 792-804 (2002).
Papkoff J et al., "Secreted int-1 Protein is associated with the Cell surface," Mol Cell Biol, vol. 10:pp. 2723-2730 (1990).
Patel K, "Follistatin," Intl J Biochem Cell Bio, vol. 30:pp. 1087-1093 (1998).
Peppas et al., "Hydrogels in biology and Medicine: From Molecular Principles to Bionanotechnology," Adv Mater. vol. 18: pp. 1345-1360 (2006).
Reddy et al., "Characterization of Wnt gene expression in developing and postnatal hair follicles and identification of WNT5a as a target of Sonic Hedgehog in hair follicle morphogenesis," Mechanisms of Development, vol. 107, pp. 69-82 (2001).
Rendl et al., "Molecular Dissection of Mesenchymal-Epithelial Interactions in the Hair Follicle," Plos Biology, vol. 3, pp. e331- (2005).
Reya T et al., "Wnt signalling in stem cells and cancer," Nature, vol. 434:pp. 843-850 (2005).
Reynolds AJ et al., "Cultured dermal papilla cells induce follicle formation and hair growth by transdifferentitation of an adult epidermis," Development, vol. 115: pp. 587-593 (1992).
Reynolds AJ et al., "Hair Fibre progenitor cells: developmental status and interactive potential," Sem Devel Biol, vol. 4: pp. 241-250 (1993).
Reynolds AJ et al., "Inductive Properties of Hair Follicle Cells," PNAS, vol. 624:pp. 226-242 (1991).
Reynolds AJ, et al., "Human Hair Follicle Germinative Epidermal Cell culture," J Invest Dermatol, vol. 101:pp. 634-638 (1993).
Reynolds et al., "Trans-gender induction of hair follicles," Nature, vol. 402, pp. 33-34 (Nov. 1999).
Rios H, et al., "Periostin null mice exhibit dwarfism, incisor enamel defects, and an early-Onset Periodontal disease-like Phenotype," Mol Cell Biol, vol. 25(24):pp. 11131-11144 (2005).
Robertson DM, et al., "The isolation of polypeptides with FSH suppressing activity from bovine follicular fluid which are structurally different to inhibin," BBRC, vol. 149: pp. 744-749 (1987).
Roh et al., "Dermal papilla- induced hair differentiation of adult epithelial stem cells from human skin," Physiol Genomics, vol. 19, pp. 207-217 (2004).

(56) References Cited

OTHER PUBLICATIONS

Ross MH, Histology: A text and atlas, 3rd edition, Williams and Wilkins, 1995: Chapter 14.
Rousche et al., "Temporal expression of CD44 during embryonic chick limb development and modulation of its expression with retinoic acid," Matrix Biology, vol. 21, pp. 53-62 (2002).
Santini et al., "Apoptosis, cell adhesion and the extracellular matrix in the three-dimensional growth of multicellular tumor spheroids," Critical reviews in Oncology/Hematology, vol. 36, pp. 75-87 (2000).
Schmidt-Ullrich et al., "Molecular principles of hair follicle induction and morphogenesis," Bioessays, vol. 27, pp. 247-261 (2005).
Shimasaki S, et al., "Follistatin Gene Expression in the Ovary and Extragonadal tissues," Mol Endocrinol, vol. 3(4):pp. 651-659 (1989).
Shimizu H et al., "Wnt Signaling through the β-catenin pathway is Sufficient to maintain, but not restore, anagen-phase characteristics of dermal papilla cells," J Invest Dermatol, vol. 122(2): pp. 239-245 (2004).
Sleeman et al., "Gene Expression in Rat Dermal papilla cells: Analysis of 2529 ESTs," Genomics, vol. 69(2): pp. 214-224 (2000).
Sleeman et al., "Regulated clustering of variant CD44 Proteins increases their hyaluronate binding capacity," The Journal of Cell Biology, vol. 135, pp. 1139-1150 (Nov. 1996).
Song et al., "The role of glypicans in mammalian development," Biochimica et Biophysica Acta, vol. 1573, pp. 241-246 (2002).
Spicer AP, et al., "Investigation of Hyaluronan function in the mouse through targeted mutagenesis," Glycoconj J, vol. 19(4-5):pp. 341-345 (2002).
Spicer et al., "Hyaluronan and Morphogenesis," Birth Defects Research (Part C), vol. 72, pp. 89-108 (2004).
St-Jacques et al., "Sonic hedgehog signaling is essential for hair development," Current biology, vol. 8, pp. 1058-1068 (1998).
Tai IT, et al., "Periostin induction in tumor cell line explants and inhibition of in vitro cell growth by anti-periostin anti-bodies," Carcinogenesis, vol. 26(5): pp. 908-915 (2005).
Takeshita S, et al., "Osteoblat-specific factor 2: cloning of a putative bone adhesion protein with homology with the insect protein fasciclin I," Biochem J, vol. 294: pp. 271-278 (1993).
Termeer et al., "The role of CD44 during CD40 ligand-induced dendritic cell clustering and maturation," Journal of Leukocyte Biology, vol. 70, pp. 715-722 (Nov. 2001).
Tien et al., "Three Vertebrate hyaluronan Synthases are expressed during mouse development in distinct Spatial and temporal patterns," Developmental Dynamics, vol. 233, pp. 130-141 (2005).
Toole et al., Hyaluroan in morphogenesis, Cell & Developmental Biology, vol. 12, pp. 79-87 (2001).
Tuhkanen et al., "CD44 Expression Marks the onset of Keratinocyte startification and mesenchymal maturation into fibrous dermis in fetal human skin," The Journal of Histochemistry & Citochemistry, vol. 47, pp. 1617-1624 (1999).
Tzircotis et al., "Chemotaxis towards hyaluronan is dependent on CD44 expression and modulated by cell type variation in CD44-hyaluronan binding," Journal of Cell Science, vol. 118, pp. 5119-5128 (2005).
Ueno N, et al., "Isolation and partial characterization of follistatin: A single-chain Mr 35,000 monomeric protein that inhibits the release of folliclestimulating hormone," PNAS, vol. 84:pp. 8282-8286 (1987).
Underhill CB, yaluronan Is Inversely Correlated with the Expression of CD44 in the Dermal Condensation of the Embryonic Hair Follicle, J Invest Dermatol, vol. 101(6): pp. 820-826 (1993).
van't Veer LJ, et al., "Molecular Cloning and chromosomal assignment of the Human homolog of int-1, a mouse gene implicated in Mammary tumorigenesis," Mol Cell Biol,, vol. 4:pp. 2532-2534 (1984).
Wainwright BJ, et al., "Isolation of a human gene with protein sequence similarity to human and murine int-1 and the *Drosophila* segment polarity mutant wingless," EMBO J, vol. 7(6):pp. 1743-1748 (1988).
Watson SA, et al., "Sheep vibrissa dermal papillae induce hair follicle formation in heterotypic skin equivalents," Br J Dermatol, vol. 131:pp. 827-835 (1994).
Weber B, et al., "Transient expression of CD44 variant isoforms in the ontogeny of the rat: Ectoderm-, endoderm- and mesoderm-derived cells express different exon combinations," Differentiation, vol. 60(1):pp. 17-29 (1996).
Weimann et al., "Hyaluronan-Independent Adhesion od CD44H and CD44v10+0 lymphocytes to dermal micro vascular endothelial cells and keratinocytes," J. Invest Dermatol, vol. 117, pp. 949-957 (2001).
Weinberg WC, et al., "Reconstruction of hair Follicle development in vivo: Determination of follicle formation, Hair Growth, and hair quality by dermal Cells," J Invest Dermatol, vol. 100: pp. 229-236 (1993).
Wheatley SC, et al., "Restricted expression of the Hyaluronan receptor, CD44, during postimplantation mouse embryogenesis suggests key roles in tissues formation and patterning," Development, vol. 119(2):pp. 295-306 (1993).
Willert K, et al., "Wnt proteins are lipid-modified and can act as stem cell growth factors," Nature, vol. 423:pp. 448-452 (2003).
Yu and Toole, "Common Pattern of CD44 Isoforms is Expressed in Morphogenetically Active Epithelia," Developmental Dynamics, vol. 208: pp. 1-10 (1997).
Zhu et al., "The role of the Hyaluronan Receptor CD44 in MSC Migration in the Extracellular Matrix," Stem Cells Express, published online, 32 pages (Nov. 23, 2005).

\* cited by examiner

No Mg

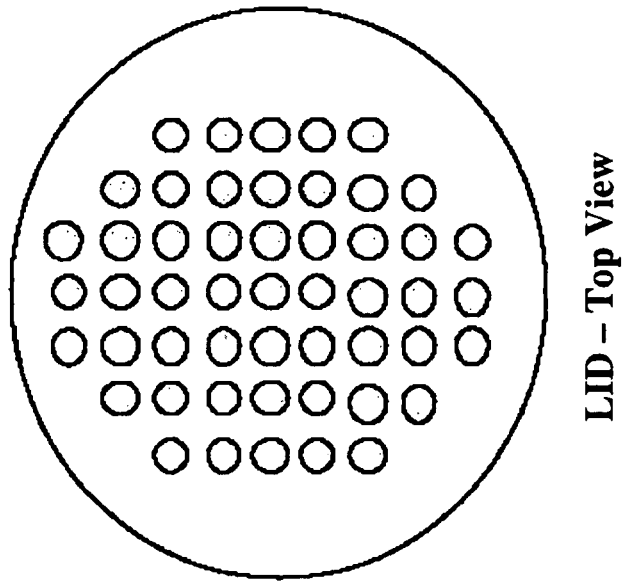
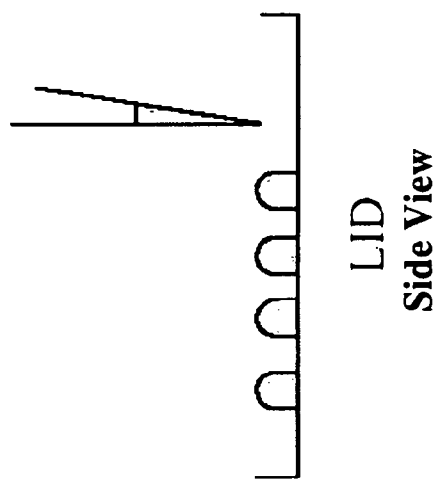
FIG. 4

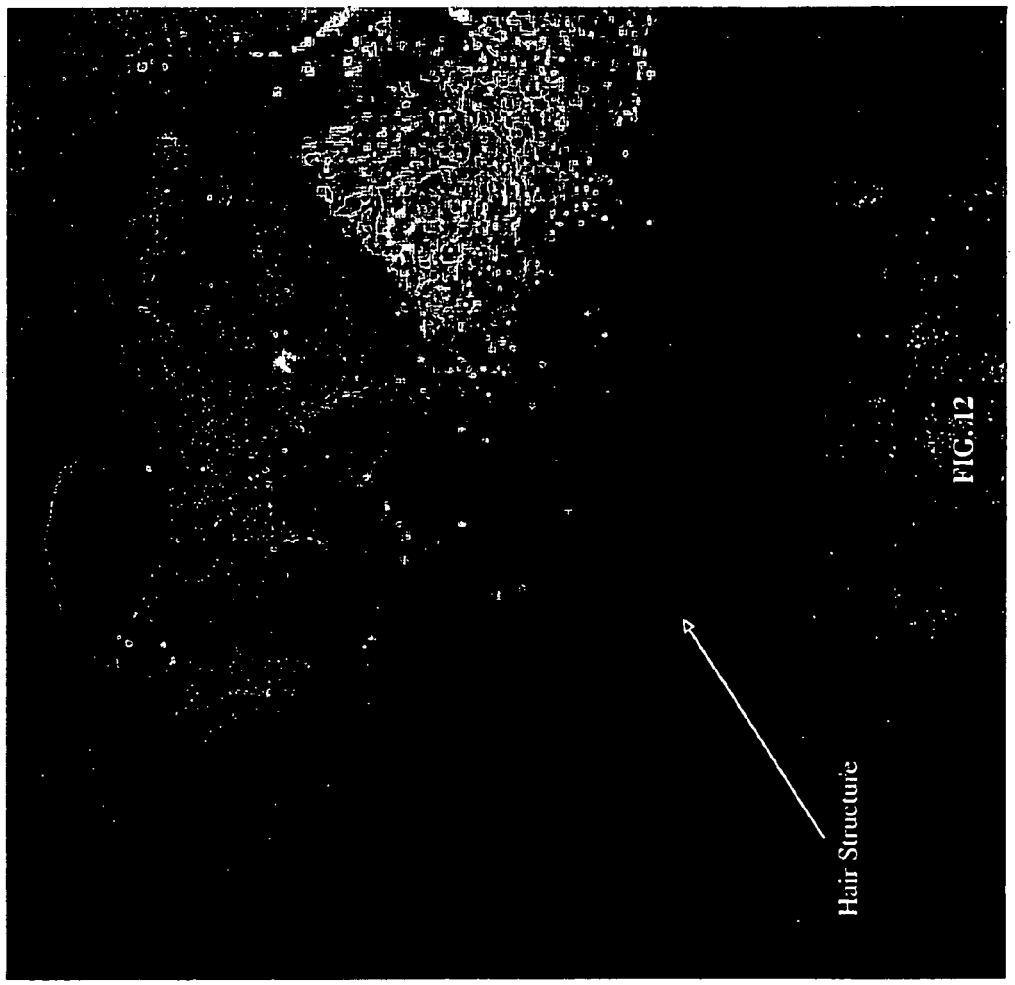

HA
7.5 dpc dorsal
feather placode
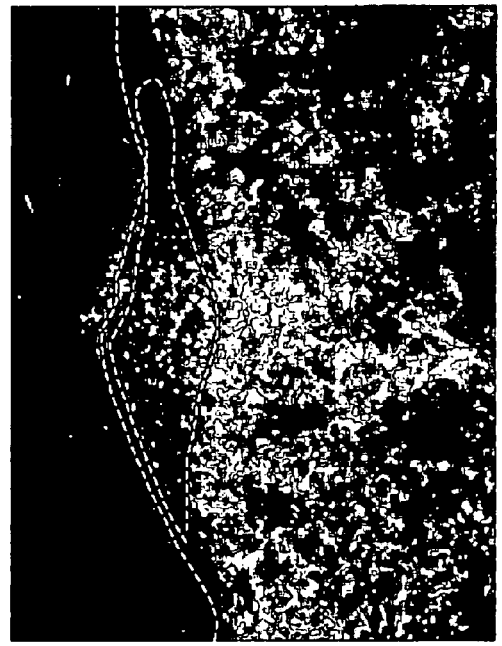
8.5 dpc dorsal
feather placode
FIG. 18

FIG. 24

METHODS FOR COMPACT AGGREGATION OF DERMAL CELLS

This application is a U.S. National Phase Application under 35 U.S.C. §371 of International Patent Application No. PCT/US2007/005193, filed Feb. 28, 2007, which claims priority of U.S. Provisional Patent Application No. 60/778,083, filed Feb. 28, 2006, each of which is incorporated herewith in its entirety.

All patents, patent applications and publications cited herein are hereby incorporated by reference in their entirety. The disclosures of these publications in their entireties are hereby incorporated by reference into this application.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Dermal condensation is crucial for morphogenesis of skin appendages. Although mechanisms for condensation have been elucidated for other systems such as bone, the precise molecular basis for hair follicle dermal condensation are not known. Historical studies have described expression of CD44 and hyaluronan (HA) during early hair follicle morphogenesis. Through microarray analysis, we have uncovered new evidence that this mechanism may play a key role in formation of the dermal condensate. There is increasing evidence from the literature that CD44 acts as a component of developmental signaling pathways as well as functioning as the major receptor for HA.

BRIEF DESCRIPTION OF THE FIGURES

FIG. 4 is a schematic representation for generating hanging drops on a lid of a Petri dish.

FIG. 11 represents microscopy images of a sectioned follicle.

FIG. 12 is a photographic image depicting hair induction following implantation of a rat hair follicle containing dermal papilla cells. The white arrow points to a hair structure.

FIG. 18 represents immunofluorescent microscopy images depicting HA localization (in red) within a section of the epidermis obtained from chicken backskin. Top and bottom panels correspond to early stages of feather morphogenesis (7.5 dpc and 8.5 dpc). The hatched white line represents the basement membrane (BM). The dermal condensate is highlighted with a diamond-like hatched outline (bottom panel), located below the BM. DAPI staining depicts cellular nuclei (blue).

FIG. 24 represents fluorescent microscopy images depicting cell survival and viability of DP cells that were encapsulated in alginate beads during in vitro culturing. Cells were visualized using 2 probes, calcein AM (green) and ethidium homodimer-1 (red) via confocal microscopy. The left panel represents a culture of DP cells microencapsulated in alginate beads at day 0 and the right panel after 10 days in culture. Viable cells are depicted as green images, dead cells are depicted as red images.

SUMMARY OF THE INVENTION

Figure 1:
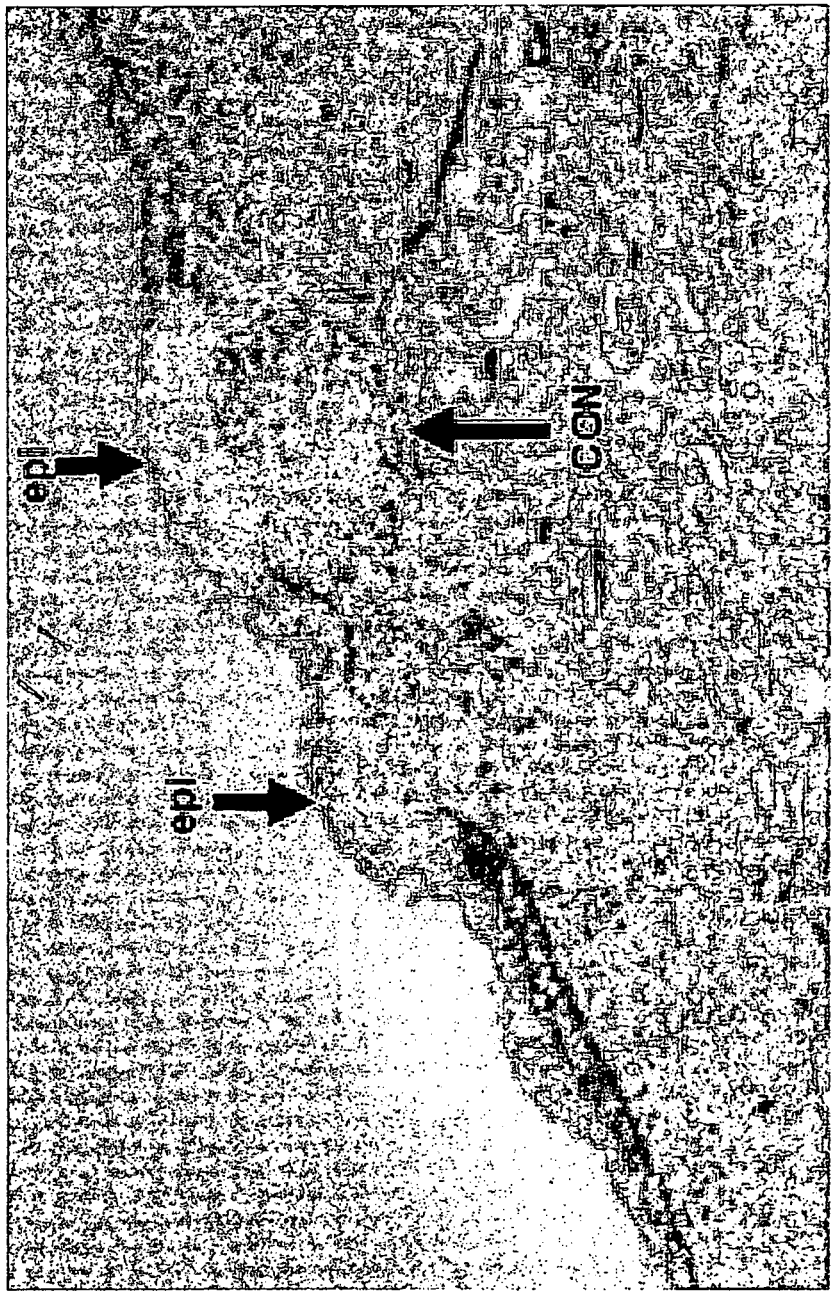
FIG. 1 is a light microscopy image depicting Alcian blue staining (in the absence of $MgCl_2$ treatment) utilized to monitor glycosaminoglycans (GAGS) in the developing hair follicle. Epi, epidermis; CON, dermal condensate containing GAGS (such as hyaluronan).

The present invention relates to methods of aggregating dermal papilla cells, methods of aggregating dermal sheath cells, methods for promoting the formation of hair follicles, and methods for promoting hair growth.

The invention provides methods for aggregating dermal papilla cells or dermal sheath cells in suspension culture. In some embodiments, the culture is a hanging drop culture.

The invention also provides methods for aggregating dermal papilla cells or dermal sheath cells in suspension culture, where the culture is contacted with an effective amount of an enzyme, wherein a substrate of the enzyme is an extracellular matrix molecule in the suspension culture. In some embodiments, the culture is a hanging drop culture. In certain embodiments, the enzyme is a hyaluronidase.

The invention provides for a method for aggregating dermal papilla cells or dermal sheath cells or a combination thereof, the method comprising: a) growing dermal papilla cells or dermal sheath cells or a combination thereof in suspension culture so as to obtain a compact aggregate of cells. The invention also provides for a method for aggregating dermal papilla cells or dermal sheath cells or a combination thereof, the method comprising: a) growing dermal papilla cells or dermal sheath cells or a combination thereof in suspension culture; and b) admixing with the culture an effective amount of a substance capable of reducing the amount of extracellular matrix in the suspension culture, so as to obtain a compact aggregate of cells. In one embodiment, the suspension culture comprises a soluble factor. In one embodiment, the suspension culture is a hanging drop culture.

In one embodiment, the substance is a protein. In one embodiment, the protein is an enzyme. In one embodiment, the protein degrades one or molecules in extracellular matrix. In one embodiment, a substrate of the enzyme is an extracellular matrix molecule in the suspension culture. In one embodiment, the enzyme is a hyaluronidase, a collagenase, a chondroitinase, or a combination thereof. In one embodiment, hyaluronidase is admixed with the culture in the amount of from about 20 U/ml to about 50 U/ml for up to about 15 days. In one embodiment, the hyaluronidase is Hyal-1, Hyal-2, Hyal-3, or a combination thereof. In one embodiment, the hanging drop culture contains less than about 9,000 cells. In one embodiment, the hanging drop culture contains less than about 7,000 cells. In one embodiment, the hanging drop culture contains less than about 5,000 cells. In one embodiment, the hanging drop culture contains less than about 3,000 cells. In one embodiment, the suspension culture further contains epithelial cells. In one embodiment, the epithelial cells are derived from hair follicle or skin. In one embodiment, the epithelial cell is a keratinocyte. In one embodiment, the hanging drop is cultured for at least 24 hours. In one embodiment, the hanging drop is cultured for at least 48 hours. In one embodiment, the hanging drop is cultured up to about 3, 4, 5, 6, 7, 8, 9, 10, 11, 12, 13, 14, or 15 days. In one embodiment, the hanging drop is cultured until expression of an inductivity marker gene is reduced. In one embodiment, the inductivity marker gene comprises Wnt10b, WISE, versican, or a combination thereof. In one embodiment, the soluble factor is added exogenously. In one embodiment, the soluble factor is administered in the amount of from about 5 ng/ml to about 300 ng/ml. In one embodiment, the soluble factor comprises periostin, follistatin, Wise, Wnt10b, any one or more soluble factors in Table 1 and Table 2, or any combination thereof. In one embodiment, the method further comprises the step of transfecting the cells with a nucleic acid encoding: Wnt10b, periostin, follistatin, Wise, one or more soluble factors listed in Table 1 and Table 2, or any combination thereof. In one embodiment, the method further comprises the step of grafting the compact aggregate of cells into the skin of a subject. In one embodiment, the subject is a mammal. In one embodiment, the mammal is a human, a mouse, a dog, a cat, a horse, a cow, or a bird. In one embodiment, the cells are autologous to the subject. In one embodiment, the method further comprises placing the compact aggregate of cells into a post-suspension culture. In one embodiment, the post-suspension culture comprises a biodegradable scaffold. In one embodiment, the biodegradable scaffold comprises alginate. In one embodiment, the cells comprise primary cells, secondary cells, passaged secondary cells, or a cell line. In one embodiment, the cells are obtained or derived from a mammal. In one embodiment, the mammal is a human, a mouse, a dog, a cat, a horse, a cow, or a bird.

The invention also provides for a method for promoting formation of hair follicles from aggregated dermal papilla cells or dermal sheath cells or a combination thereof, the method comprising: a) growing dermal papilla cells or dermal sheath cells or a combination thereof in suspension culture; b) admixing hyaluronidase with the culture for a time of from about 1 day to about 15 days, so as to produce compact, aggregated dermal papilla cells or dermal sheath cells; and c) growing the culture for a sufficient time so as form hair follicles. In one embodiment, the suspension culture comprises a soluble factor. In one embodiment, the suspension culture is a hanging drop culture. In one embodiment, the hanging drop culture contains less than about 9,000 cells. In one embodiment, the hanging drop culture contains less than about 7,000 cells. In one embodiment, the hanging drop culture contains less than about 5,000 cells. In one embodiment, the hanging drop culture contains less than about 3,000 cells. In one embodiment, the culture further comprises epithelial cells. In one embodiment, the epithelial cells are derived from a hair follicle or skin. In one embodiment, the epithelial cell is a keratinocyte. In one embodiment, the hyaluronidase is admixed in the amount of from about 20 U/ml of culture media to about 50 U/ml of culture media. In one embodiment, the hyaluronidase is Hyal-1, Hyal-2, Hyal-3, or a combination thereof. In one embodiment, the growing step is for at least 24 hours. In one embodiment, the suspension culture is cultured until expression of an inductivity marker gene is reduced. In one embodiment, the inductivity marker gene comprises Wnt10b, WISE, versican, or a combination thereof. In one embodiment, the soluble factor is added to the growing culture. In one embodiment, the soluble factor is admixed to the culture in the amount of from about 5 ng/ml culture media to about 300 ng/ml of culture media. In one embodiment, the soluble factor comprises periostin, follistatin, Wise, Wnt10h, any one or more soluble factors in Table 1 and Table 2, or any combination thereof. In one embodiment, the method further comprises transfecting the cells with a nucleic acid encoding Wnt10b, periostin, follistatin, Wise, or one or more soluble factors listed in Table 1 and Table 2, or any combination thereof. In one embodiment, the method further comprises grafting the hair follicles into the skin of a subject. In one embodiment, the subject is a mammal. In one embodiment, the mammal is a human, mouse, dog, cat or bird. In one embodiment, the cells are autologous to the subject. In one embodiment, the method further comprises placing the hair follicles into a post-suspension culture or wherein the growing takes place in a post-suspension culture. In one embodiment, the post-suspension culture comprises a biodegradable scaffold. In one embodiment, the biodegradable scaffold comprises alginate. In one embodiment, the cells comprise primary cells, secondary cells, passaged secondary cells, or a cell line. In one embodiment, the cells are from a mammal. In one embodiment, the mammal is a human, a mouse, a dog, a cat, a horse, a cow, or a bird.

Additionally, the invention provides methods for aggregating dermal papilla cells or dermal sheath cells in suspension culture, where the culture is contacted with an effective amount of an enzyme, wherein a substrate of the enzyme is an extracellular matrix molecule in the suspension culture, and the culture medium is supplemented with an effective amount of a soluble factor. In some embodiments, the culture is a hanging drop culture. In certain embodiments, the enzyme is a hyaluronidase. In further embodiments of the invention, the soluble factor is added exogenously. In other embodiments, the soluble factor is periostin, follistatin, Wise, or Wnt10b. In some embodiments, the soluble factor is selected from the group of soluble factors consisting of Table 1 and Table 2.

The invention provides methods for promoting formation of hair follicles from aggregated dermal papilla cells or dermal sheath cells grown in suspension culture wherein the culture is contacted with a hyaluronidase enzyme from about 21 days to about 35 days, so as to produce aggregated dermal papilla cells or dermal sheath cells, and the culture is grown for a sufficient time, so as to permit formation of hair follicles. In some embodiments, the culture is a hanging drop culture. In certain embodiments, the enzyme is a hyaluronidase.

The invention also provides methods for promoting formation of hair follicles from aggregated dermal papilla cells or dermal sheath cells grown in suspension culture wherein the culture medium is supplemented with an effective amount of a soluble factor and the culture is contacted with a hyaluronidase enzyme from about 21 days to about 35 days, so as to produce aggregated dermal papilla cells or dermal sheath cells, and the culture is grown for a sufficient time, so as to permit formation of hair follicles. In some embodiments, the culture is a hanging drop culture. In certain embodiments, the enzyme is a hyaluronidase. In further embodiments of the invention, the soluble factor is added exogenously. In other embodiments, the soluble factor is periostin, follistatin, Wise, or Wnt10b. In some embodiments, the soluble factor is selected from the group of soluble factors consisting of Table 1 and Table 2.

The invention provides methods for the condensing of dermal papilla cells or dermal sheath cells wherein hyaluronic acid is degraded within a suspension culture of dermal papilla cells or dermal sheath cells and the suspension culture is grown under conditions that permit uptake of hyaluronic acid bound to CD44 into the dermal papilla cells or dermal sheath cells, so as to cause condensing of dermal papilla cells or dermal sheath cells. In some embodiments, the culture is a hanging drop culture.

In addition, the invention provides methods for aggregating dermal papilla cells or dermal sheath cells, wherein a suspension culture of dermal papilla cells or dermal sheath cells is provided, an enzyme capable of degrading hyaluronic acid is admixed to the suspension culture, and the dermal papilla cells or dermal sheath cells are contacted with a vector encoding a soluble factor or a transcription factor so as to transfect the dermal papilla cells or dermal sheath cells with the vector and produce the soluble factor or transcription factor, thereby aggregating the dermal papilla cells or dermal sheath cells. In some embodiments, the culture is a hanging drop culture. In other embodiments, the soluble factor harbored by the vector is periostin, follistatin, Wise, or Wnt10b. In certain embodiments, the soluble factor harbored by the vector is selected from the group of soluble factors consisting of Table 1 and Table 2. In further embodiments, the transcription factor harbored by the vector is selected from the group of transcription factors consisting of Table 1 and Table 2.

The invention provides methods for promoting hair growth in a subject, wherein dermal papilla cells or dermal sheath cells are obtained, and cultured in a suspension culture where the cells are treated with an effective amount of an enzyme, wherein a substrate of the enzyme is an extracellular matrix molecule in the suspension culture, and the cells subsequently are grafted onto the skin of a subject, thereby promoting hair growth in the subject. In some embodiments, the subject is a mammal. In other embodiments, the dermal papilla cells or dermal sheath cells are autologous to the subject. In certain embodiments, the culture is a hanging drop culture. In further embodiments, the enzyme is a hyaluronidase.

The invention provides methods for promoting hair growth in a subject, wherein dermal papilla cells or dermal sheath cells are obtained and cultured in a suspension culture that is supplemented with an effective amount of a soluble factor, and the cells are treated with an effective amount of an enzyme, wherein a substrate of the enzyme is an extracellular matrix molecule in the suspension culture, and the cells subsequently are grafted onto the skin of a subject, thereby promoting hair growth in the subject. In some embodiments, the subject is a mammal. In other embodiments, the dermal papilla cells or dermal sheath cells are autologous to the subject. In certain embodiments, the culture is a hanging drop culture. In further embodiments, the enzyme is a hyaluronidase. Yet, in further embodiments of the invention, the soluble factor is added exogenously. Yet in other embodiments of the invention, the soluble factor is periostin, follistatin, Wise, or Wnt10b. In some embodiments, the soluble factor is selected from the group of soluble factors consisting of Table 1 and Table 2.

Additionally, the invention provides methods for promoting hair growth in a subject, wherein an effective amount of a hyaluronidase enzyme to promote condensation of dermal papilla cells or dermal sheath cells is applied to the skin of a subject, whereby the hyaluronidase enzyme is prepared in a formulation that contains: (a) an effective agent for controlling the absorption of hyaluronidase enzyme by the skin; (b) an agent for promoting penetration of hyaluronidase enzyme into the skin; and (c) a vehicle for the hyaluronidase enzyme and agents of (a) and (b), so as to promote hair growth in the subject. In some embodiments, the subject is a mammal. In other embodiments, the dermal papilla cells or dermal sheath cells are autologous to the subject. In certain embodiments, the culture is a hanging drop culture. In further embodiments, the enzyme is a hyaluronidase. In further embodiments, the vehicle is water or ethanol.

The invention also provides methods for promoting hair growth in a subject, wherein an effective amount of a hyaluronidase enzyme and an effective amount of a soluble factor to promote condensation of dermal papilla cells or dermal sheath cells is applied to the skin of a subject, whereby the hyaluronidase enzyme and the soluble factor is prepared in a formulation that contains: (a) an effective agent for controlling the absorption of hyaluronidase enzyme and the soluble factor by the skin; (b) an agent for promoting penetration of hyaluronidase enzyme and the soluble factor into the skin; and (c) a vehicle for the hyaluronidase enzyme, the soluble factor and agents of (a) and (b), so as to promote hair growth in the subject. In some embodiments, the subject is a mammal. In other embodiments, the dermal papilla cells or dermal sheath cells are autologous to the subject. In certain embodiments, the culture is a hanging drop culture. In further embodiments, the enzyme is a hyaluronidase. Yet in other embodiments of the invention, the soluble factor is periostin, follistatin, Wise, or Wnt10b. In some embodiments, the soluble factor is selected from the group of soluble factors consisting of Table 1 and Table 2. In certain embodiments, the vehicle is water or ethanol.

DETAILED DESCRIPTION OF THE INVENTION

Condensation of dermal cells leading to the formation of dermal papilla (DP) is initiated in part by CD44-mediated degradation of hyaluronic acid (HA). HA degradation drives dermal cell condensation, and potentially their ability to induce the hair follicle once they are aggregated. Long-term cultures of DP are not able to induce the formation of hair follicles when re-implanted due to DP cells losing inductive capabilities. The present invention provides for a new method to promote hair growth by maintaining the inductive properties of DP cells via a CD44-mediated pathway, which thereby allows for the formation of hair follicles. The present invention also provides for a new method to aggregate DP cells wherein DP cells are grown in 3D-culture and treated enzymatically in order to re-gain or maintain their inductivity, thus re-capitulating a natural developmental process. Of course, the methods of the invention can be carried out in conjunction with the use of introduced genes, mechanical scaffolds and/or biomaterials.

Overview of the Integument

The integument (or skin) is the largest organ of the body and is a highly complex organ covering the external surface of the body. It merges, at various body openings, with the mucous membranes of the alimentary and other canals. The integument performs a number of essential functions such as maintaining a constant internal environment via regulating body temperature and water loss; excretion by the sweat glands; but predominantly acts as a protective barrier against the action of physical, chemical and biologic agents on deeper tissues. Skin is elastic and except for a few areas such as the soles, palms, and ears, it is loosely attached to the underlying tissue. It also varies in thickness from 0.5 mm (0.02 inches) on the eyelids ("thin skin") to 4 mm (0.17 inches) or more on the palms and soles ("thick skin") (Ross M H, Histology: A text and atlas, $3^{rd}$ edition, Williams and Wilkins, 1995: Chapter 14; Burkitt H G, et al, Wheater's Functional Histology, $3^{rd}$ Edition, Churchill Livingstone, 1996: Chapter 9).

The skin is composed of two layers: a) the epidermis and b) the dermis. The epidermis, or cuticle, is the outer layer, which is comparatively thin (0.1 mm). It is several cells thick and is composed of 5 layers: the stratum germinativum, stratum spinosum, stratum granulosum, stratum lucidum (which is limited to thick skin), and the stratum corneum. The outermost epidermal layer (the stratum corneum) consists of dead cells that are constantly shed from the surface and replaced from below by a single, basal layer of cells, called the stratum germinativum. The epidermis is composed predominantly of keratinocytes, which make up over 95% of the cell population. Keratinocytes of the basal layer (stratum germinativum) are constantly dividing, and daughter cells subsequently move upwards and outwards, where they undergo a period of differentiation, and are eventually sloughed off from the surface. The remaining cell population of the epidermis includes dendritic cells such as Langerhans cells and melanocytes. The epidermis is essentially cellular and non-vascular, containing little extracellular matrix except for the layer of collagen and other proteins beneath the basal layer of keratinocytes (Ross M H, Histology: A text and atlas, $3^{rd}$ edition, Williams and Wilkins, 1995: Chapter 14; Burkitt H G, et al, Wheater's Functional Histology, $3^{rd}$ Edition, Churchill Livingstone, 1996: Chapter 9).

The dermis is the inner layer of the skin and is composed of a network of collagenous extracellular material, blood vessels, nerves, and elastic fibers. Within the dermis are hair follicles with their associated sebaceous glands (collectively known as the pilosebaceous unit) and sweat glands. The interface between the epidermis and the dermis is extremely irregular and uneven, except in thin skin. The junction between the two layers consists of a succession of finger like connective tissue protrusions, called dermal papillae (DP). Beneath the basal epidermal cells along the epidermal-dermal interface, the specialized extracellular matrix is organized into a distinct structure called the basement membrane (Ross M H, Histology: A text and atlas, $3^{rd}$ edition, Williams and Wilkins, 1995: Chapter 14; Burkitt H G, et al, Wheater's Functional Histology, 3rd Edition, Churchill Livingstone, 1996: Chapter 9).

The mammalian hair fiber is composed of keratinized cells and develops from the hair follicle. The hair follicle is a peg of tissue derived from a downgrowth of the epidermis, which lies immediately underneath the skin's surface. The distal part of the hair follicle is in direct continuation with the external, cutaneous epidermis. Although a small structure, the hair follicle comprises a highly organized system of recognizably different layers arranged in concentric series. Active hair follicles extend down through the dermis, the hypodermis (which is a loose layer of connective tissue), and into the fat or adipose layer (Ross M H, *Histology: A text and atlas*, 3rd edition, Williams and Wilkins, 1995: Chapter 14; Burkitt H G, et al, *Wheater's Functional Histology*, 3rd Edition, Churchill Livingstone, 1996: Chapter 9).

At the base of an active hair follicle lies the hair bulb. The bulb consists of a body of dermal cells, known as the dermal papilla, contained in an inverted cup of epidermal cells known as the epidermal matrix. Irrespective of follicle type, the germinative epidermal cells at the very base of this epidermal matrix produce the hair fiber, together with several supportive epidermal layers. The lowermost dermal sheath is contiguous with the papilla basal stalk, from where the sheath curves externally around all of the hair matrix epidermal layers as a thin covering of tissue. The lowermost portion of the dermal sheath then continues as a sleeve or tube for the length of the follicle (Ross M H, *Histology: A text and atlas*, 3rd edition, Williams and Wilkins, 1995: Chapter 14; Burkitt H G, et al, *Wheater's Functional Histology*, 3rd Edition, Churchill Livingstone, 1996: Chapter 9).

Developing skin appendages, such as hair and feather follicles, rely on the interaction between the epidermis and the dermis, the two layers of the skin. In embryonic development, a sequential exchange of information between these two layers supports a complex series of morphogenetic processes, which results in the formation of adult follicle structures. However, in contrast to general skin dermal and epidermal cells, certain hair follicle cell populations, following maturity, retain their embryonic-type interactive, inductive, and biosynthetic behaviors. These properties are likely derived from the very dynamic nature of the cyclical productive follicle, wherein repeated tissue remodeling necessitates a high level of dermal-epidermal interactive communication, which is vital for embryonic development and would be desirable in other forms of tissue reconstruction.

The hair fiber is produced at the base of an active follicle at a very rapid rate. For example, follicles produce hair fibers at a rate 0.4 mm per day in the human scalp and up to 1.5 mm per day in the rat vibrissa or whiskers, which means that cell proliferation in the follicle epidermis ranks amongst the fastest in adult tissues (Malkinson F D and J T Kearn, *Int J Dermatol* 1978, 17:536-551).

The deeply embedded end bulb, where local dermal-epidermal interactions drive active fiber growth, is the most dynamic region of the hair follicle. This same region is also central to the tissue remodeling and developmental changes involved in the hair fiber's or appendage's precise alternation between growth and regression phases. The dermal papilla, a key player in these activities, appears to orchestrate the complex program of differentiation that characterizes hair fiber formation from the primitive germinative epidermal cell source (Oliver R F, *J Soc Cosmet Chem*, 1971, 22:741-755; Oliver R F and C A Jahoda, *Biology of Wool and Hair* (eds Roger et al), 1971, Cambridge University Press:51-67; Reynolds A J and CA Jahoda, *Development*, 1992, 115:587-593; Reynolds A J, et al., *J Invest Dermatol*, 1993, 101:634-38). The lowermost dermal sheath arises below the basal stalk of the papilla, from where it curves outwards and upwards. This dermal sheath then externally encloses all of the layers of the epidermal hair matrix as a thin cup of tissue and continues as a tubular arrangement for the length of the follicle. The epidermal outer root sheath also continues for the length of the follicle, which lies immediately internal to the dermal sheath in between the two layers, and forms a specialized basement membrane termed the glassy membrane. The outer root sheath constitutes little more than an epidermal monolayer in the lower follicle, but becomes increasingly thickened as it approaches the surface (Ross M H, *Histology: A text and atlas*, 3rd *edition*, Williams and Wilkins, 1995: Chapter 14; Burkitt H G, et al, *Wheater's Functional Histology*, 3rd *Edition*, Churchill Livingstone, 1996: Chapter 9).

Prior studies reported that hair fiber growth could be restored in rat whisker follicles whose end bulbs had been amputated due to regeneration of all crucial elements that were required to promote hair growth (Oliver R F, In the Skin of Vertebrates [Ed. Spearman RIC], New York Academy Press, 1980: 199-210). Studies also revealed that isolated dermal papilla cells had interactive capabilities of being able to induce hair follicles de novo when re-implanted in vivo (Oliver R F, *J Soc Cosmet Chem*, 1971, 22:741-755). Subsequent experiments further supported studies carried out in rat model systems (Reynolds A J and C A Jahoda, *Development*, 1992, 115:587-593; Reynolds A J and CA Jahoda, *PNAS*, 1991, 624:226-42; Jahoda C A, *Development*, 1992, 115: 1103-9; Jahoda C A and A J Reynolds, *J Invest Dermatol*, 1993, 101:584-90), and confirmed that dermal papillae cells from other species, including mice (Weinberg W C, et al., *J Invest Dermatol*, 1993, 100:229-236; Lichti U, et al., *J Invest Dermatol*, 1993, 101:124s-29s) and sheep (Watson S A, et al., *Br J Dermatol*, 1994, 131:827-35), had similar interactive capabilities. Human facial (Hage J J and F G Bouman, *Plast Reconstr Surg*, 1991, 88:446-51) and axillary (Inaba M and Y Inaba, *Human Body Odor, Etiology, Treatment and Related Factors*, Springer-Verlag [Tokyo], 1992: Chapter 16) follicles in situ, as well as, isolated human follicles transplanted to rodent hosts (Jahoda C A, et al. *J Invest Dermatol*, 1996, 107:804-807), have also been reported to regenerate following end bulb amputation. Further in vitro studies also strongly suggested that human follicle tissues and cells displayed highly specialized interactive properties that were seen in rodent model systems (Reynolds A J and C A Jahoda, *Sem Devel Biol*, 1993, 4:241-250).

In one embodiment, the present invention provides methods for aggregating cells that are obtained from the body of the bulb of a hair follicle. In another embodiment, the cells are dermal papilla cells. In other embodiments, the cells can be dermal sheath cells. The present invention also provides methods for promoting the formation of hair follicles from aggregated dermal papilla cells.

CD44 and its Tissue-Specific Variant Splice Forms

CD44 is a widely distributed cell surface glycoprotein receptor that is expressed in many isoform generated from a single gene via tissue and cell-type specific alternative splicing. Specific isoforms of CD44 are present at critical sites and stages of morphogenesis of several organs, particularly invaginating epithelia at sites of epithelial-mesenchymal interactions, such as in the developing tooth and hair follicle.

The CD44 gene is comprised of 20 exons, 10 of which can be alternatively spliced to generate the tissue-specific isoforms. CD44 standard form (CD44s), the predominant ~80 kD isoform, is encoded by exons 1 to 5, 16 to 18 and 20, and contains a HA-binding extracellular domain, a transmembrane domain and a cytoplasmic domain. The variant isoforms contain different combinations of exons 6-15, and are usually referred to as v1-v10. Skin dermis expresses exclusively the common CD44s form. Intriguingly, epidermal keratinocytes are among the only cells to express the larger ~180 kD variant forms, v1-10 and v3-10. This isoform is also known in the literature as epican.

Hyaluronan, the major ligand for CD44, is also present at signs of morphogenetic movements. Yet there are relatively few examples where the distribution of CD44 and HA suggested their coordinated involvement in morphogenesis. A notable example is the mediation of endocytic removal of hyaluronan by CD44 during several critical developmental events, including the development of lung and epiphyses. The colocalization of HA and CD44 in adjacent compartments of the skin during hair follicle invagination suggests that the same mechanisms may be acting during this process (Yu Q and B P Toole, *Dev Dyn*, 1997, 208:1-10).

Condensation is Mediated by CD44-HA in Other Mesenchymal Cell Types

Condensation is a pivotal stage in the development of several mesenchymal tissues. It occurs when a previously dispersed population of cells gathers together to differentiation into a single tissue type, and represents the earliest stage during organ formation when tissue specific genes are upregulated. Condensations are formed as a result of one or a combination of three processes: enhanced mitotic activity, aggregation of cells toward a center, and/or failure of cells to disperse from a center.

In hair follicle development, there is evidence against the first and third mechanisms, and all available data points toward aggregation of cells toward a center as the prevailing mechanism, although the molecular cues governing hair follicle dermal condensation remain unknown.

Condensations of the second type are generated by the reduction of intercellular spaces between cells and the resulting aggregation of a cell population. Factors that govern condensation in other mesenchymal cell types include Wnt, Shh, FGF and TGFβ family members, among others. As shown in the microarray experiment results described in EXAMPLE 3, as well as the literature, these major signaling pathways are also key players in hair follicle induction (Beaudoin G M, et al., *Proc Natl Acad Sci USA*, 2005, 102(41):14653-8; O'Shaughnessy R F, et al., *J Invest Dermatol*, 2004, 123(4):613-21; Shimizu H and B A Morgan *J Invest Dermatol*, 2004, 122(2):239-45; Andl T, et al., *Dev Cell*, 2002, 2(5):643-53; Hibino T and T Nishiyama, *J Dermatol Sci*, 2004, 35(1):9-18).

Interestingly, gene ontology analysis of the microarray dataset (EXAMPLE 3) of hair follicle development also revealed the presence of many genes involved in bone and cartilage development. This prompted for the comparison of the microarray findings (EXAMPLE 3) with literature on bone morphogenesis where the earliest stages of mesenchymal condensation are known in detail (Wheatley S. C., et al., *Development*, 1993, 119(2):295-306; Weber B, et al., *Differentiation*, 1996, 60(1):17-29) and have been shown to be mediated by CD44-HA dependent mechanisms.

The extracellular matrix (ECM) is the defining feature of connective tissue that comprises the material part of a tissue that is not a part of a cell. The ECM's main components are various glycoproteins and proteoglycans. In the case of bone, the ECM also comprises mineral deposits. In most animals, the most abundant glycoproteins in the ECM are collagens (such as types I-XII collagen). Proteoglycans can also be glycoproteins, but are decorated with more carbohydrate chain clusters. Some examples of proteoglycans found in the ECM are chondroitin sulfate, heparan sulfate, keratan sulfate, and hyaluronic acid (HA) (Hardingham and Fosang, (1992) *FASEB J.* 6(3):861-70; Couchman, (1993) *J Invest Dermatol.* 101(1 Suppl): 60S-64S).

One mechanism to reduce the space between two cells during condensation toward a center is by removal of HA. High HA concentrations are able to block aggregation of certain cell types, whilst low concentrations of HA can have the opposite effect. The removal of HA can be accomplished in two ways. The first involves finely tuned control of synthesis of HA from one of the HAS enzymes. The maintenance of HA biosynthesis and the timing of the shutdown of HAS2 expression in the hair follicle dermis, akin to its role in the formation of other condensations, may control the size and position of the future dermal condensate.

Secondly, removal of HA is also controlled at the level of internalization and degradation by CD44. HA-mediated aggregation is dependent on binding of HA to an endogenous receptor, most commonly CD44, which is present on a neighboring cell. The observed increase in CD44 expression in the hair follicle dermal condensate may function to facilitate HA removal by endocytosis and subsequent intracellular degradation by lysosomal hyaluronidase. There six types of hyaluronidases that have been described to date: Hyal-1, Hyal-2, Hyal-3, Hyal-4, Spam1, and Hyalp-1 (Csoka et al., (2001) *Matrix Biology* 20: 499-508). The breakdown products of HA are known to activate signaling pathways that affect actin filament alignment, and perhaps influence cell shape and movements that are highly dynamic during hair follicle morphogenesis. The localization of CD44-HA components in the developing hair follicle suggests that either (or potentially) both mechanisms could be involved in the control of hair follicle dermal condensation.

The present invention provides methods for aggregating cells that are obtained from the body of the bulb of a hair follicle. In one embodiment, the cells are dermal papilla cells. In another embodiment, the cells are dermal sheath cells. In a further embodiment, cells are grown in a suspension culture (for example, a three-dimensional culture such as a hanging drop culture) in the presence of an effective amount of enzyme, wherein the enzyme substrate is an extracellular matrix molecule in the suspension culture. In a further embodiment, the enzyme is a hyaluronidase.

The present invention also provides methods for promoting the formation of hair follicles from aggregated dermal papilla cells or dermal sheath cells. In one embodiment, cells are grown in a suspension culture (for example, a three-dimensional culture such as a hanging drop culture). In another embodiment, a hyaluronidase enzyme is contacted with the suspension culture of dermal papilla cells or dermal sheath cells for about 1 day to about 15 days. In a further embodiment of the invention, the suspension culture of dermal papilla cells or dermal sheath cells contacted with a hyaluronidase enzyme for about 10 days to about 15 days is grown in culture to permit hair follicle formation.

In the present invention, a method for condensing dermal papilla cells or dermal sheath cells is also provided. In one embodiment, HA is degraded within a suspension culture (for example, a three-dimensional culture such as a hanging drop culture) of dermal papilla cells or dermal sheath cells. In another embodiment, the suspension culture is grown under conditions that permit uptake of HA bound to CD44 into dermal papilla cells or dermal sheath cells.

Wnt Signaling Pathway and Other Regulatory Developmental Proteins

The present invention is based, in part, on the discovery that a Wnt protein, for example Wnt10b, regulates CD44 gene expression in dermal papilla cells and the inductive capabilities that dermal papilla cells possess are maintained by Wnt10b signaling.

Wnts are secreted from cells, however rarely as a soluble form (Papkoff J and B Schryver, *Mol Cell Biol*, 1990, 10:2723-30; Burrus L W and McMahon A P, *Exp Cell Res*, 1995, 220:363-73; Willert K, et al., *Nature*, 2003 423:448-52). Wnt proteins are glycosylated (Mason J O, et al., *Mol Biol Cell*, 1992, 3:521-33) and palmitoylated (Willert K, et al., *Nature*, 2003 423:448-52). In the Wnt signaling pathway, Wnt binds to Frizzled (Frz), a cell surface receptor that is found on various cell types. In the presence of Dishevelled (Dsh), binding of Wnt to the Frz receptor purportedly results in inhibiting GSK3β mediated phosphorylation. Inhibition of this phosphorylation event allegedly would then subsequently halt phosphorylation-dependent degradation of β-catenin. Thus, Wnt binding stabilizes cellular β-catenin. β-catenin can then accumulate in the cytoplasm in the presence of Wnt binding and can subsequently bind to a transcription factor, such as Lef1. The β-catenin-Lef1 complex is then capable of translocating to the nucleus, where the (β-catenin-Lef1 complex can mediate transcriptional activation. Other effects and components of the Wnt signaling pathway are described in the following: Arias A M, et al., *Curr Opin Genet Dev*, 1999, 9: 447-454; Nusse R, *Development*. 2003, 130 (22):5297-305; Nelson W J and R Nusse, *Science*, 2004, 303:1483-7; Logan C Y and R Nusse, *Annu Rev Cell Dev Biol*, 2004, 20:781-810; Moon R T, et al., *Nat Rev Genet*, 2004, 5(9):691-701; Brennan K R and A M Brown, *J Mammary Gland Biol Neoplasia*, 2004, 9(2):119-31; Johnson M L, et al., *Bone Miner Res*, 2004, 19(11):1749-57; Nusse R, *Nature*, 2005, 438:747-9; Reya T and H Clevers *Nature*, 2005, 434: 843-50; Gregorieff A and H Clevers, *Genes Dev*, 2005, 19(8): 877-90; Bejsovec A, *Cell*, 2005, 120(1):11-4; Brembeck F H, et al., *Curr Opin Genet Dev*, 2006, 16(1):51-9 which are herein incorporated by reference.

Periostin, also known as Osf2, is a secreted cell adhesion protein first identified in bone that has homology to the insect protein Fasciclin, which mediates homophilic cell adhesion (Litvin J, et al., *Anat Record Part A*, 2005, 287:1025-12; Horiuchi K, et al., *J Bone Miner Res*, 1999, 14(7):1239-49). It is implicated in regulating cell adhesion of osteoblasts and ovarian epithelial cells, cell differentiation (vascular smooth muscle cells (VSMC) and osteoblasts), and migration of cells (VSMC and ovarian epithelial cells) (Rios H, et al., *Mol Cell Biol*, 2005, 25(24):11131-144; Litvin J, et al., *Anat Record Part A*, 2005, 287:1025-12; Litvin J, et al., *J Cell Biochem*, 2004, 92:1044-61; Oshima A, et al., *J Cell Biochem*, 2002, 86:792-804). Periostin is highly expressed in the embryonic periosteum, cardiac valves, the placenta, in developing teeth at sites of epithelial mesenchymal junctions, and in the periodontal ligament (Litvin J, et al., *Cardiovas Path*, 2006, 15:24-32; Rios H, et al., *Mol Cell Biol*, 2005, 25(24):11131-144; Lindner V, et al., *Arterioscler Throm Vast Biol*, 2005, 25:77-83; Litvin J, et al., *J Cell Biochem*, 2004, 92:1044-61; Kruzynska-Frejtag A, et al., *Dev Dyn*, 2004, 229:857-868; Horiuchi K, et al., *J Bone Miner Res*, 1999, 14(7):1239-49). It is also expressed in many cancerous tissues, and thus believed to be involved in oncogenesis (Tai I T, et al., *Carcinogenesis*, 2005, 26(5):908-15; Bao S, et al., *Cancer Cell*, 2004, 5:329-39). The Wnt signaling molecule, Wnt 3, has also been reported to regulate periostin in mouse mammary epithelial cells (Haertel-Wiesmann M, et al., *J Biol Chem*, 2000, 275 (41):32046-51).

Hair follicle formation and cycling is controlled by a balance of inhibitory and stimulatory signals. The signaling cues are potentiated by growth factors that are members of the TGFβ-BMP family. A prominent antagonist of the members of the TGFβ-BMP family is follistatin. Follistatin is a secreted protein that inhibits the action of various BMPs (such as BMP-2, -4, -7, and -11) and activins by binding to said proteins, and purportedly plays a role in the development of the hair follicle (Nakamura M, et al., *FASEB J*, 2003, 17(3):497-9; Patel K *Intl J Biochem Cell Bio*, 1998, 30:1087-93; Ueno N, et al., *PNAS*, 1987, 84:8282-86; Nakamura T, et al., *Nature*, 1990, 247:836-8; Iemura S, et al., *PNAS*, 1998, 77:649-52; Fainsod A, et al., *Mech Dev*, 1997, 63:39-50; Gamer L W, et al., *Dev Biol*, 1999, 208:222-32). Follistatin is a monomeric polypeptide that has a molecular weight of 31-42 kDa due to various post-translational modifications (Robertson D M, et al., *BBRC*, 1987, 149: 744-49). It is expressed in the hair placode, hair matrix, interfollicular epidermis, the bulge of the outer root sheath, as well as inner root sheath cells (Ohyama M, et al., *J Clin Invest*, 2006, 116(1): 249-60; Nakamura M, et al., *FASEB J*, 2003, 17(3):497-9). Knock-out mice of the Fst gene display abnormal tooth and whisker development, a taut and shiny coat, and die soon after birth (Matzuk M M, et al., *Nature*, 1995, 374:360-3). However, mice that overexpress the follistatin protein had shiny, irregular fur (Guo Q, et al., *Mol Endocrinol*, 1997, 12:96-106). These reports suggest a role for follistatin in regulating development of the hair follicle.

WISE is a secreted molecule that was first identified in Xenopus (Itasaki N, et al., *Development*, 2003, 130:4295-305). The Wise gene encodes a secreted protein that is capable of modulating the Wnt signaling pathway in a context-dependent manner and inducing posterior neural markers (Itasaki N, et al., *Development*, 2003, 130:4295-305; O'Shaughnessy R F, et al., *J Invest Dermatol*, 2004, 123:613-21). WISE is a protein that has been shown to modulate Wnt signaling and purportedly acts as a Wnt inhibitor (Beaudoin G M, et al., *PNAS*, 2005, 102(41):14653-58). Wise is expressed in dermal papilla cells, as well as the pre-cortex and bulge regions of a hair follicle during early anagen (O'Shaughnessy R F, et al., *J Invest Dermatol*, 2004, 123:613-21). However, WISE expression is lost in DP cells that are maintained in culture (O'Shaughnessy R F, et al., *J Invest Dermatol*, 2004, 123: 613-21).

The present invention provides methods for aggregating dermal papilla cells and dermal sheath cells that are obtained from the body of the bulb of a hair follicle. In one embodiment, cells are grown in a suspension culture (for example, a three-dimensional culture such as a hanging drop culture) in the presence of an effective amount of enzyme, wherein the enzyme substrate is an extracellular matrix molecule in the suspension culture. In another embodiment, the enzyme is a hyaluronidase. In other embodiments, the culture medium of the hanging drop culture is supplemented with soluble factors, such as periostin, Wnt10b, follistatin, and Wise. In further embodiments, the culture medium of the hanging drop culture is supplemented with soluble factors chosen from soluble factors listed in Table 1 and Table 2.

TABLE 1

Genes induced in the dermal papilla determined by microarray hybridization.

| Accession | Gene | Description | p-value | Fold 1 | Fold 2 | EST? |
|---|---|---|---|---|---|---|
| rc_AA892798_at | Wise | Sclerostin-like protein | 0 | 10.8 | 19.9 | N |
| rc_AI171268_at | Id3 | Inhibitor of DNA binding 3 | 0 | 2.3 | 4.2 | Y |
| rc_AA894092_at | Osf2 | Periostin | $1 \times 10^{-6}$ | 8.1 | 7.7 | N |
| X55572_at | Apod | Apolipoprotein D | $1 \times 10^{-6}$ | 5.7 | 6.8 | N |
| rc_AA858520_g_at | Fst | Follistatin | $1 \times 10^{-6}$ | 4.8 | 6.3 | Y |
| X05834_at | Fn1 | Fibronectin | $1 \times 10^{-6}$ | 3.1 | 3.1 | Y |
| rc_AI237836_at | Gnas | G-protein stimulatory subunit | $1 \times 10^{-6}$ | 2.2 | 2.3 | N |
| rc_AA875362_at | Pcolce | Procollagenase-c-proteinase enhancer 1 | $2 \times 10^{-6}$ | 4.3 | 7.0 | Y |
| U27562_at | Ecm2 | SPARC-like protein | $4 \times 10^{-6}$ | 3.9 | 3.9 | N |
| J04486_at | Igfbp2 | Insulin growth factor binding protein 2 | $5 \times 10^{-6}$ | 4.0 | 8.7 | N |
| rc_AI232078_at | Ltbp1 | Latent TGF beta binding protein 1 | $6 \times 10^{-6}$ | 5.6 | 6.7 | Y |
| rc_AA944422_at | Cnn3 | Calponin3 | $6 \times 10^{-6}$ | 2.5 | 4.8 | Y |
| X84047cds_at | Xlas | Xlas/Alex G protein | $1 \times 10^{-5}$ | 2.7 | 4.8 | N |
| U64705cds_f_at | Eif4G1 | Protein synthesis initiation factor 4 | $1 \times 10^{-5}$ | 2.0 | 2.7 | Y |
| rc_AI230256_at | Id2 | Inhibitor of DNA binding 2 | $1 \times 10^{-5}$ | 2.3 | 4.1 | N |
| rc_AA892532_at | Cabp1 | Calcium Binding protein 1 | $1 \times 10^{-5}$ | 2.1 | 2.6 | Y |
| rc_AA892066_at | Mmp15 | Rat Matrix Metalloproteinase 15 | $2 \times 10^{-5}$ | 3.2 | 2.0 | N |
| AF000942_at | Id3a | Inhibitor of DNA binding 3a | $2 \times 10^{-5}$ | 2.1 | 3.8 | Y |
| rc_AA875033_at | Fbln5 | Fibulin 5 | $2 \times 10^{-5}$ | 2.2 | 2.3 | N |
| rc_AI172064_at | Lgals1 | Galectin 1 | $4 \times 10^{-5}$ | 2.3 | 4.4 | Y |
| AF072892_s_at | Cspg2 | Versican | $5 \times 10^{-5}$ | 2.5 | 4.0 | N |
| A03913cds_s_at | Pn-1 | Protease Nexin 1 | $7 \times 10^{-5}$ | 2.3 | 4.4 | Y |
| L26268_at | Btg1 | B-cell translocation gene, anti proliferative | $1 \times 10^{-4}$ | 2.3 | 2.9 | N |

Accession number of the affymetrix probe set; Gene, gene symbol; p-value is the median p-value over the 6 crosswise comparisons and Fold1 and Fold2 are the absolute fold increase in the DP over the DS in two representative experiments. EST?, was the gene detected in the EST sequencing project of Sleeman et al., 2000.

TABLE 2

Selected genes expressed in both the dermal papilla and dermal sheath

| | |
|---|---|
| TNF intracellular domain-interacting protein | insulin-like growth factor binding protein 3 |
| a disintegrin and metalloproteinase domain 17 | interferon regulatory factor 1 |
| CIKS (Nuclear factor NF-kappa-B activator 1) | Jun-B oncogene |
| afadin | junction plakoglobin |
| agrin | Kruppel-like factor 4 (gut) |
| alkaline phosphastase, tissue-nonspecific | Kruppel-like factor 9 |
| annexin 1 | lamin A |
| apolipoprotein B | laminin, beta 2 |
| apolipoprotein E | lectin, galactose binding, soluble 5 |
| beclin 1 (coiled-coil, myosin-like BCL2-interacting protein) | lectin, galactose binding, soluble 7 |
| bone morphogenetic protein 4 | matrix Gla protein |
| calmodulin 1 | matrix metalloproteinase 14, membrane-inserted |
| calmodulin 3 | matrix metalloproteinase 3 |
| calnexin | mitogen activated protein kinase kinase 2 |
| Calreticulin | mitogen activated protein kinase kinase kinase 12 |
| cathepsin K | N-myc downstream-regulated gene 2 |
| cathepsin S | Notch gene homolog 1, (*Drosophila*) |
| CCAAT/enhancer binding protein (C/EBP), beta | p21 (CDKNIA)-activated kinase 2 |
| CD81 antigen | PKC-delta binding protein |
| CD63 antigen | procollagen, type 1, alpha 2 |
| cellular retinoic acid binding protein 2 | prothymosin alpha |
| cellular retinoic acid binding protein 1 | rabaptin 5 |
| collagen, type 1, alpha 1 | Ras-related GPT-binding protein raga |
| collagen, type III, alpha 1 | Rat mRNA for beta-tubulin T beta15 |
| collagen, type V, alpha 1 | *Rattus norvegicus* plectin 1, |
| cyclin D1 | receptor-like tyrosine kinase |
| cystatin B | rhoB gene |
| cystatin C | runt related transcription factor 1 |
| dyskeratosis congenita 1, dyskerin | S100 calcium-binding protein A4 |
| Eph receptor B2 | S-100 related protein, clone 42C |
| fatty acid binding protein 4 | Secreted acidic cysteine rich glycoprotein |
| FGF receptor activating protein 1 | Serine (or cysteine) proteinase inhibitor, clade G |
| fibroblast growth factor receptor 1 | proteinase inhibitor, clade H, member 1 |

TABLE 2-continued

Selected genes expressed in both the dermal papilla and dermal sheath

| | |
|---|---|
| FK506-binding protein 1a | serum/glucocorticoid regulated kinase |
| follistatin-like | smooth muscle alpha-actin |
| fyn proto-oncogene | syndecan 1 |
| GABA(A) receptor-associated protein like 2 | syndecan 4 |
| gonadotropin-releasing hormone receptor | thymosin beta-4 |
| growth arrest specific 6 | tissue inhibitor of metalloproteinase 2 |
| growth factor receptor bound protein 2 | Transferrin |
| inhibin alpha | tubulin, beta 5 |
| Inhibitor of DNA binding 1 | v-akt murine thymoma viral oncogene homolog 1 |
| Insulin-like growth factor 1 | vimentin |
| Insulin-like growth factor 2 | |

The present invention also provides methods for promoting the formation of hair follicles from aggregated dermal papilla cells or dermal sheath cells. In one embodiment, cells are grown in a suspension culture (for example, a three-dimensional culture such as a hanging drop culture). In another embodiment, a hyaluronidase enzyme is contacted with the suspension culture of dermal papilla cells or dermal sheath cells for about 21 days to about 35 days. In a further embodiment of the invention, the suspension culture of dermal papilla cells or dermal sheath cells contacted with a hyaluronidase enzyme for about 21 days to about 35 days is grown in culture to permit hair follicle formation. In other embodiments, the culture medium of the hanging drop culture is supplemented with soluble factors, such as periostin, Wnt10b, follistatin, and Wise. In further embodiments, the culture medium of the hanging drop culture is supplemented with soluble factors chosen from soluble factors listed in Table 1 and Table 2.

Cell Therapy

DNA Manipulation for Cell Therapy Methods:

One skilled in the art understands that polypeptides (for example Wnt 10b, periostin, follistatin, and the like) can be obtained in several ways, which include, but are not limited to, isolating the protein via biochemical means or expressing a nucleotide sequence encoding the protein of interest by genetic engineering methods.

The invention provides for a nucleic acid encoding a Wnt10b molecule, a periostin molecule, a follistatin molecule, or a WISE molecule. In one embodiment, the molecule (such as a Wnt10b molecule, a periostin molecule, a follistatin molecule, or a WISE molecule) is an expression cassette, for example to achieve overexpression in a cell. The nucleic acids of the invention can be an RNA, cDNA, cDNA-like, or a DNA nucleic acid molecule of interest in an expressible format, such as an expression cassette, which can be expressed from the natural promoter or a derivative thereof or an entirely heterologous promoter. Alternatively, the nucleic acid of interest can encode an anti-sense RNA. The nucleic acid of interest can encode a protein (for example, follistatin, WISE, periostin, or Wnt10b), and may or may not include introns.

The nucleotide and amino acid sequences of various Wnt molecules from various organisms are known (please refer to Lee F S, et al., *Proc Natl Acad Sci USA*, 1995, 92(6):2268-72; Gavin B J, et al., *Genes Dev*, 1990, 4(12B):2319-32.; and Christiansen J H, et al., *Mech Dev*, 1995, 51(2-3):341-50, which describe, for example, murine Wnt1, Wnt2, Wnt3a, Wnt3b, Wnt4, Wnt5a, Wnt 5b, Wnt6, Wnt7a, Wnt7b, Wnt8a, Wnt8b, Wnt10b, Wnt11, Wnt12; van't Veer L J, et al., *Mol Cell Biol*, 1984, 4:2532-2534; Wainwright B J, et al., *EMBO J*, 1988, June; 7(6):1743-8; U.S. Pat. No. 6,159,950; United States Patent Application Publication 2005/0271632; PCT Publication WO 2001/74164; and, PCT Publication WO 1995/17416 (which describes human Wnt1, Wnt2, Wnt3, Wnt4, Wnt5a, Wnt7a and Wnt7b)). The amino acid sequences for Wise molecules of various organisms are found in Itasaki N, et al., *Development*, 2003, 130:4295-305 and O'Shaughnessy R F, et al., *J Invest Dermatol*, 2004, 123:613-21. The amino acid sequences for periostin molecules are described in Takeshita S, et al., *Biochem J*, 1993, 294:271-278; Horiuchi K, et al., *J Bone Miner Res*, 1999, 14(7):1239-49; Litvin J, et al., *J Cell Biochem*, 2004, 92:1044-61; and Litvin J, et al., *Anat Record Part A*, 2005, 287:1025-12. The amino acid sequences for follistatin molecules can be found in Shimasaki S, et al., *Mol Endocrinol*, 1989, 3(4):651-9; and Nakamura T et al., *Science* 247 (4944), 836-838 (1990). The references above are herein incorporated by reference.

In one embodiment of the present invention, the gene encoding a protein of interest, (for example follistatin, WISE, periostin, or Wnt10b), can be cloned from either a genomic library or a cDNA according to standard protocols familiar to one skilled in the art. A cDNA, for example encoding follistatin, WISE, periostin, or Wnt10b, can be obtained by isolating total mRNA from a suitable cell line. Double stranded cDNAs can be prepared from the total mRNA using methods known in the art, and subsequently can be inserted into a suitable plasmid or bacteriophage vector. Genes can also be cloned using PCR techniques well established in the art. In one embodiment, a gene that encodes follistatin, WISE, periostin, or Wnt10b can be cloned via PCR in accordance with the nucleotide sequence information provided by Genbank, and additionally by this invention. In a further embodiment, a DNA vector containing a follistatin, WISE, periostin, or Wnt10b cDNA can act as a template in PCR reactions wherein oligonucleotide primers designed to amplify a region of interest can be used, so as to obtain an isolated DNA fragment encompassing that region.

An expression vector of the current invention can include nucleotide sequences that encode either a follistatin, WISE, periostin, or Wnt10b protein linked to at least one regulatory sequence in a manner allowing expression of the nucleotide sequence in a host cell. Regulatory sequences are well known to those skilled in the art, and can be selected to direct the expression of a protein of interest (such as follistatin, WISE, periostin, or Wnt10b) in an appropriate host cell as described in Goeddel, *Gene Expression Technology: Methods in Enzymology* 185, Academic Press, San Diego, Calif. (1990). Non-limiting examples of regulatory sequences include: polyadenylation signals, promoters (such as CMV, ASV, SV40, or other viral promoters such as those derived from bovine papilloma, polyoma, and Adenovirus 2 viruses (Fiers, et al., 1973, *Nature* 273:113; Hager G L, et al., *Curr Opin Genet Dev*, 2002, 12(2):137-41) enhancers, and other expression control elements.

One skilled in the art also understands that enhancer regions, which are those sequences found upstream or downstream of the promoter region in non-coding DNA regions, are also important in optimizing expression. If needed, origins of replication from viral sources can be employed, such as if a prokaryotic host is utilized for introduction of plasmid DNA. However, in eukaryotic organisms, chromosome integration is a common mechanism for DNA replication.

It is understood by those skilled in the art that for stable transfection of mammalian cells, a small fraction of cells can integrate introduced DNA into their genomes. The expression vector and transfection method utilized can be factors that contribute to a successful integration event. For stable amplification and expression of a desired protein, a vector harboring DNA encoding a protein of interest (for example, follistatin, WISE, periostin, or Wnt10b) is stably integrated into the genome of eukaryotic cells (for example mammalian cells, such as cells from the end bulb of the hair follicle), resulting in the stable expression of transfected genes. An exogenous nucleic acid sequence can be introduced into a cell (such as a mammalian cell, either primary or secondary cell as described above) by homologous recombination as disclosed in U.S. Pat. No. 5,641,670, the contents of which are herein incorporated by reference.

A gene that encodes a selectable marker (for example, resistance to antibiotics or drugs, such as ampicillin, G418, and hygromycin) can be introduced into host cells along with the gene of interest in order to identify and select clones that stably express a gene encoding a protein of interest. The gene encoding a selectable marker can be introduced into a host cell on the same plasmid as the gene of interest or can be introduced on a separate plasmid. Cells containing the gene of interest can be identified by drug selection wherein cells that have incorporated the selectable marker gene will survive in the presence of the drug. Cells that have not incorporated the gene for the selectable marker die. Surviving cells can then be screened for the production of the desired protein (for example, follistatin, WISE, periostin, or Wnt10b).

Cell Transfection for Cell Therapy: A eukaryotic expression vector can be used to transfect cells in order to produce proteins (for example, follistatin, WISE, periostin, or Wnt10b) encoded by nucleotide sequences of the vector. Mammalian cells (such as isolated cells from the hair bulb; for example dermal sheath cells and dermal papilla cells and the like) can harbor an expression vector (for example, one that contains a gene encoding follistatin, WISE, periostin, or Wnt10b) via introducing the expression vector into an appropriate host cell via methods known in the art.

An exogenous nucleic acid can be introduced into a cell via a variety of techniques known in the art, such as lipofection, microinjection, calcium phosphate or calcium chloride precipitation, DEAE-dextrin-mediated transfection, or electroporation. Electroporation is carried out at approximate voltage and capacitance to result in entry of the DNA construct(s) into cells of interest (such as cells of the end bulb of a hair follicle, for example dermal papilla cells or dermal sheath cells). Other methods used to transfect cells can also include calcium phosphate precipitation, modified calcium phosphate precipitation, polybrene precipitation, microinjection, liposome fusion, and receptor-mediated gene delivery.

Cells to be genetically engineered can be primary and secondary cells, which can be obtained from various tissues and include cell types which can be maintained propagated in culture. Non-limiting examples of primary and secondary cells include epithelial cells (for example, dermal papilla cells), neural cells, endothelial cells, glial cells, fibroblasts, muscle cells (such as myoblasts) keratinocytes, formed elements of the blood (e.g., lymphocytes, bone marrow cells), and precursors of these somatic cell types.

Vertebrate tissue can be obtained by methods known to one skilled in the art, such a punch biopsy or other surgical methods of obtaining a tissue source of the primary cell type of interest. In one embodiment, a punch biopsy or removal can be used to obtain a source of keratinocytes, fibroblasts, endothelial cells, or mesenchymal cells (for example, hair follicle cells or dermal papilla cells). In another embodiment, removal of a hair follicle can be used to obtain a source of fibroblasts, keratinocytes, endothelial cells, or mesenchymal cells (for example, hair follicle cells or dermal papilla cells). A mixture of primary cells can be obtained from the tissue, using methods readily practiced in the art, such as explanting or enzymatic digestion (for examples using enzymes such as pronase, trypsin, collagenase, elastase dispase, and chymotrypsin). Biopsy methods have also been described in United States Patent Application Publication 2004/0057937 and PCT application publication WO 2001/32840, and are hereby incorporated by reference.

Primary cells can be acquired from the individual to whom the genetically engineered primary or secondary cells are administered. However, primary cells can also be obtained from a donor, other than the recipient, of the same species. The cells may also be obtained from another species (for example, rabbit, cat, mouse, rat, sheep, goat, dog, horse, cow, bird, or pig). Primary cells can also include cells from an isolated vertebrate tissue source grown attached to a tissue culture substrate (for example, flask or dish) or grown in a suspension; cells present in an explant derived from tissue; both of the aforementioned cell types plated for the first time; and cell culture suspensions derived from these plated cells. Secondary cells can be plated primary cells that are removed from the culture substrate and replated, or passaged, in addition to cells from the subsequent passages. Secondary cells can be passaged one or more times. These primary or secondary cells can harbor expression vectors harboring a gene that encodes a protein of interest (such as follistatin, WISE, periostin, or Wnt10b).

Cell Culturing for Cell Therapy: Various culturing parameters can be used with respect to the host cell being cultured. Appropriate culture conditions for mammalian cells are well known in the art (Cleveland W L, et al., *J Immunol Methods*, 1983, 56(2): 221-234) or can be determined by the skilled artisan (see, for example, *Animal Cell Culture: A Practical Approach 2nd Ed.*, Rickwood, D. and Hames, B. D., eds. (Oxford University Press: New York, 1992)), and vary according to the particular host cell selected. Commercially available medium can be utilized. Non-limiting examples of medium include, for example, Minimal Essential Medium (MEM, Sigma, St. Louis, Mo.); Dulbecco's Modified Eagles Medium (DMEM, Sigma); Ham's F10 Medium (Sigma); HyClone cell culture medium (HyClone, Logan, Utah); RPMI-1640 Medium (Sigma); and chemically-defined (CD) media, which are formulated for particular cell types, e.g., CD-CHO Medium (Invitrogen, Carlsbad, Calif.).

The media described above can be supplemented as necessary with supplementary components or ingredients, including optional components, in appropriate concentrations or amounts, as necessary or desired. Cell medium solutions provide at least one component from one or more of the following categories: (1) an energy source, usually in the form of a carbohydrate such as glucose; (2) all essential amino acids, and usually the basic set of twenty amino acids plus cysteine; (3) vitamins and/or other organic compounds required at low concentrations; (4) free fatty acids or lipids, for example linoleic acid; and (5) trace elements, where trace elements are defined as inorganic compounds or naturally occurring elements that are typically required at very low concentrations, usually in the micromolar range.

The medium also can be supplemented electively with one or more components from any of the following categories: (1) salts, for example, magnesium, calcium, and phosphate; (2) hormones and other growth factors such as, serum, insulin, transferrin, and epidermal growth factor; (3) protein and tissue hydrolysates, for example peptone or peptone mixtures which can be obtained from purified gelatin, plant material, or animal byproducts; (4) nucleosides and bases such as, adenosine, thymidine, and hypoxanthine; (5) buffers, such as HEPES; (6) antibiotics, such as gentamycin or ampicillin; (7) cell protective agents, for example pluronic polyol; and (8) galactose. In one embodiment, soluble factors can be added to the culturing medium, such as follistatin, WISE, periostin, Wnt10b, and the like).

The mammalian cell culture that can be used with the present invention is prepared in a medium suitable for the particular cell being cultured. In one embodiment, the cell culture medium can be one of the aforementioned (for example, MEM) that is supplemented with serum from a mammalian source (for example, fetal bovine serum (FBS)). In another embodiment, the medium can be a conditioned medium to sustain the growth of cells obtained from the hair bulb of a hair follicle (such as dermal papilla cells or dermal sheath cells). In a further embodiment, cells obtained from the hair bulb of a hair follicle (such as dermal papilla cells or dermal sheath cells) and are cultured in an acceptable conditioned medium, can be transfected with DNA vectors harboring genes that encode a protein of interest (such as follistatin, WISE, periostin, Wnt10b, transcription factors from Table 1 and Table 2, or soluble factors from Table 1 and Table 2). In other embodiments of the invention, cells are grown in a suspension culture (for example, a three-dimensional culture such as a hanging drop culture) in the presence of an effective amount of enzyme, wherein the enzyme substrate is an extracellular matrix molecule in the suspension culture. In another embodiment, the enzyme is a hyaluronidase. Cells obtained from the hair bulb of a hair follicle (such as dermal papilla cells or dermal sheath cells) can be cultivated according to methods practiced in the art, for example, as those described in PCT application publication WO 2004/044188 and in U.S. Patent Application Publication No. 2005/0272150, which are hereby incorporated by reference.

A suspension culture is a type of culture wherein cells, or aggregates of cells (such as aggregates of DP cells), multiply while suspended in liquid medium. A suspension culture comprising mammalian cells can be used for the maintenance of cell types that do not adhere or to enable cells to manifest specific cellular characteristics that are not seen in the adherent form. Some types of suspension cultures can include three-dimensional cultures or a hanging drop culture (such as the cultures described in EXAMPLES 6-8). A hanging-drop culture is a culture in which the material to be cultivated is inoculated into a drop of fluid attached to a flat surface (such as a coverglass, glass slide, Petri dish, flask, and the like), and can be inverted over a hollow surface. Cells in a hanging drop can aggregate toward the hanging center of a drop as a result of gravity. However, according to the methods of the invention, cells cultured in the presence of a protein that degrades the extracellular matrix (such as collagenase, chondroitinase, hyaluronidase, and the like) will become more compact and aggregated within the hanging drop culture, for degradation of the ECM will allow cells to become closer in proximity to one another since less of the ECM will be present.

Cells obtained from the hair bulb of a hair follicle (such as dermal papilla cells or dermal sheath cells) can be cultured as a single, homogenous population (for example, comprising DP cells) in a hanging drop culture so as to generate an aggregate of DP cells. Cells can also be cultured as a heterogeneous population (for example, comprising DP and DS cells) in a hanging drop culture so as to generate a chimeric aggregate of DP and DS cells. This can be carried out essentially as described in EXAMPLES 6-8 of this application or according to methods described in Chapter 8 of the *Handbook in Practical Animal Cell Biology: Epithelial Cell Culture* (Cambridge Univ. Press, Great Britain; 1996); Underhill C B, *J Invest Dermatol*, 1993, 101(6):820-6); or in Armstrong and Armstrong, (1990) *J Cell Biol* 110:1439-55, which are all hereby incorporated by reference in their entireties.

Three-dimensional cultures can be formed from agar (such as Gey's Agar), hydrogels (such as matrigel, agarose, and the like; Lee et al., (2004) *Biomaterials* 25: 2461-2466) or polymers that are cross-linked. These polymers can comprise natural polymers and their derivatives, synthetic polymers and their derivatives, or a combination thereof. Natural polymers can be anionic polymers, cationic polymers, amphipathic polymers, or neutral polymers. Non-limiting examples of anionic polymers can include hyaluronic acid, alginic acid (alginate), carageenan, chondroitin sulfate, dextran sulfate, and pectin. Some examples of cationic polymers, include but are not limited to, chitosan or polylysine. (Peppas et al., (2006) *Adv Mater.* 18: 1345-60; Hoffman, A. S., (2002) *Adv Drug Deliv Rev.* 43: 3-12; Hoffman, A. S., (2001) *Ann NY Acad Sci* 944: 62-73). Examples of amphipathic polymers can include, but are not limited to collagen, gelatin, fibrin, and carboxymethyl chitin. Non-limiting examples of neutral polymers can include dextran, agarose, or pullulan. (Peppas et al., (2006) *Adv Mater.* 18: 1345-60; Hoffman, A. S., (2002) *Adv Drug Deliv Rev.* 43: 3-12; Hoffman, A. S., (2001) *Ann NY Acad Sci* 944: 62-73).

In one embodiment, cells (such as DP cells, DS cells, and the like) can be grown in culture microencapsulated in alginate beads. This can be accomplished as described in EXAMPLE 10 or by Li et al., (2005)*J Dermatol Sci* 38:107-9, which is hereby incorporated by reference. One skilled in the art recognizes alginate as a useful material for implantation in biological systems because of its inherent biocompatibility and degradation properties, and its FDA approval for use in the human body (see Higasi et al., (2004) *J Biosci and Bioeng* 97:191-195; Bunger et al., (2005) *Biomaterials* 26:2353-2360; Lee et al., (2004) Biomaterials 25: 2461-2466; Li et al., (2006) *Biotechnol Prog.* 22(6):1683-9, all of which are herein incorporated by reference). In addition, immunosuppression using alginate materials is easily modifiable (Bunger et al., (2005) *Biomaterials* 26:2353-2360).

The cells suitable for culturing according to the methods of the present invention can harbor introduced expression vectors (constructs), such as plasmids and the like. The expression vector constructs can be introduced via transformation, microinjection, transfection, lipofection, electroporation, or infection. The expression vectors can contain coding sequences, or portions thereof, encoding the proteins for expression and production. Expression vectors containing sequences encoding the produced proteins and polypeptides, as well as the appropriate transcriptional and translational control elements, can be generated using methods well known to and practiced by those skilled in the art. These methods include synthetic techniques, in vitro recombinant DNA techniques, and in vivo genetic recombination which are described in J. Sambrook et al., 1989, *Molecular Cloning, A Laboratory Manual*, Cold Spring Harbor Press, Plainview, N.Y. and in F. M. Ausubel et al., 1989, *Current Protocols in Molecular Biology*, John Wiley & Sons, New York, N.Y.

Cell Implantation or Administration for Cell Therapy:

The invention provides methods for promoting hair growth in a subject wherein the method entails applying to skin of a subject an effective amount of a hyaluronidase enzyme to promote condensation of dermal papilla cells or dermal sheath cells. In one embodiment, the method can further entail applying a soluble factor to the skin of a subject that can also facilitate the promoting of dermal papilla cell or dermal sheath cell condensation. Non-limiting examples of soluble factors include periostin, follistatin, Wise, Wnt10b in addition to those factors listed in Tables 1 and 2.

The hyaluronidase enzyme can be prepared in a formulation that contains an effective agent for controlling the absorption of hyaluronidase enzyme by the skin, an agent for promoting penetration of hyaluronidase enzyme into the skin; and a vehicle for the hyaluronidase enzyme and agents described above (such as water, or an alcohol—i.e., ethanol). For topical administration, the cell aggregates (such as DP or DS aggregates) may be formulated as solutions, gels, ointments, creams, suspensions, etc. as are well-known in the art. In some embodiments, the conditioned media may be applied via transdermal delivery systems, which slowly releases the active compound for percutaneous absorption. Permeation enhancers may be used to facilitate transdermal penetration of the active factors in the conditioned media. Transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

The invention also provides methods for promoting hair growth in a subject, where dermal papilla cells or dermal sheath cells are obtained and cultured as a suspension culture (such as a three dimensional culture—for example, a hanging drop culture or culturing via microencapsulation with alginate beads); those dermal papilla cells or dermal sheath cells then are subsequently treated with an effective amount of an enzyme (such as hyaluronidase), where a substrate of the enzyme can be an extracellular matrix molecule in the suspension culture (for example, hyaluronan); and, the aggregated dermal papilla cells or dermal sheath cells are grafted onto the skin of a subject. In one embodiment, the method can further entail applying a soluble factor to the culture medium in order to facilitate the promoting of dermal papilla cell or dermal sheath cell condensation.

Various routes of administration and various sites of cell implantation can be utilized, such as, subcutaneous or intramuscular, in order to introduce the aggregated population of cells into a site of preference. Once implanted in a subject (such as a mouse, rat, or human), the aggregated cells can then stimulate the formation of a hair follicle and the subsequent growth of a hair structure at the site of introduction. In another embodiment, transfected cells (for example, cells expressing follistatin, WISE, periostin, or Wnt10b) are implanted in a subject to promote the formation of hair follicles within the subject. In further embodiments, the transfected cells are cells derived from the end bulb of a hair follicle (such as dermal papilla cells or dermal sheath cells).

Aggregated cells (for example, cells grown in a hanging drop culture) or transfected cells (for example, cells produced as described herein) maintained for 1 or more passages can be introduced (or implanted) into a subject (such as a rat, mouse, dog, cat, human, and the like). In one embodiment, cells can be derived from the end bulb of the hair follicle, such as dermal papilla cells or dermal sheath cells. In other embodiments of the invention, cells are aggregated via being grown in a hanging drop culture. In further embodiments, cells are aggregated via contacting cells in a hanging drop culture with an effective amount of an enzyme (such as hyaluronidase), wherein a substrate of the enzyme is an extracellular matrix molecule (for example, hyaluronan). In other embodiments, cells are aggregated via contacting cells in a hanging drop culture with an effective amount of soluble factor (such as follistatin, periostin, WISE, and/or Wnt10b).

In yet another embodiment, cells, either primary or secondary cells (for example, dermal papilla cells or dermal sheath cells) that are maintained in culture (such as a hanging drop culture), can be transfected, and can subsequently be introduced into a subject. In a further embodiment, the transfected cells can express follistatin, WISE, periostin, or Wnt10b. In further embodiments, transfected cells (such as dermal papilla cells or dermal sheath cells) are aggregated via contacting cells in a hanging drop culture with an effective amount of an enzyme (such as hyaluronidase), wherein a substrate of the enzyme is an extracellular matrix molecule (for example, hyaluronan). In other embodiments, transfected dermal papilla cells or dermal sheath cells expressing a protein of interest (for example, follistatin, WISE, periostin, or Wnt10b) are aggregated via contacting cells in a hanging drop culture with an effective amount of an enzyme (such as hyaluronidase), wherein a substrate of the enzyme is an extracellular matrix molecule (for example, hyaluronan).

"Subcutaneous" administration can refer to administration just beneath the skin (i.e., beneath the dermis). Generally, the subcutaneous tissue is a layer of fat and connective tissue that houses larger blood vessels and nerves. The size of this layer varies throughout the body and from person to person. The interface between the subcutaneous and muscle layers can be encompassed by subcutaneous administration.

This mode of administration may be feasible where the subcutaneous layer is sufficiently thin so that the factors present in the compositions can migrate or diffuse from the locus of administration and contact the hair follicle cells responsible for hair formation. Thus, where intradermal administration is contemplated, the bolus of composition administered is localized proximate to the subcutaneous layer.

Administration of the cell aggregates (such as DP or DS aggregates) is not restricted to a single route, but may encompass administration by multiple routes. For instance, exemplary administrations by multiple routes include, among others, a combination of intradermal and intramuscular administration, or intradermal and subcutaneous administration. Multiple administrations may be sequential or concurrent. Other modes of application by multiple routes will be apparent to the skilled artisan.

In other embodiments, this implantation method will be a one-time treatment for some subjects. In further embodiments of the invention, multiple cell therapy implantations will be required. In some embodiments, the cells used for implantation will generally be subject-specific genetically engineered cells. In another embodiment, cells obtained from a different species or another individual of the same species can be used. Thus, using such cells may require administering an immunosuppressant to prevent rejection of the implanted cells. Such methods have also been described in United States Patent Application Publication 2004/0057937 and PCT application publication WO 2001/32840, and are hereby incorporated by reference.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods may be utilized to obtain similar results.

Example 1

CD44 is a Wnt Target Gene in the Hair Follicle

Wnt signaling has been shown to be required for hair follicle induction. CD44 has been suggested to be a Wnt responsive gene in the intestinal epithelium (Kuhnert F, et al., *Proc Natl Acad Sci USA*, 2004, 101(1):266-71), though definitive proof of this is lacking. The blockade of hair follicle morphogenesis by inhibition of Wnt signaling can lead to complete absence of any follicular structures, suggesting that a Wnt-responsive cascade of events in the dermis may be involved. Experiments will be performed to show that CD44 is a bona fide Wnt responsive gene in the hair follicle. Experiments will also be performed to show that the regulation of CD44 by Wnt is either direct or indirect; these experiments will be performed using promoter-reporter assays, in particular, assays specifically assessing components of the Wnt pathway.

Example 2

The Mechanism of HA Disappearance in the Hair Follicle Dermis

CD44 internalization of hyaluronan is the main mechanism utilized in bone condensation during development. Microarray analysis has shown evidence of increased CD44 expression in the dermis just prior to hair follicle formation, as well as a marked decrease in HA in the developing hair follicle dermis (see Table 3). Expression of CD44 in the developing hair follicle dermis and its purported role in internalizing HA will be assessed.

Table 3. Microarray data of up-regulated gene expression in DP cells as compared to DS cells (Not averaged).

| Up in DP cells | Fold change |
| --- | --- |
| Follistatin | 74, 56, 223, 104 |
| Follistatin-like 1 FSTL1 | 12, 56, 7, 6, 6, 2, 2, 7, 6 |
| Transcribed locus | 23, 137, 104 |
| USAG-1/WISE | 79, 20, 9, 156 |
| Periostin | 128, 39, 74 |
| Osteonectin/SPARC | 3, 12, 8, 10, 2, 11, 11, 9, 8, 2, 27, 4, 3, 3, 2 |
| Versican | 21, 104, 42, 48 |
| Fibronectin 1 | 42, 74, 4, 3, 9, 14, 9, 2 |
| Fibromodulin | 39, 7, 14, 12, 13 |
| Procollagen C-proteinase enhancer protein (PCPE1 or PCOLCE1) | 9, 39, 16 |
| Defender against cell death 1 | 11, 13, 7, 3, 3, 9, 6, 4, 3 |
| Protein Phosphatase 1, 1A (ppp1R1A) regulatory (inhibitor) subunit | 69, 56, 222, 78 |
| Allograft inflammatory factor 1 (AIF1) | 28, 5, 5 |
| ID1 | 9, 7 |
| ID3 | 5, 18, 17, 13, 8, 7 |
| ID2 | 17, 6, 5, 8, 2, 8, 8, 7 |
| IGFBP2 | 3, 3, 34, 39, 12, 13, 8 |
| IGFBP3 | 22, 32, 10, 13, 8 |
| IGF1 | 11, 7.4 |
| IGF2 | 4 |
| FGFR1 | 22, 6 |
| FGF7/KGF | 13 |
| BMP4 | 15 |
| TGFbeta 3 | 18 |
| Thymosin beta 4 | 12, 13, 2, 3 |
| Thymosin beta 10 | 6, 2 |
| Embigin | 34, 5, 3, 14, 5, 4, 3 |
| Basigin | 5, 5 |
| Syndecan 1 | 11, 5, 5, 2 |
| Syndecan 2 | 32, 17 |
| Syndecan 4 | 6, 3 |
| Biglycan | 6, 6 |
| Glypican 3 | 3, 20 |
| Alkaline phosphatase | 9 |
| Hyaluronidase 2 | 3 |
| Hydroxysteroid (17-beta) dehydrogenase 4 | 8, 11, 18 |
| Hydroxysteroid (11-beta) dehydrogenase 1 | 6 |
| Steroid 5 alpha reductase 1 | 5 |
| ODC antizyme 1 | 7, 6, 2, 22, 5, 4, 4, 4, 3 |

Example 3

Gene Expression Profiling in Hair Follicle Morphogenesis

A method of investigating gene expression leading up to and during early follicle morphogenesis in mouse skin was devised via splitting the dermal and epidermal compartments prior to microarray analysis. One particularly interesting set of genes emerged from a microarray analyses that was performed on intact skin, which were previously masked due to their expression in both compartments.

For example, CD44 is a cell surface glycoprotein that is widely expressed in many tissues in a common 80 kD form. Epidermal keratinocytes, however, express a markedly different 180 kD form (also known as epican). Likewise, the two different enzymes encoding hyaluronan synthase in the skin (HAS2 and HAS3) display differential expression within the dermis and epidermis, respectively. Taken together with previous studies in the literature showing only sporadic time points, our microarray analysis provides a comprehensive temporal and spatial snapshot of differential gene expression in the dermis and epidermis at 12 hour intervals.

Expression CD44, Hyaluronan and its Synthases in Developing Skin

As shown in the microarray experiments, many of the genes involved in CD44-HA turnover are present in mouse skin at the time of hair follicle formation (see Table 3). The spatiotemporal appearance of the corresponding proteins was further defined. The 90 kD form of CD44 is first expressed in the dermal condensate beneath developing hair follicles at e14.5 (see FIG. 30), and Underhill C B, *J Invest Dermatol*, 1993, 101(6):820-6). Its expression increases slightly at e15.5 and then declines until it is not visible at birth. The epidermis shows weak staining of the 180 kD form of CD44 that remains relatively low as compared to the dermis throughout mouse gestation, but which increases dramatically within the epidermis at later times. Thus, the CD44s is expressed at the right time and place to play a role in the removal of HA from the condensing dermal cells.

Figure 2:
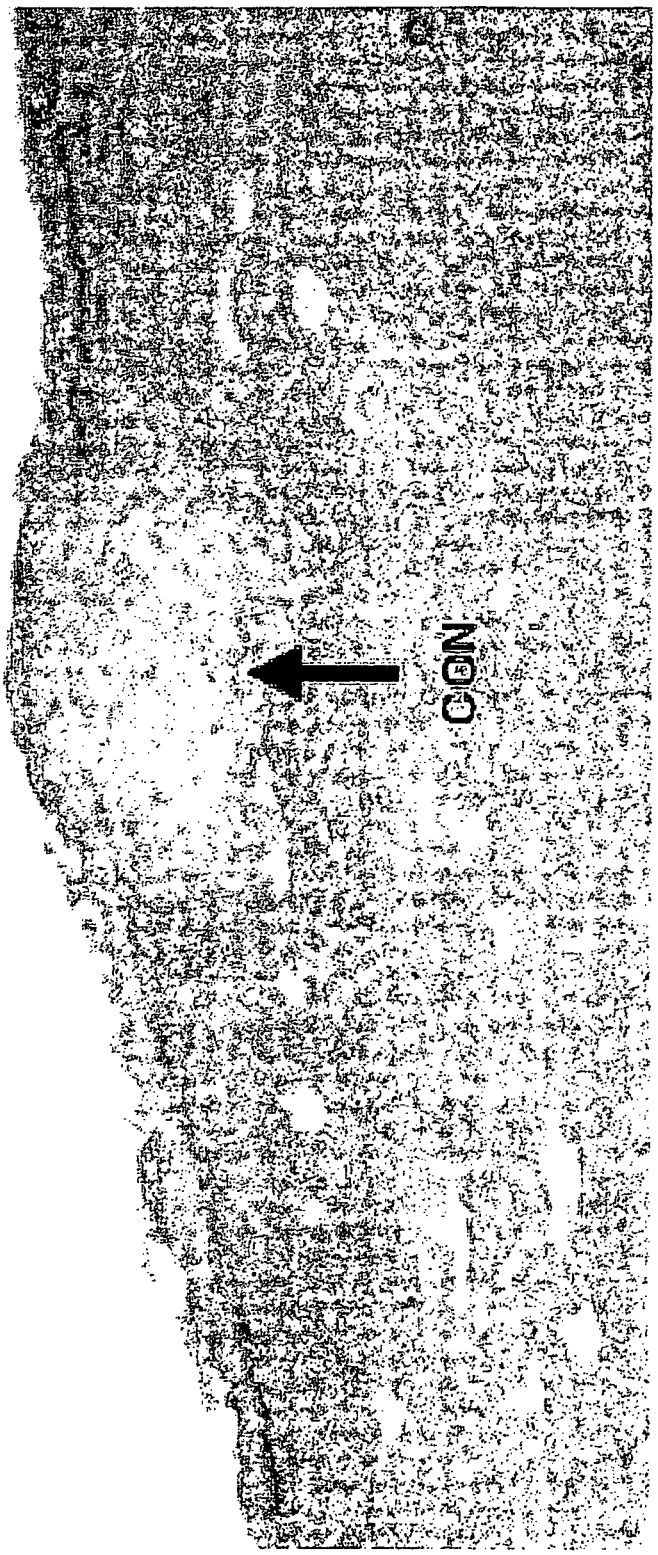
FIG. 2 is a light microscopy image depicting Alcian blue staining (in the presence of $MgCl_2$ treatment) utilized to monitor glycosaminoglycans (GAGS) in the developing hair follicle. The disappearance of certain GAGs (like hyaluronan) in the dermal condensate is represented by the "whited-out" area. CON, dermal condensate.
Figure 3:
FIG. 3 is a light microscopy image depicting Alcian blue staining utilized to monitor glycosaminoglycans (GAGS) in the developing hair follicle. DP, dermal papilla.
Figure 29:
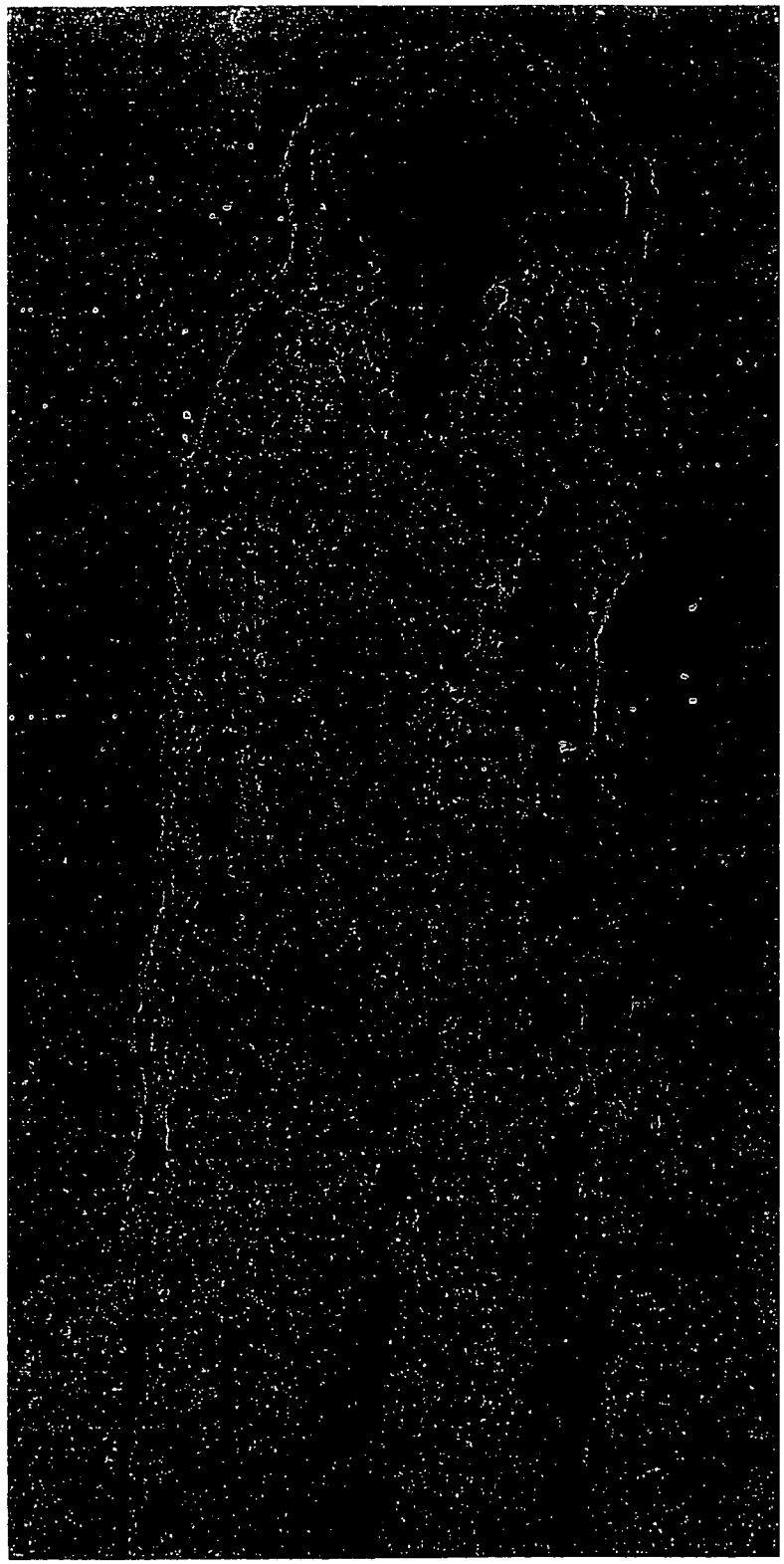
FIG. 29 is a photographic representation of a hair follicle cross section subjected to either Alcian blue staining to visualize GAGs (FIG. 29A) or DAB staining to localize Hyaluronan Binding Protein (HABP) specific regions (seen as brown staining) (FIG. 29B).
Figure 29B:
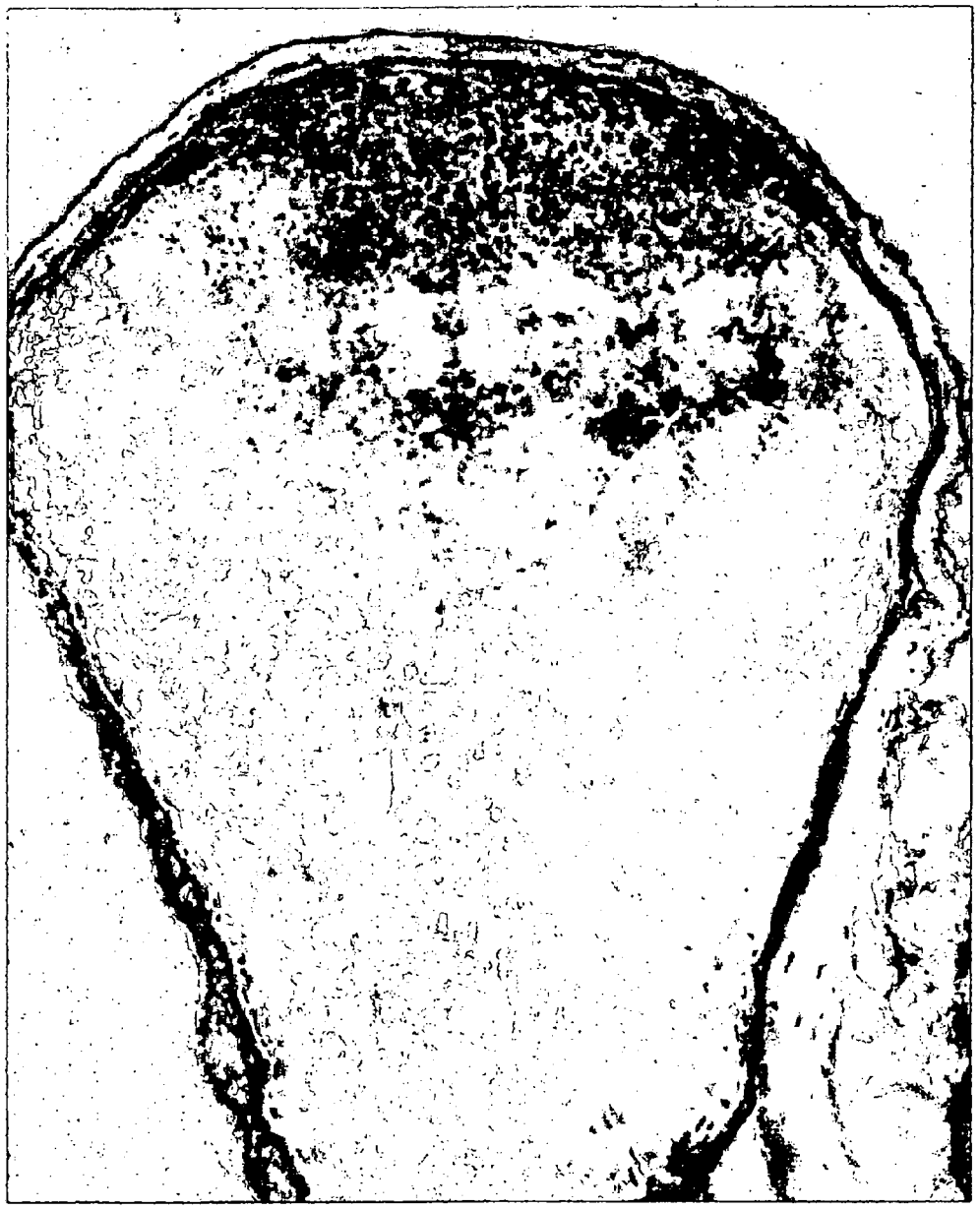

A concomitant diminution in the expression of HA or related surrogate proteins is expected on the basis of the experiments presented. HA itself was assayed using an antibody against HABP, a hyaluronic acid binding protein. A striking reduction in HABP staining was noted within the region of the developing hair follicle as compared to interfollicular regions (FIG. 29A and FIG. 29B, respectively). Similarly, Alcian blue staining was utilized to monitor glycosaminoglycans in the developing hair follicle (FIG. 1), and a marked reduction in HA was observed in addition to lightly sulphated glycosaminoglycans using $MgCl_2$ concentration and lowering the pH (see FIGS. 2-3). The disappearance of certain GAGS (like hyaluronan) in the dermal condensate is represented by the "whited-out" area where HA is disappearing, perhaps by CD44 (compare FIG. 1 with FIG. 2, in the absence and presence of magnesium, respectively). In addition, the later stage image of hair follicle development demonstrates a decreased GAG concentration in the epithelial compartment (FIG. 3). Taken together, expression studies not only confirm the result of the microarray analysis, but also place CD44 and HA at precisely the correct temporal and spatial locations to plan a central role in mediating dermal condensation.

Detailed methods for microarray experiments and analysis have previously been described (O'Shaughnessy R F, et al., *J Invest Dermatol*, 2004), and are hereby incorporated by reference. Tables 1 and 2 list relevant genes that may be important in aggregating dermal papilla cells or dermal sheath cells grown in a hanging drop culture (O'Shaughnessy R F, et al., *J Invest Dermatol*, 2004).

Example 4

Perturbations in CD44-HA Pathway can Disrupt Condensation

Mouse mutations have been generated that have targeted mutations in several components of the CD44-HA pathway. CD44 mutant animals have no overt phenotype presumably due to compensation for CD44 by other cell surface receptors. However, targeted ablation of two of the hyaluronan synthases have been reported, which shed light on their role during development. HAS2 is the predominant isoform of HAS expressed in the body. Knockout of HAS2 is lethal during e9.5 at the time migration of the cardiac cushion into the cardiac jelly, a process mediated by epithelial-mesenchymal transition (EMT). HAS3−/− animals are viable and fertile, but show phenotypes in the hair follicle (Spicer A P, et al., *Glycoconj J*, 2002, 19(4-5):341-5).

Interestingly, the converse approach also led to a perturbation in condensation. It has been found the onset of condensation can be delayed experimentally manipulating chondrocyte cultures to maintain HAS expression through the normal time of condensation, leading to sustained biosynthesis of HA past the time it should be internalized and degraded by CD44.

A whole skin organ culture model will be used to determine whether this mechanism is also required for hair follicle dermal condensation. Proficiency in using this model is demonstrated below in which hair follicle formation can be completely inhibited using EGF as previously shown (Kashiwagi M, et al., *Dev Biol*, 1997, 189(1):22-32). CD44 will be blocked using neutralizing antibodies, and HAS2 expression will be knocked down using short hairpin RNA (shRNA) or will be inhibited by adding glucocorticoids to the culture medium.

One mouse model exists that exhibits an enhanced capacity for hair follicle condensations with each subsequent hair cycle—the constitutively active β-catenin mouse. Likewise, the Dkk1-K14 transgenic mouse exhibits a complete blockade of Wnt signaling, and no hair follicle structures whatsoever. Organ cultures from these mutants' skin will be used to ask whether the CD44-HA mechanism is active in a Wnt-potentiated and/or Wnt-inhibited environment.

Example 5

Treatment of Whiskerpad Mesenchyme with Hyaluronidase Results in Condensation

Freshly dissected intact DP, from both human and rat, have been shown to induce a new hair follicle when implanted into the ear wound assay, as can low-passage cultured rat DP. Cultured human DP cells, on the other hand, have never successfully been used to induce a new hair using in vivo assays. The main reason for this failure of human cultured DP to induce is believed to be due to their inability to form a condensation upon introduction into the wound. Instead, human DP cells behave as if they are in a wound-healing environment, and migrate away from the implantation site.

Several different means of enhancing the ability of human cultured DP to undergo aggregation, condensation and hair follicle neogenesis will be tested. In a previous study, Underhill (*J Invest Dermatol* 1993, 101:820-26) sought to determine whether condensation of mesenchymal cells during hair follicle development was dependent on localized degradation of hyaluronan. To do this, cheek pads of d12.5 mouse embryos were dissected and cultured in the presence and absence of *Streptomyces* hyaluronidase, an enzyme that specifically degrades HA. Treatment of mouse whiskerpad organ culture with hyaluronidase resulted in decrease of the spacing between mesenchymal cells, and a general condensation of the mesenchyme. This study provides supporting evidence that this mechanism may be conserved in hair follicle development, yet stops short of asking the key functional question of whether the condensed cells had enhanced inductive capabilities.

In addition to enzymatic treatment with hyaluronidase to enhance aggregation, this approach will be combined with three-dimensional hanging drop cultivation of DP cells. Human DP cells grown in non-adherent conditions have been demonstrated to take on many of the properties of an intact DP upon self-aggregation in the droplet. Addition of different growth factors to the culture media will be assessed to determine if the factors can further enhance the inductive properties of human cultured DP cells. Among these factors are Wnt10b, shown in the literature to enhance inductive capacity, as well as periostin, a gene we identified from germinative epithelial cells, which enhance inductiveness when co-cultured with rat DP cells.

Example 6

A New Model of Dermal Papilla Cell Culture

Human follicular dermal papilla (DP) cells grown in culture have been studied. They are of particular interest since they retain their inductive capabilities during early passages. However, some key differences between DP cell behavior in vivo and in culture have been identified; for example smooth muscles a actin (αSMA) is a sheath-cell specific marker in vivo, but once in culture both papilla and sheath cells express αSMA. Furthermore, culture cells derived from anagen DP's are highly proliferative whilst the same cells in vivo do not proliferate. Proteoglycans play a prominent role in tissue remodeling and their function in the hair follicle is no exception. They have an important role during the hair cycle through cell-cell and cell-matrix interactions and as mediators of cell signaling. The expression of proteoglycans in the DP varies with the stages of the hair cycle. The chondroitin sulphate proteoglycan, Bamacan, is cycle specific with expression in anagen being lost on entry to catagen and throughout telogen. Expression of Syndecan-1, a heparan sulphate proteoglycan is present in anagen DP as well as during morphogenesis. In contrast the expression of the heparan sulphate proteoglycan, Perlecan, remains constant throughout the hair cycle.

This example demonstrates that DP cells can be grown in suspension culture in tiny volumes, forming small spheroids that appear morphologically to be more akin to the dermal papilla cells found in vivo. Differences between two culture conditions for growing DP cells using the expression profile of αSMA, proteoglycans and markers of proliferation are described.

General Rat DP and DS Cell Culture Methods:

Dermal papillae (DP) were dissected from adult rat vibrissa follicles using previously described methods (Jahoda C A and RF Oliver, *Br J Dermatol*, 1981, 105:623-27; PCT Publication WO2005/05911929). Briefly, the mystacial pad was cut open, the skin was inverted, and the end bulb region of isolated sinus follicles was removed. Fine forceps were then used to invert the collagen capsule of the end bulb and expose the papilla and epithelial matrix. The matrix component was then removed, and any epithelial tissue still present on the papilla was teased off. The papilla was then extracted using fine forceps and transferred to a culture vessel.

Dissected papillae were cultured initially in 20% foetal bovine serum (Seralab) and Eagles minimal essential medium (E-MEM) with Glutamax-I, Earles salts and 25 mM Hepes (Invitrogen) containing Gentamycin (50, µg/ml). Cell cultures were initiated in 35 mm dishes (Falcon) and were continued in these vessels after the first passage. On the second passage the cells were transferred to 25 cm$^2$ flasks (Falcon). After the first passage the concentration of fetal bovine serum in the medium was reduced to 10%. Dermal sheath (DS) tissue was isolated from vibrissae follicles as described (Reynolds A J, 1989, from Ph.D. Thesis: *in vivo and in vitro studies of isolated and interacting dermal and epidermal components of the integument*). During the DP dissection above, when the follicle end bulb was inverted the DS collapsed but remained attached to the base of the DP. It was then teased from the papilla using fine forceps, and pieces of DS tissue from several follicles were initially cultured in exactly the same manner described for DP cells above.

Preparation of Dermal Papilla and Dermal Sheath Cell Clones:

Dermal papilla and dermal sheath tissue was obtained by microdissection from the vibrissa follicles of 3 month old female Wistar rats as described above. Individual explants were cultured in 24 well plates (Nunc) in MEM+10% FBS supplemented with antibiotics (Sigma) containing 20% DP or DS primary culture conditioned medium (MEM+CM). Primary cultures were incubated at 37° C./5% CO$_2$ for 5 days to allow cells to grow out from the explant while limiting the amount of cell division. Cells from individual explants were collected by incubation with 0.25% trypsin for 5 minutes at 37° C., and cloned at a density of one cell per well in 96 well plates by limiting dilution. Wells containing single cells were identified after 24 hours by phase contrast microscopy, and these were cultured in MEM+CM for 28 days, with a medium change every 7 days. Cultures were routinely passaged every 21-35 days.

Human DP cells between Passages 3 and 5 were trypsinized and either plated in 35 mm dishes of 50,000 cells or placed in hanging drops containing 3000 cells. All cells were cultured in MEM containing 10% FBS and were harvested after 30 hours in culture. Characterization of and comparisons between the two culture methods were carried out using real time RT-PCR and immuno-cytochemistry. The integrity and viability of the spheres was confirmed using TEM and viability markers.

Results:

Perlecan and Syndecan 1 expression was similar in both flat cells and dermal cell spheres. However, Bamacan expression was reduced in dermal spheres. αSMA was expressed in cultured cells but expression was lost in dermal spheres. Cell proliferation was demonstrated in cultured cells but cells in the spheres were minimally proliferative as indicated by reduced expression of Ki67 and PCNA.

Conclusions:

The hanging drop cultured cells showed a different profile from normally cultured dermal papilla cells, and the spheres resembled a telogen-like state.

Example 7

Human DP "Balls" Implanted into Amputated Hair Follicles

Preparing Cells to Make Aggregates.

DP cells were first washed while in their T25 flask and subsequently trypsinized within the flask. Media containing 10% FBS was added to the cells to stop trypsinisation and were then centrifuged at 1000 rpm for 5 minutes. After the excess media was poured off, the pellet of cells was washed with serum free/antibiotic free media in order to remove any remaining trypsin and was centrifuged at 1000 rpm for 5 minutes. After the excess media was poured off, the pellet of cells was resuspended in 1 ml of dMEM media containing 10% FBS. Cells were counted using a haemocytometer to count cells. Cells were diluted to 300 cells/µl by adding dMEM media containing 10% FBS.

Aggregate Formation.

Figure 5:
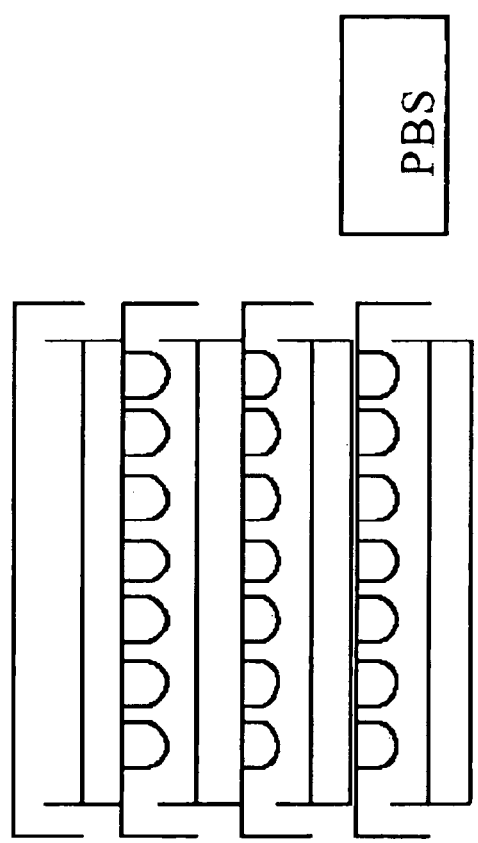
FIG. 5 is a schematic representation of hanging drop cultures after inversion.

DP cell aggregates ("balls") were generated by pipetting 10 µl drops of cells onto the top of an inverted Petri dish lid, approximately 0.7 cm apart, to give ~3000 cells per drop (See FIG. 4). After the base of the Petri dish was filled with PBS, the lid was subsequently turned over (smoothly and quickly), and placed down on base (see FIG. 5). This process was repeated for an additional 2 plates in order to make a stack of plates containing DP balls. A final Petri dish with no DP balls but filled with PBS was placed on top of the stack (FIG. 5). The dishes were incubated at 37° C. for 30 hours in order to generate single balls comprising dermal papilla (DP) cells.

This method can also be carried out to generate aggregates of dermal sheath cells.

Amputated Hair Follicles.

Figure 6:
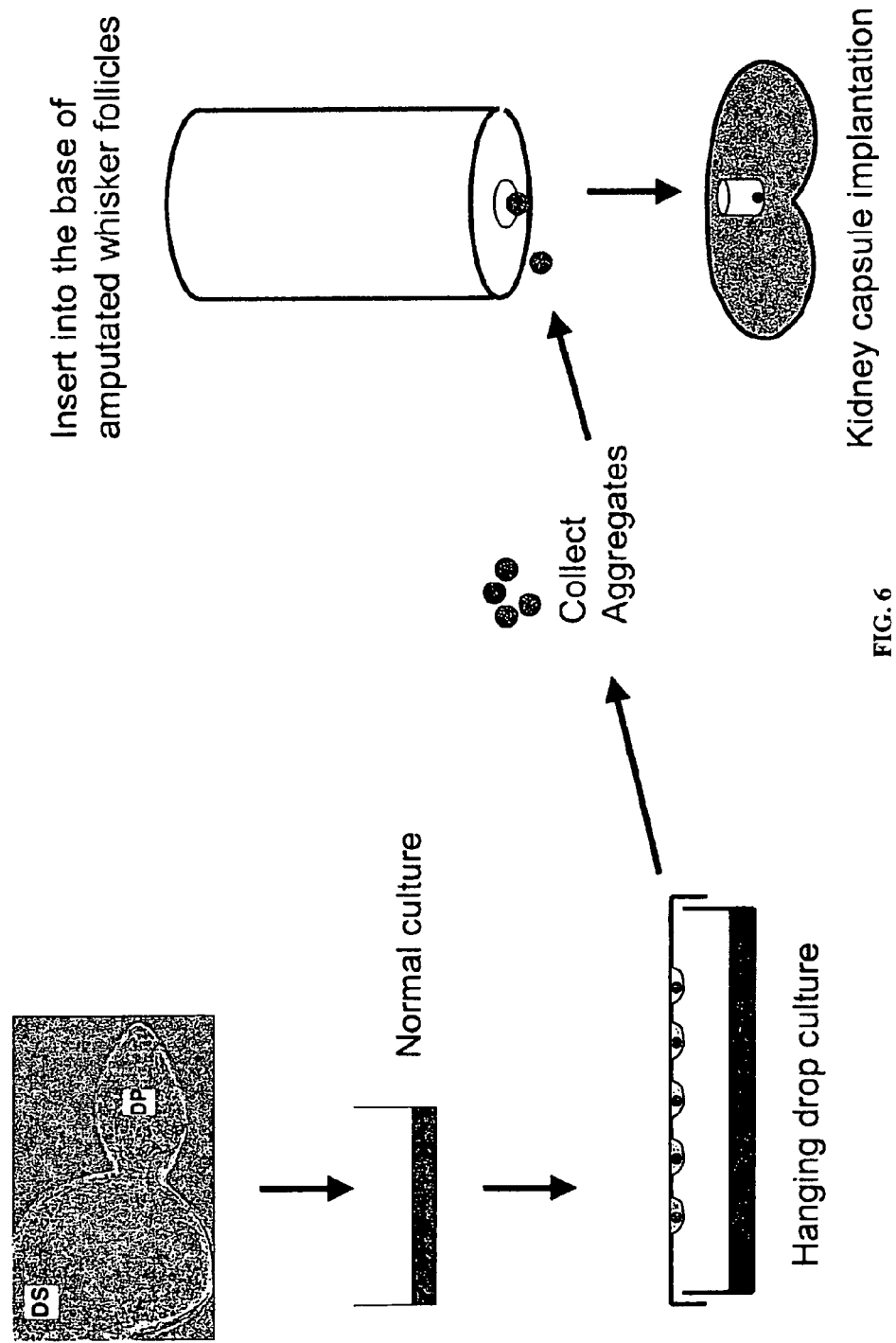
FIG. 6 is a flow diagram of kidney capsule implantation of human DP aggregates inserted into amputated follicles.
Figure 7:
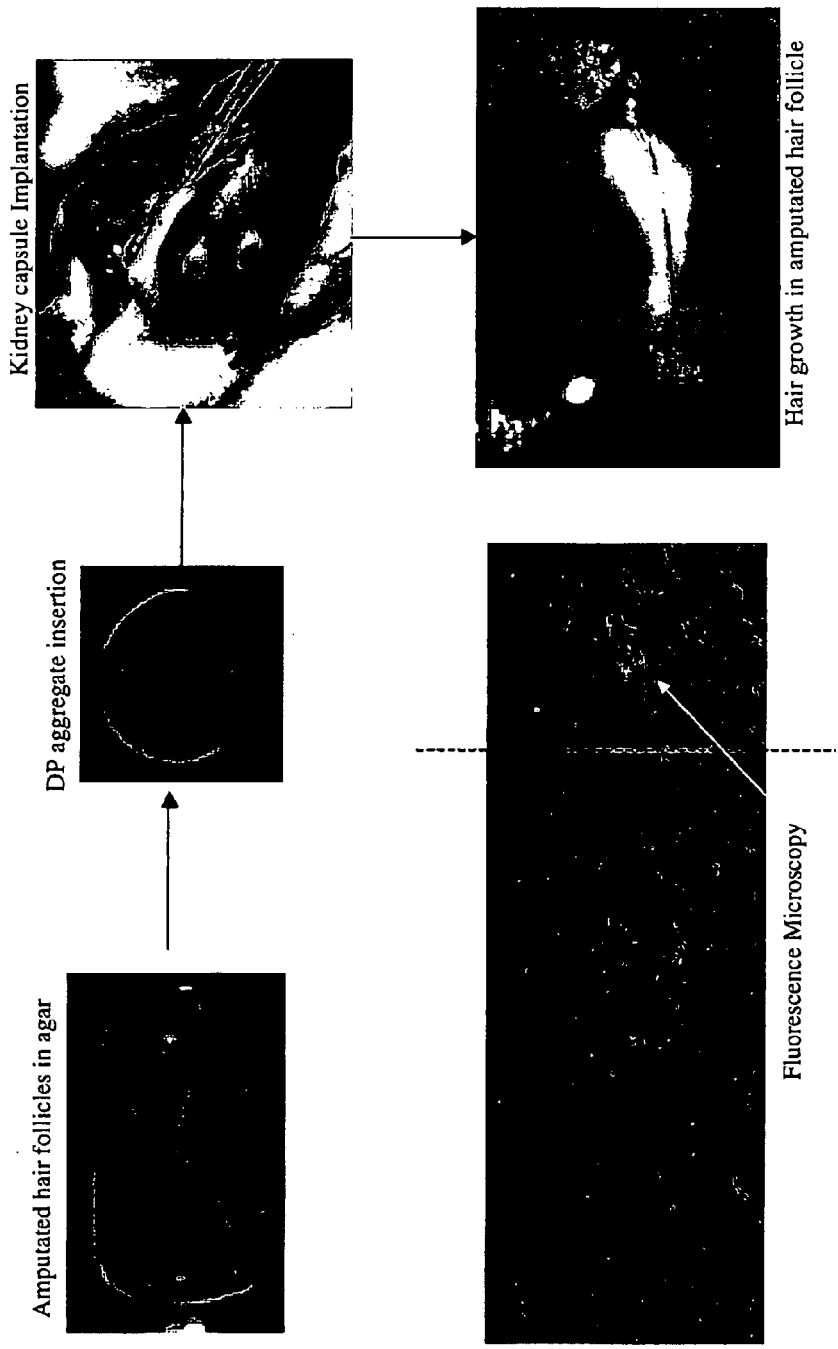
FIG. 7 is a photographic representation of kidney capsule implantation of human DP aggregates ("balls") that were inserted into amputated follicles.

Rat vibrissa follicles were dissected out of a rat facepad, were washed with MEM media, and were subsequently placed onto agar. The end bulb was removed at the point above the nerve and was then pushed into the Gey's agar, upper follicle first. The balls (described above) were removed from the culture dish and placed in a drop of MEM media. One DP ball was then placed against the outer root sheath, which was subsequently implanted under the kidney capsule of nude mice (see schematics depicted in FIG. 6 and FIG. 7). Samples were then removed and photographed, and subsequently sectioned for microscopy analysis (such as H&E staining (Cat# SS007: Biogenex, San Ramon, Calif.); immunohistochemistry such as DAB staining (Molecular Probes, *The Handbook: A Guide to Fluorescent Probes and Labelling Technologies*, 10$^{th}$ edition (Invitrogen Corp., CA); and immunofluorescence microscopy (Molecular Probes, *The Handbook: A Guide to Fluorescent Probes and Labelling Technologies*, 10$^{th}$ edition (Invitrogen Corp., CA)).

Results.

Figure 8:
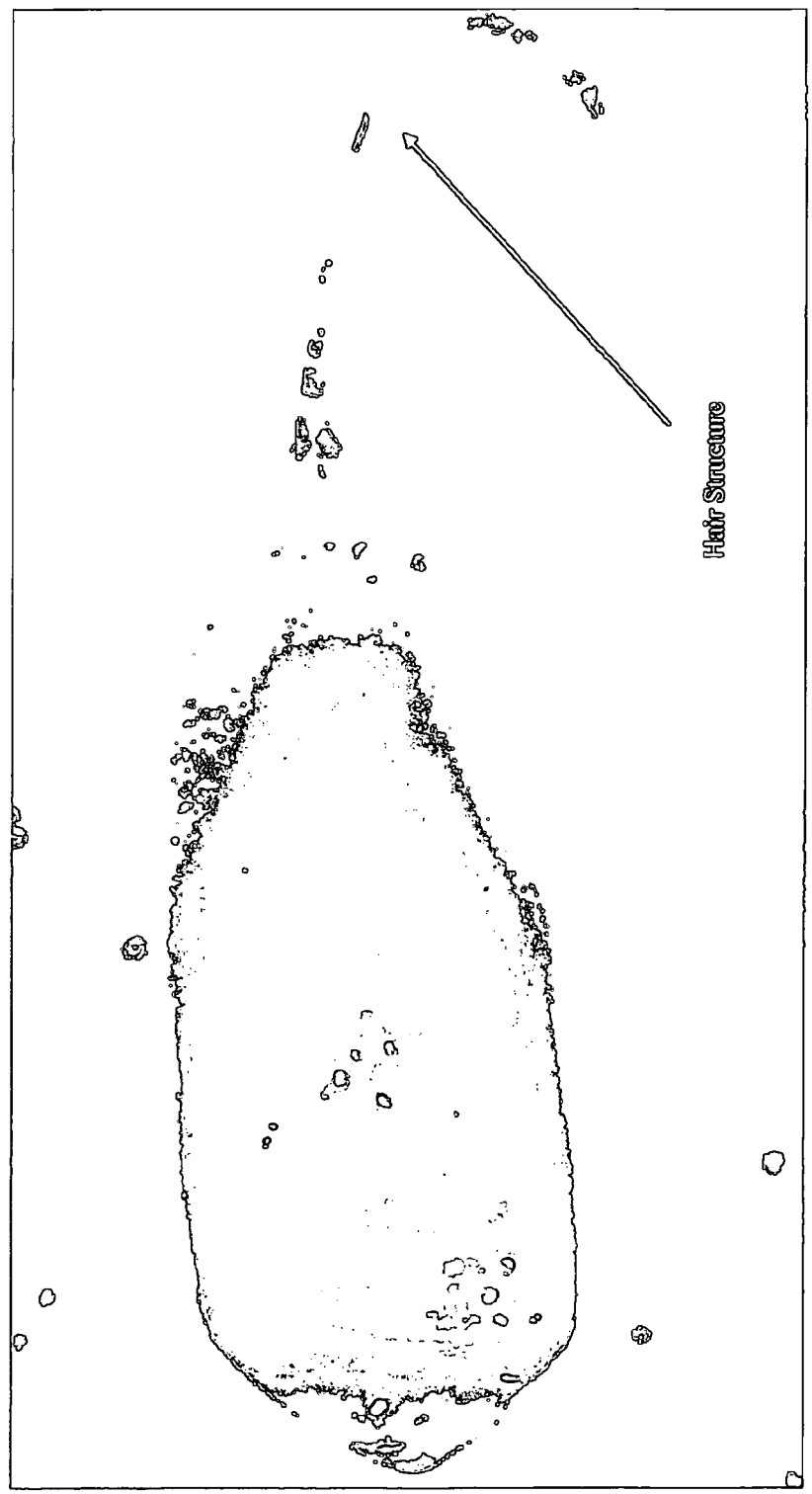
FIG. 8 is a photographic image depicting hair induction following kidney capsule implantation of DP aggregates ("balls") that were inserted into amputated follicles. The white arrow points to a hair structure.
Figure 9:
FIG. 9 is a photographic image of hair induction following kidney capsule implantation of DP aggregates ("balls") that were inserted into amputated follicles. The black arrows point to hair structures.
Figure 10:
FIG. 10 is a photographic image depicting hair induction following kidney capsule implantation of human DP aggregates ("balls") that were inserted into amputated follicles. The white arrow points to a hair structure.
Figure 11A:
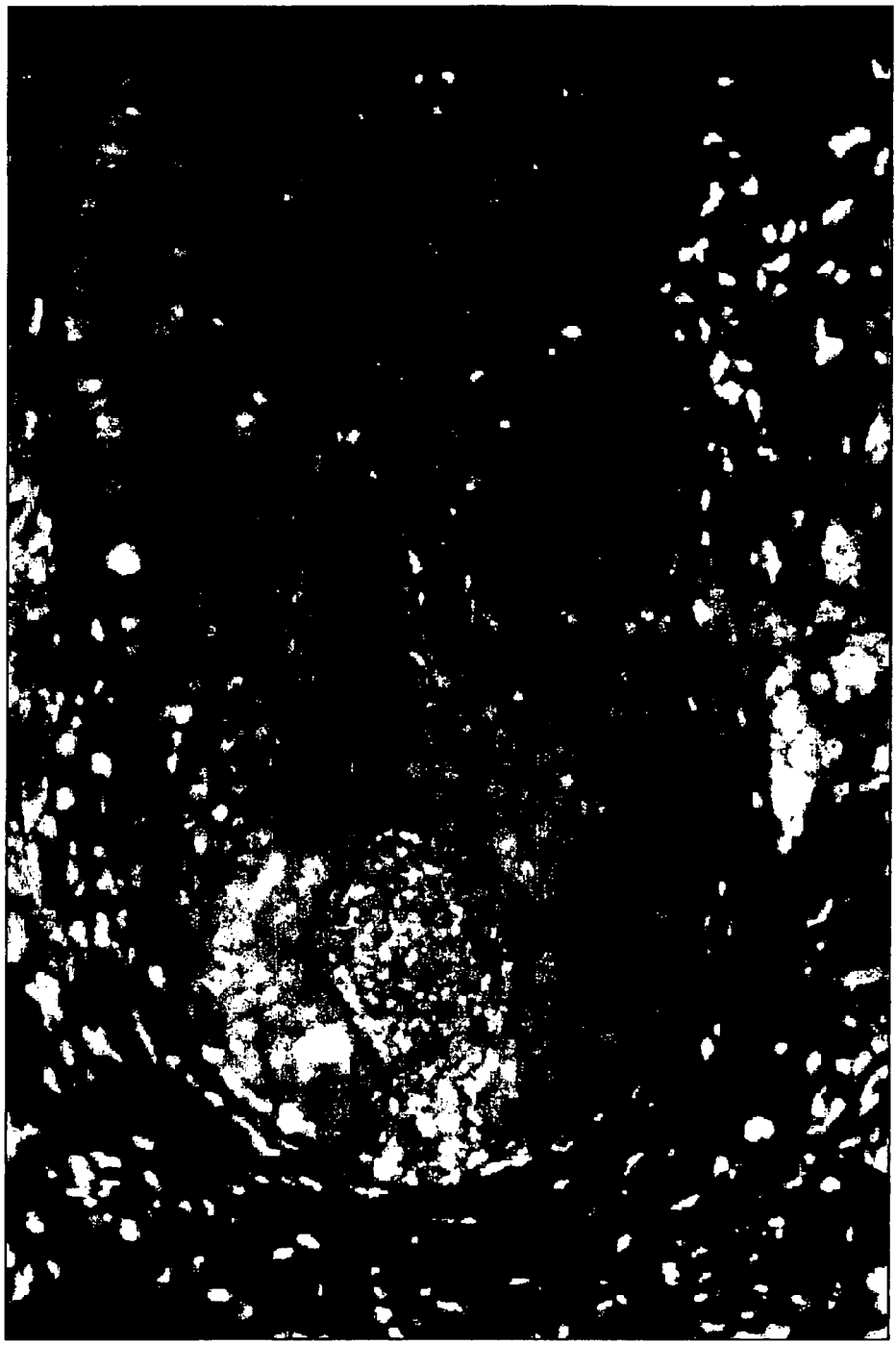
FIG. 11A is a immunohistochemical image of new dermal papilla cells stained with an antibody directed to versican (red).
Figure 11B:
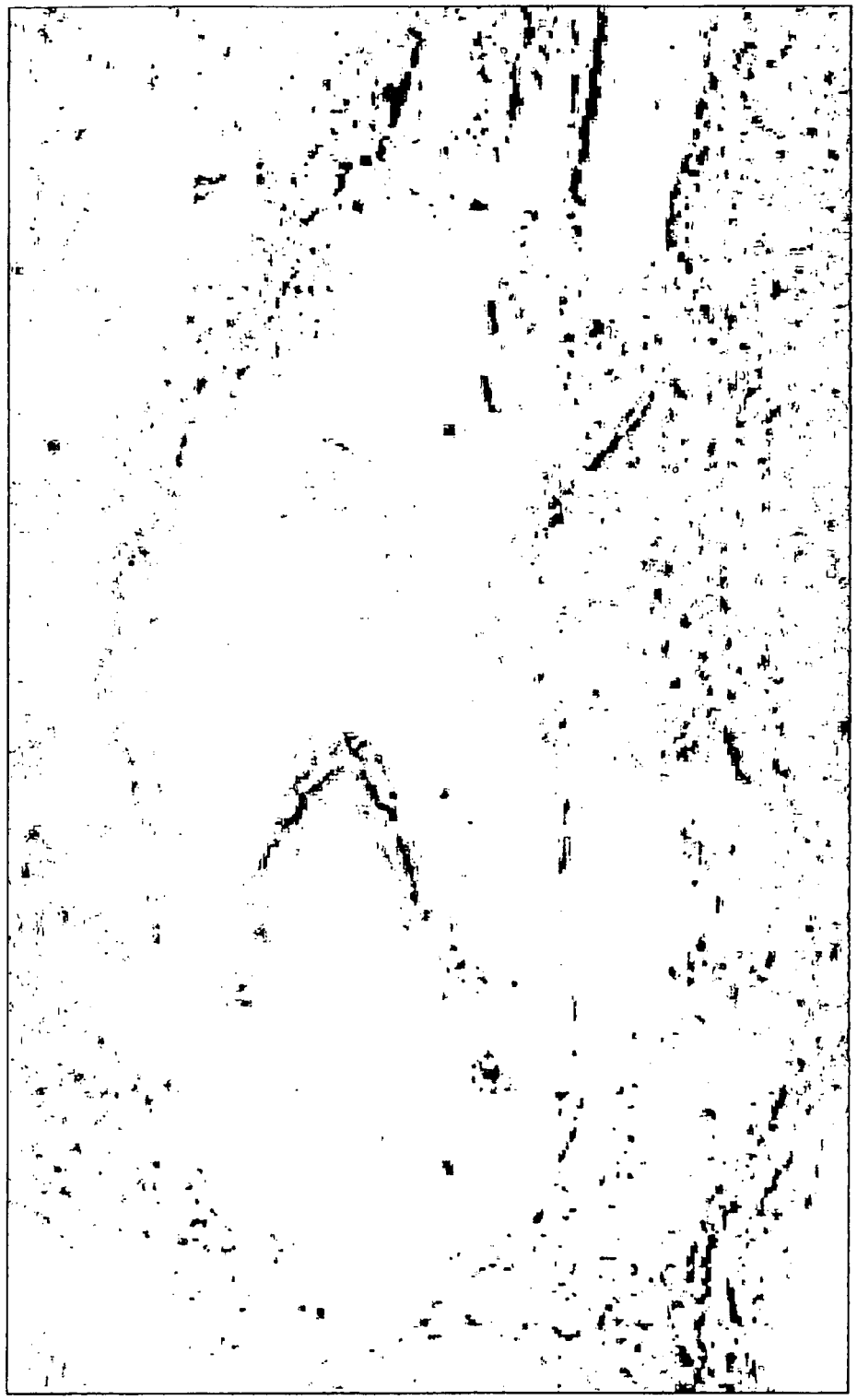
FIG. 11B depicts the phase-contrast image of the sectioned hair follicle.

Adult human DP aggregates induced new hair growth in amputated hair follicles (see FIGS. 8-10). In the sectioned follicle, new dermal papilla cells were stained with an antibody to versican (red). Versican is a large chondroitin sulfate proteoglycan and results here showed that anagen DP cells indeed maintain specific versican expression (FIG. 11). These DP cells also maintained hair inductive activity in culture wherein previous studies have shown that, without stimulation from epithelial cells, DP cells lose this inductivity during passages in culture. As a positive control, large black fibres are observed from rat DP cells implanted into a hair follicle (FIG. 12).

Example 8

Human DP "Balls" Implanted into the Epithelium of a Footpad

Preparing Cells to Make Aggregates.

DP cells were first washed while in their T25 flask and subsequently trypsinized within the flask. Media containing 10% FBS was added to the cells to stop trypsinization and were then centrifuged at 1000 rpm for 5 minutes. After the excess media was poured off, the pellet of cells was washed with serum free/antibiotic free media in order to remove any remaining trypsin and was centrifuged at 1000 rpm for 5 minutes. After the excess media was poured off, the pellet of cells was resuspended in 1 ml of dMEM media containing 10% FBS. Cells were counted using a haemocytometer to count cells. Cells were diluted to 300 cells/µl by adding dMEM media containing 10% FBS.

Aggregate Formation.

DP cell aggregates ("balls") were generated by pipetting 10 µl drops of cells onto the top of an inverted Petri dish lid, approximately 0.7 cm apart, to give ~3000 cells per drop (See FIG. 4). After the base of the Petri dish was filled with PBS, the lid was subsequently turned over (smoothly and quickly), and placed down on base (see FIG. 5). This process was repeated for an additional 2 plates in order to make a stack of plates containing DP balls. A final Petri dish with no DP balls but filled with PBS was placed on top of the stack (FIG. 5). The dishes were incubated at 37° C. for 30 hours in order to generate single balls comprising dermal papilla (DP) cells.

This method can also be carried out to generate aggregates of dermal sheath cells.

Footpad Epithelium.

Figure 13:
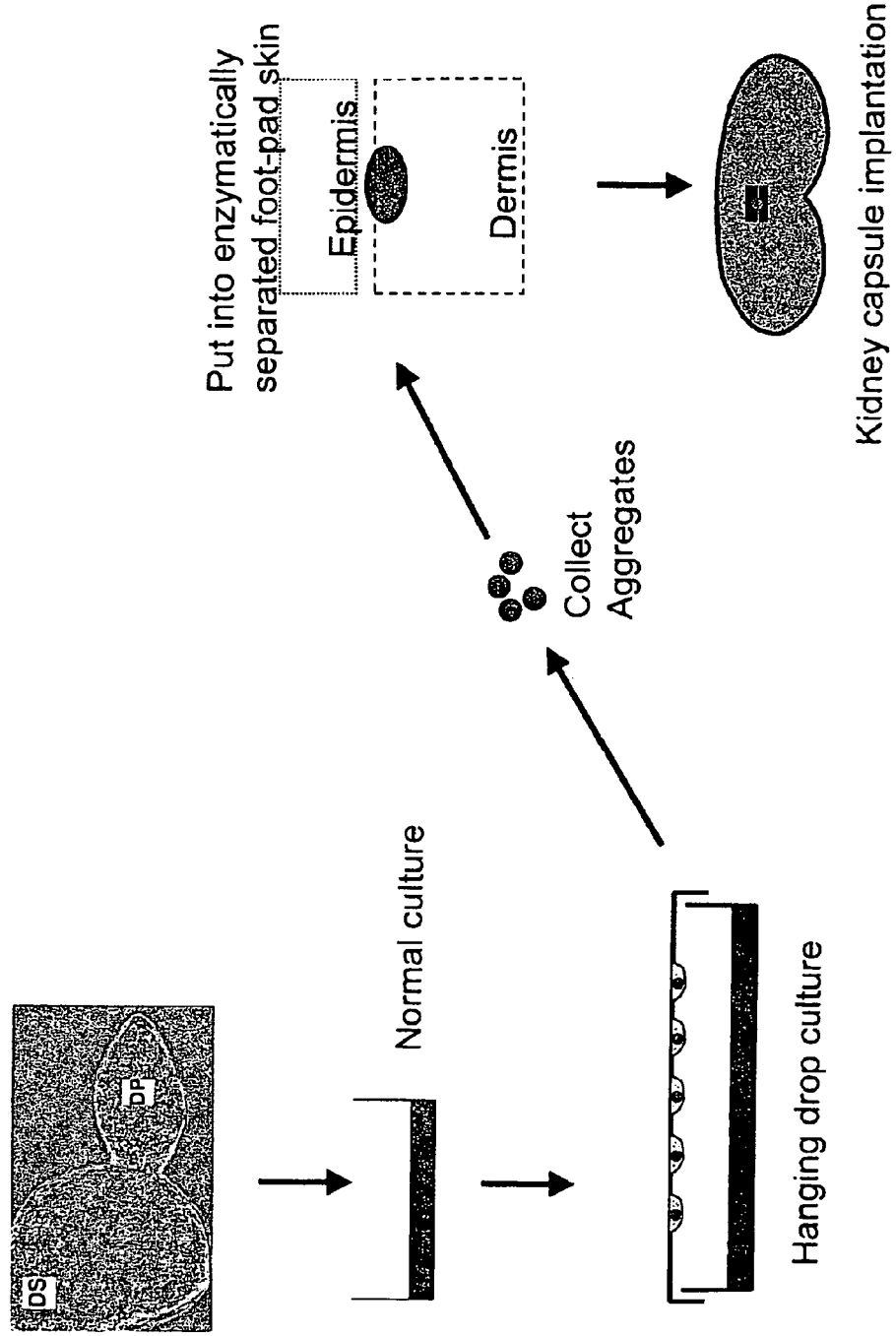
FIG. 13 is a flow diagram of kidney capsule implantation of human DP aggregates inserted into enzymatically separated foot-pad skin.
Figure 14:
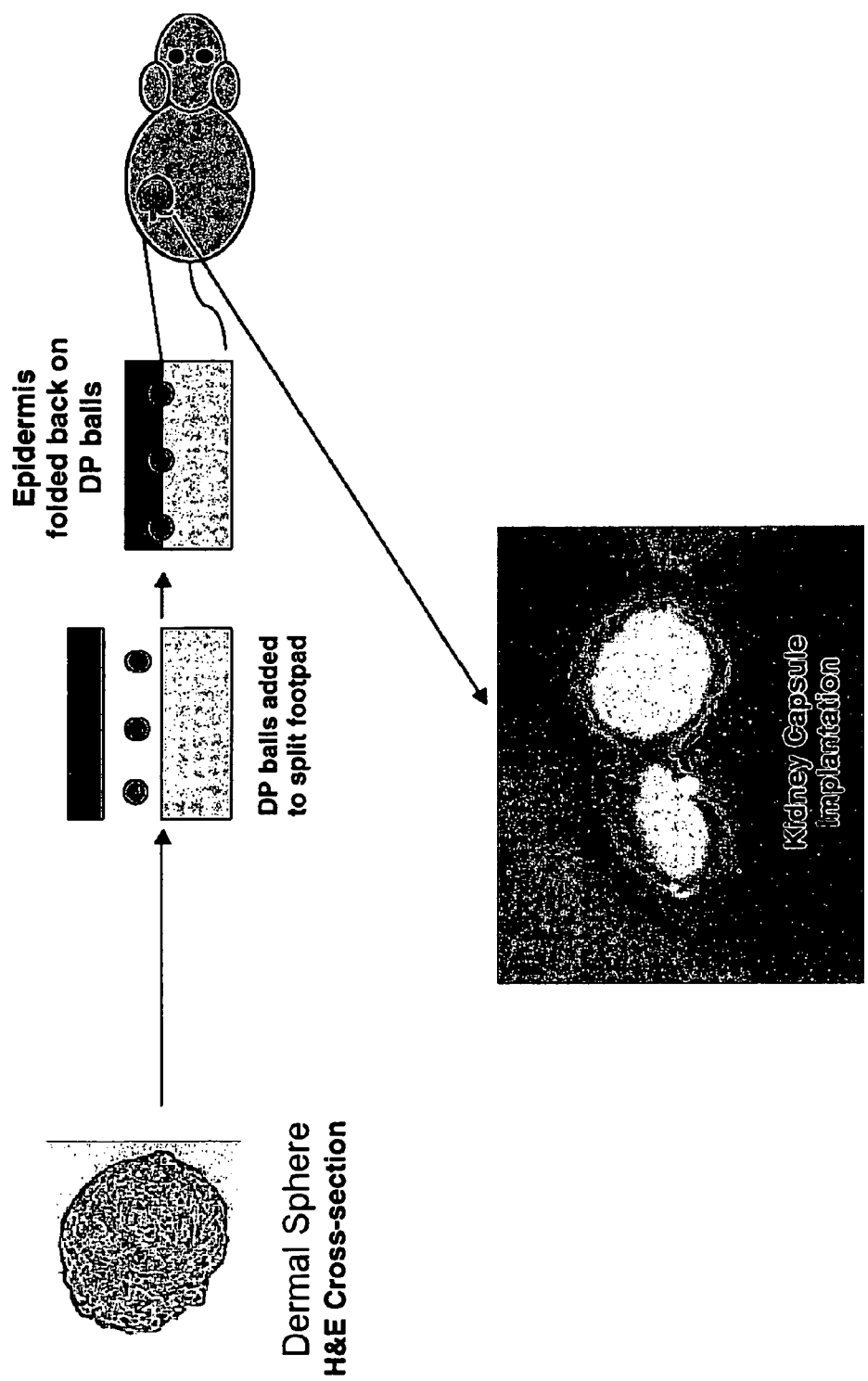
FIG. 14 is a photographic representation of kidney capsule implantation of human DP aggregates ("balls") inserted into enzymatically separated foot-pad skin.

The footpad epidermis and dermis was separated over half the skin using pancreatin and tryspin in Earles MEM medium. This was placed on Gey's agar with the epidermis folded back on itself. DP balls were subsequently removed from culture and placed in a drop of MEM medium. One DP ball at a time was picked up with forceps and placed onto the dermis. Approximately 4-5 DP balls were placed on each skin bit. The epidermis was then folded back to sandwich the DP balls and were subsequently incubated 37° C. for 2 hours. The DP balls were then placed under the kidney capsule of nude mice (see schematics depicted in FIG. 13 and FIG. 14), were removed and photographed, and subsequently sectioned for microscopy analysis (such as H&E staining (Cat# SS007: Biogenex, San Ramon, Calif.); immunohistochemistry such as DAB staining (Molecular Probes, *The Handbook: A Guide to Fluorescent Probes and Labelling Technologies*, 10$^{th}$ edition (Invitrogen Corp., CA); and immunofluorescence microscopy (Molecular Probes, *The Handbook: A Guide to Fluorescent Probes and Labelling Technologies*, 10$^{th}$ edition (Invitrogen Corp., CA)).

Results.

Figure 15:
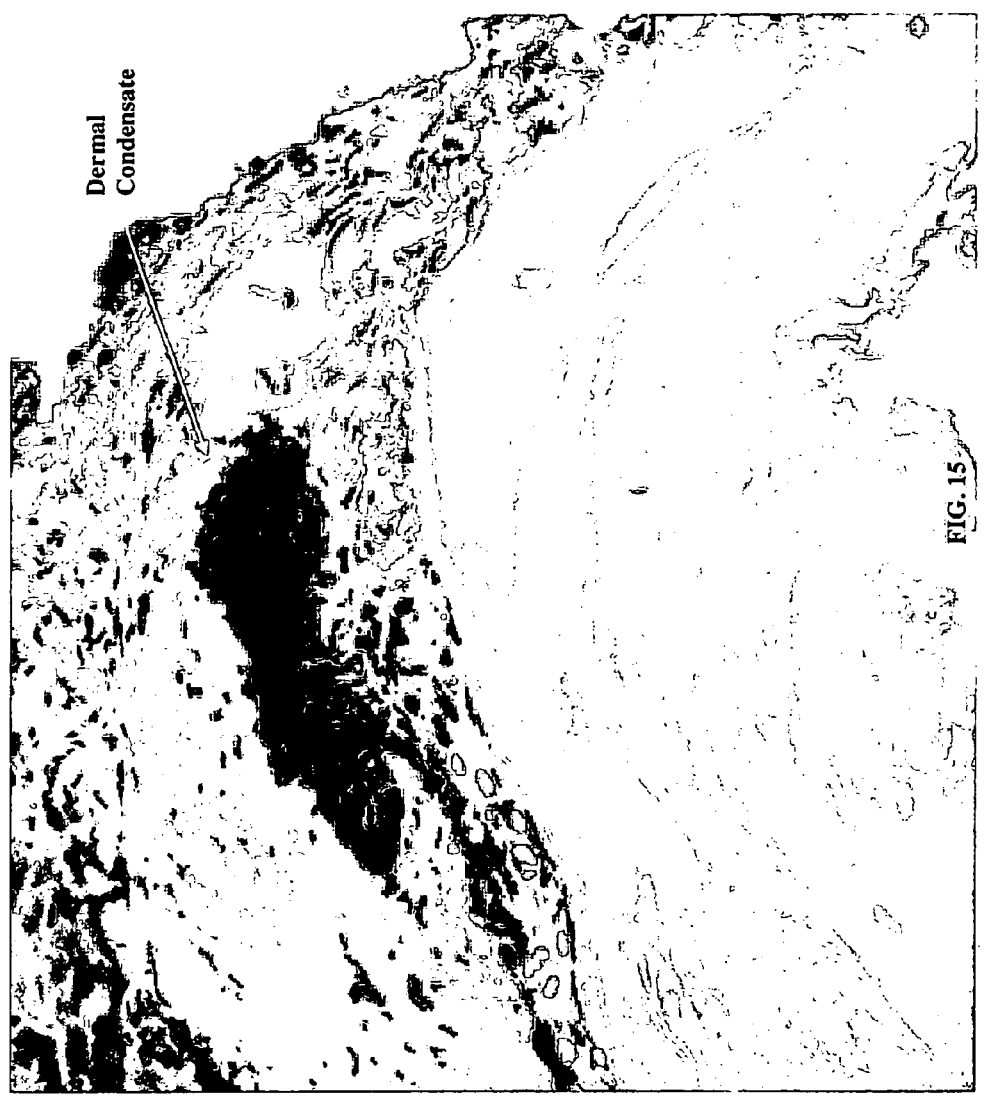
FIG. 15 is a light microscopy image (hematoxylin and eosin staining) depicting a dermal condensate (white arrow) following implantation of a human DP aggregates inserted into enzymatically separated foot-pad skin.
Figure 16:
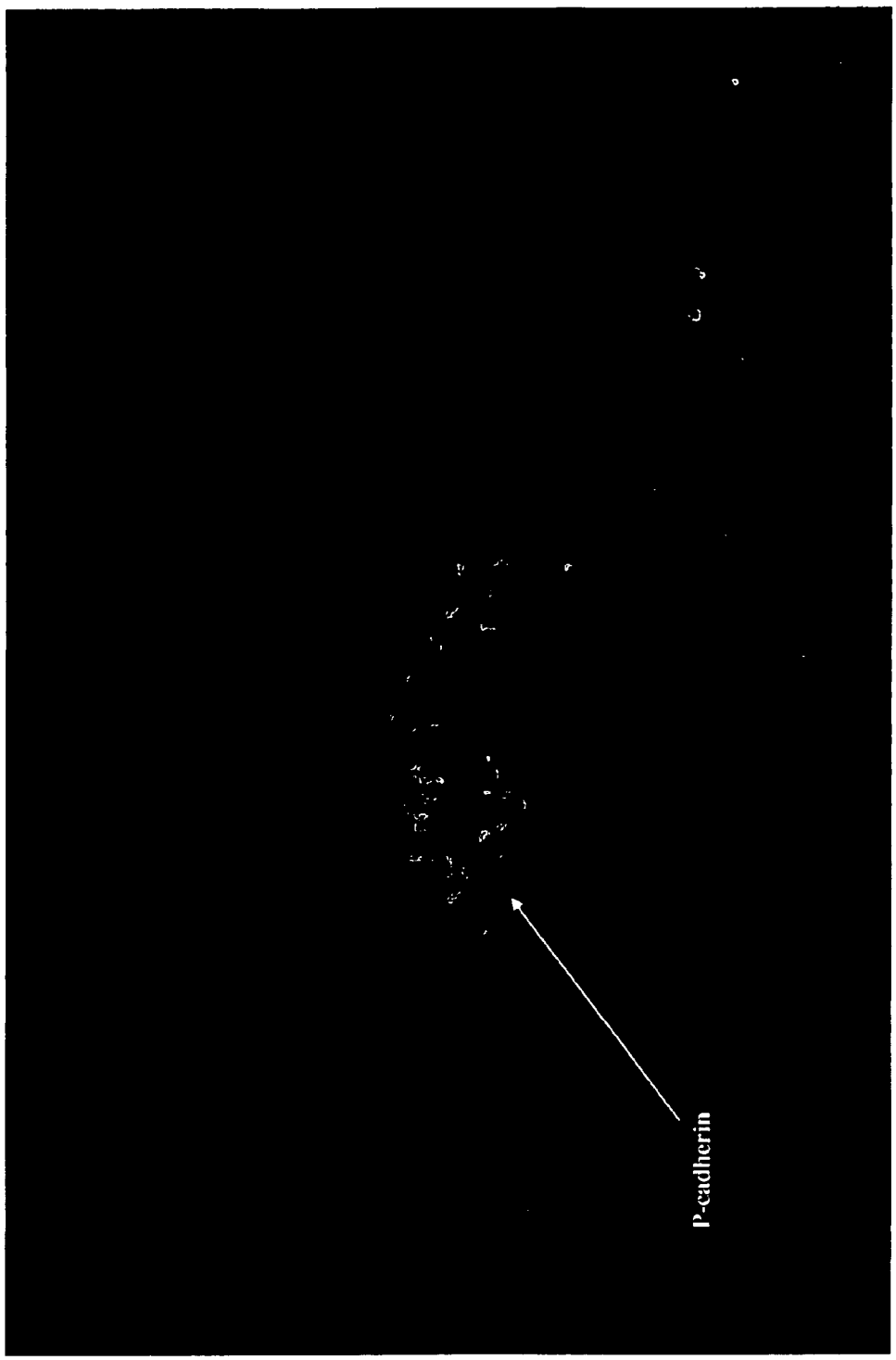
FIG. 16 is an immunofluorescence microscopy image of a sectioned follicle following implantation of a human DP aggregates inserted into enzymatically separated foot-pad skin. Epithelial cells were stained with an antibody directed to P-Cadherin (red), a specific marker for hair follicle epithelium, which surrounds a dermal condensate (unstained).
Figure 17:
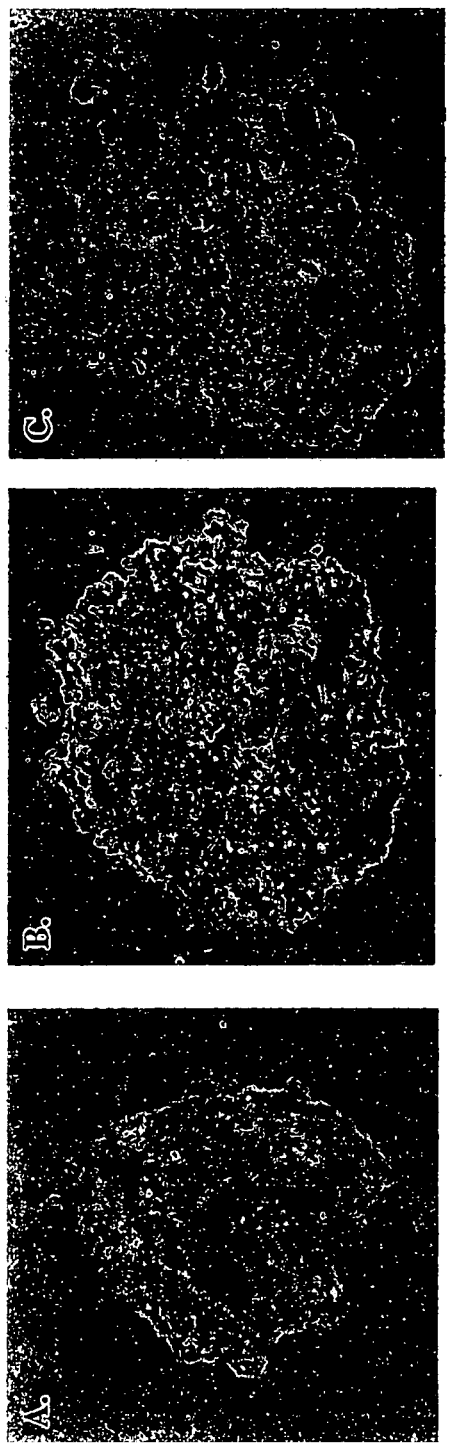
FIG. 17 (panels A-C) are light microscopy images of a sectioned DP "ball" containing DP cells that was inserted into the skin of a footpad and subsequently implanted onto a kidney capsule. Alcian blue staining of a DP aggregate was positive for the presence of GAGs (panel A). DAB staining of a DP aggregate was positive for the presence of hyaluronan (HA) (depicted as brown staining in panel B). Panel C depicts an unstained DP aggregate.

Adult human DP aggregates were observed as dermal condensates (see FIG. 15). In the sectioned follicle, epithelial cells were stained with an antibody directed to P-Cadherin (red), a specific marker for hair follicle epithelium. These cells surround the dermal condensate (represented by lack of P-Cadherin staining seen in FIG. 16), that comprise DP cells. DP cells from the DP ball inserted into the skin of a footpad and subsequently implanted onto a kidney capsule maintained their hair inductive activity while in the absence of surrounding epithelial cells. Alcian blue staining of a DP aggregate was positive for the presence of GAGs (FIG. 17), such as hyaluronan (depicted as brown staining in FIG. 17, middle panel).

Example 9

Microarray Data

To elucidate key dermal signaling pathways during early pelage hair follicle morphogenesis, a combination of microdissection and microarray techniques was used. Skin taken from 12.5 dpc (days post coitus), 13.5 dpc, 14.5 dpc and 15.5 dpc embryos were enzymatically split into separate dermal and epidermal components and global transcription profiling was performed using microarray chips (MOE430A). Data was analyzed using GeneTraffic™ software with the 12.5 dpc embryonic skin as a reference for comparison purposes. Initial inspection of the microarray data highlighted the differential expression of genes in the Sonic, hedgehog, and Wnt pathways, previously identified as key signaling molecules during hair follicle morphogenesis. Further examination of the data identified more novel changes in expression levels of genes involved in Hyalronan synthesis and regulation.

Figure 28:
FIG. 28 represents a light microscopy image of CD44 expression visualized by immunohistochemistry (DAB staining) where CD44 was observed exclusively in the dermal condensation within the dermal compartment (brown staining).
Figure 30:
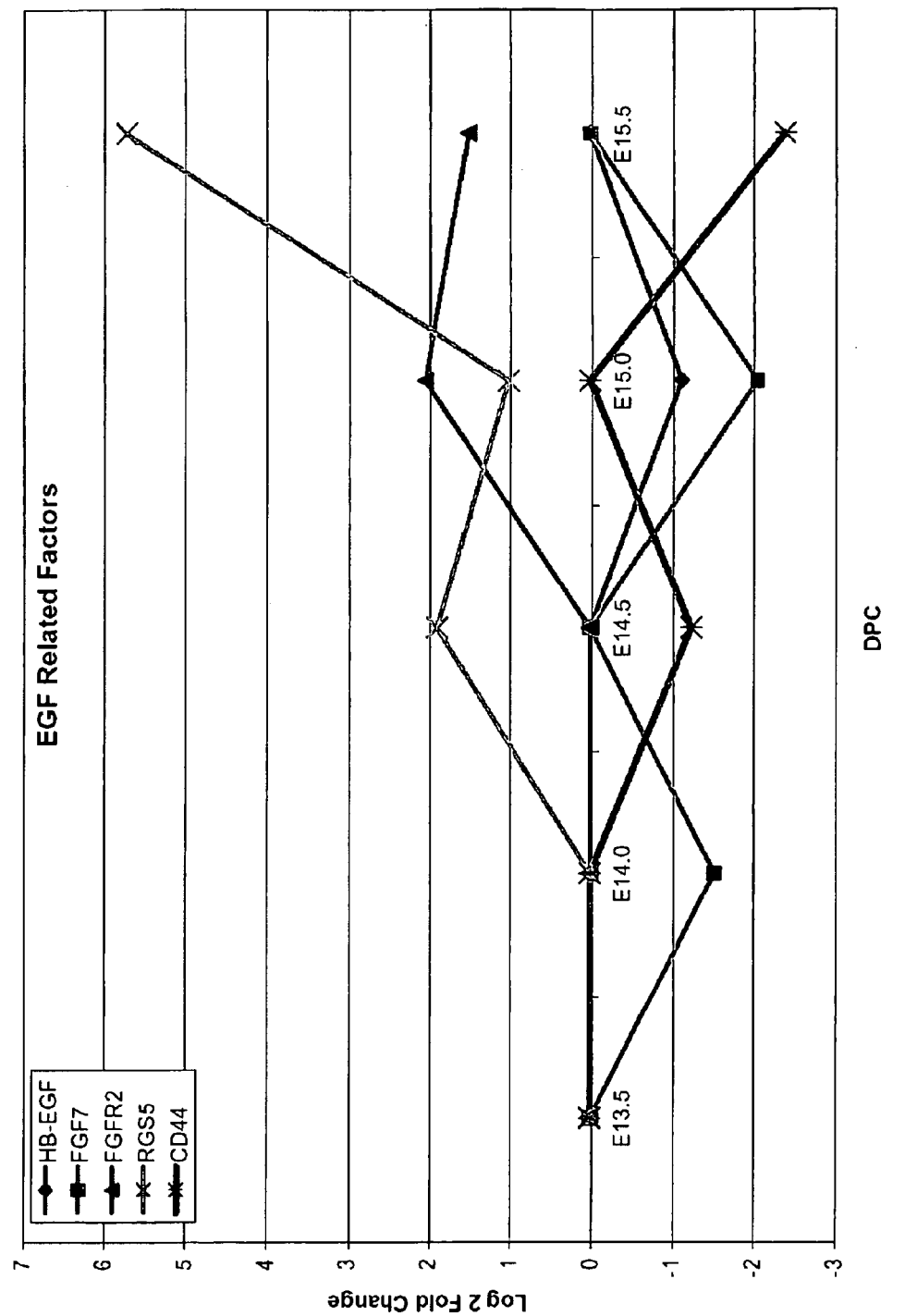
FIG. 30 is a graphical representation depicting EGF factors and CD44 protein expression in the upper differentiating cell layers of the epidermis at various developmental timepoints (days post coitus, dpc).

Hyaluronan and CD44 are Conversely Expressed in the Dermal Condensation During Hair Follicle Morphogenesis The expression of hyaluronan (HA) and CD44 was investigated in pelage follicles of embryonic mouse skin from 13.5 dpc through 16.5 dpc time points, which correspond to the early stages of hair follicle development. Both CD44 and HA showed a dynamic expression pattern within the dermal condensation of the developing hair follicle. Immunohistochemical analysis (DAB staining; Molecular Probes, *The Handbook: A Guide to Fluorescent Probes and Labelling Technologies*, 10$^{th}$ edition (Invitrogen Corp., CA)) revealed CD44 protein expressed in the upper differentiating cell layers of the epidermis at all investigated developmental timepoints examined. Within the dermis, CD44 expression was absent until 14.5 dpc, at which point both the epidermal hair germ and dermal condensation had become visible (FIG. 30). At this developmental stage, CD44 expression was visualized according to methods described by Yu and Toole (*Developmental Dynamics* (1997) 208: 1-10) and was found to be restricted exclusively to the dermal condensation in the dermal compartment (FIG. 28). This localized expression continued through the studied development stages. HA distribution was investigated using a specific high affinity hyaluronan binding protein as previously described (Underhill C B, (1993) *J Invest Dermatol*, 101(6):820-6). At all studied developmental timepoints, HA was found exclusively in the dermis (FIGS. 1-3). Upon formation of the dermal condensation, HA was lost in this structure and remained absent during the early stages of follicle morphogenesis (FIG. 3).

Downregulation of Hyaluronan within the Dermal Condensation is an Evolutionarily Conserved Mechanism Chicken backskin corresponding to early stages of feather morphogenesis (7.5 dpc and 8.5 dpc) was probed using an HA specific probe (staining depicted in red in FIG. 18). Similar to the expression results in mouse skin, HA was expressed uniformly throughout the dermis (before the formation of the dermal condensation (7.5 dpc). Once the dermal condensation was visible however (8.5 dpc), expression was absent in this structure (FIG. 18). This suggests that dermal condensation is a conserved mechanism across multiple species.

Figure 19:
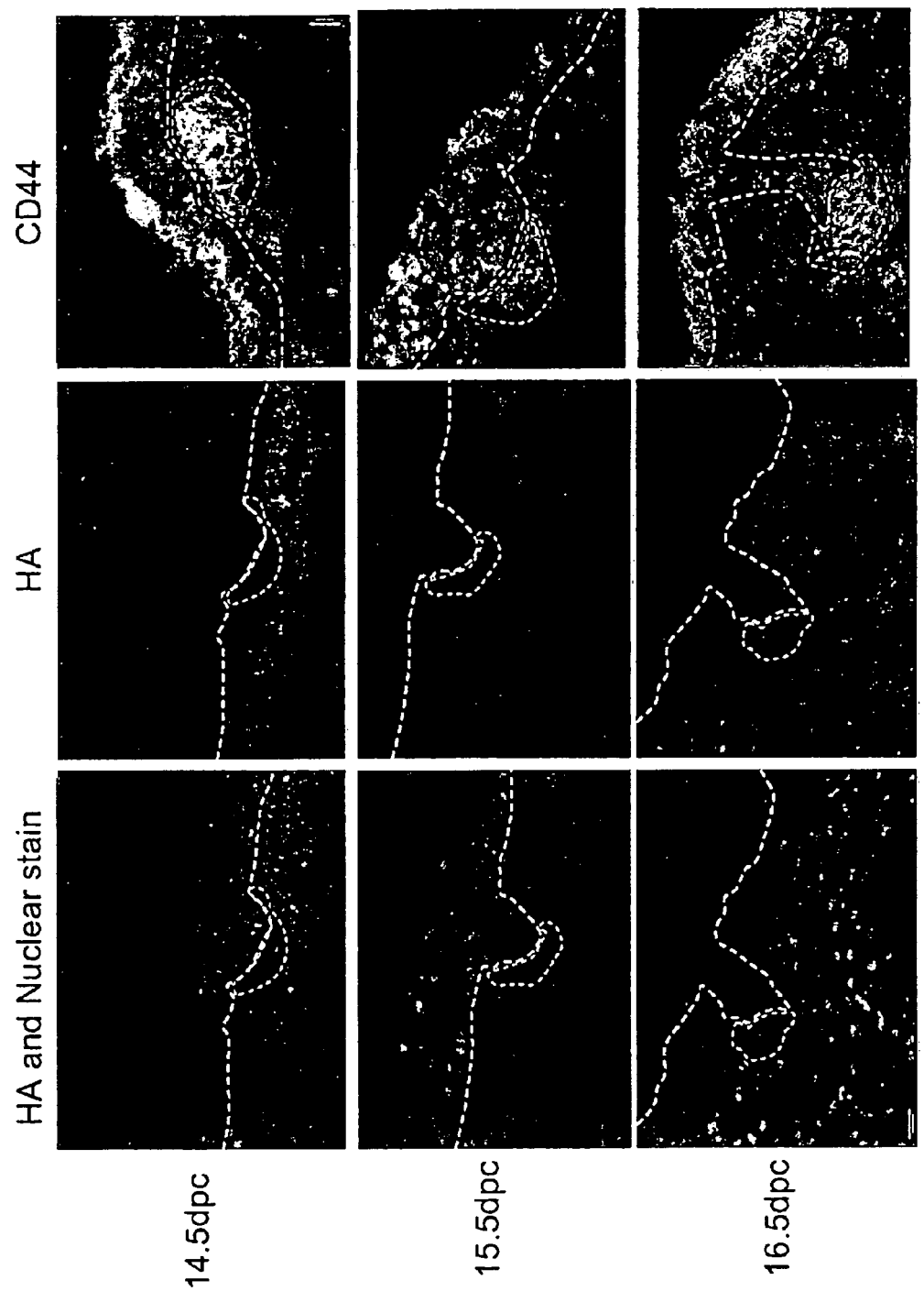
FIG. 19 represents immunofluorescent microscopy images depicting HA and CD44 localization within the epidermis section obtained from cultured embryonic skin. An antibody directed to hyaluronan binding protein (HABP) localized throughout the dermis (red; first and second columns), but was absent from the dermal condensate (hatched crescent shape outline). An antibody directed to CD44 localized to the epidermis and the dermal condensate (green; third column). The hatched line represents the basement membrane (BM), located above the dermal condensate. DAPI staining depicts cellular nuclei (blue).

Hyaluronan and CD44 Expression in Mouse Embryonic Skin Organ Cultures Recapitulates In Vivo Expression in the Mouse To study the effects of HA misexpression in the development of a HF, an embryonic skin organ culture model was utilized. To assess how representative this model was for investigating the role of HA distribution in vivo, the expression of CD44 and HA in the cultured embryonic skin was first investigated. Embryonic skin cultures were established using pre-hair follicle initiation (14.5 dpc) skin and were incubated for 72 hrs. The cultured skin hair placodes became visible after 24 hr in culture. After 72 hr, skins were removed from culture, sectioned, and the expression of both HA and CD44 were assessed (FIG. 19). The dermal condensate was negative for HA staining (red) while expressing CD44 (green). Expression of both proteins in the HF of the cultured backskin was virtually indiscernible from that of 16.5 dpc back skin in vivo (FIG. 19).

Effects of Reduced HA on Hair Follicle Morphogenesis in Embryonic Skin Cultures

Figure 20:
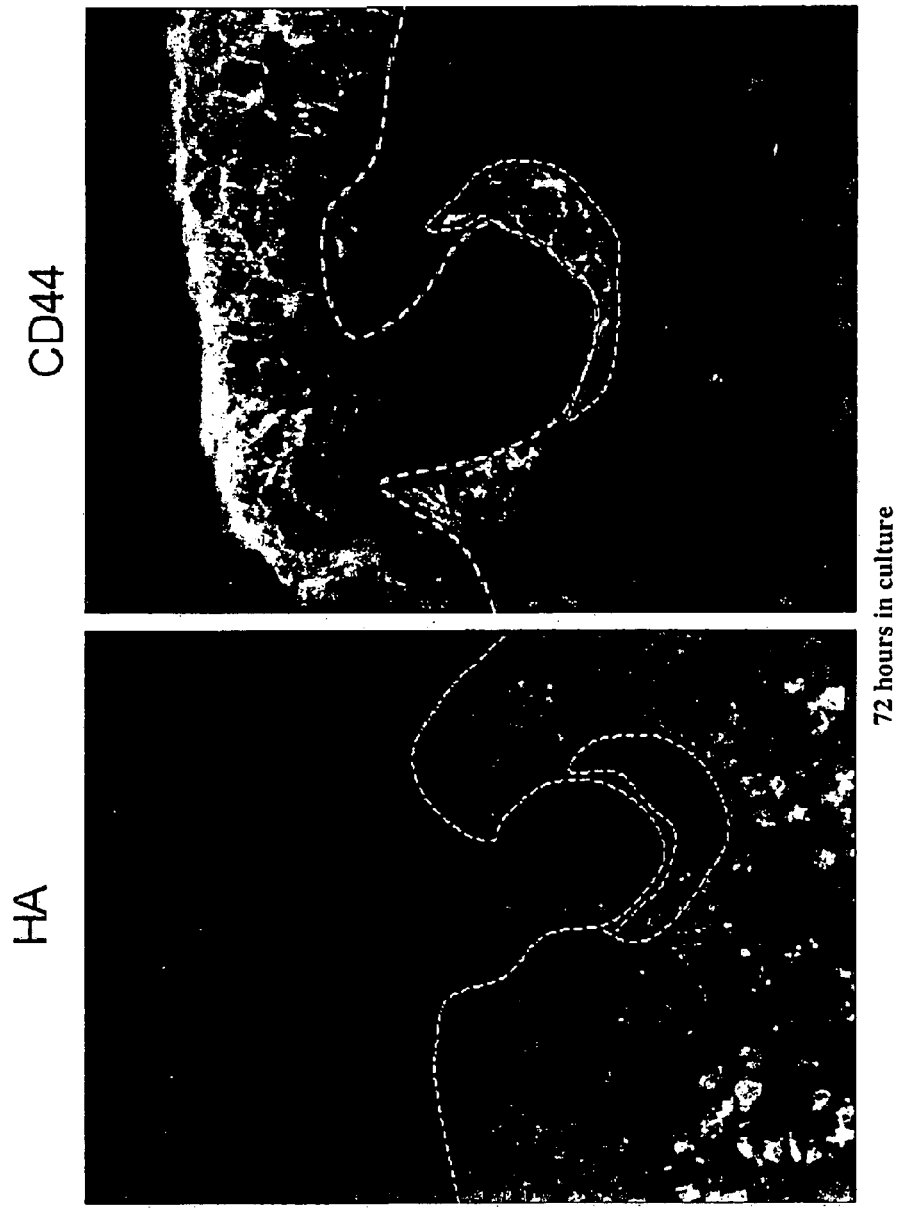
FIG. 20 represents immunofluorescent microscopy images depicting HA (blue, left panel) and CD44 (red, right panel) localization within an epidermis section obtained from 72 hour cultured embryonic skin. The hatched line represents the basement membrane (BM), located above the dermal condensate (hatched crescent shape outline).
Figure 21:
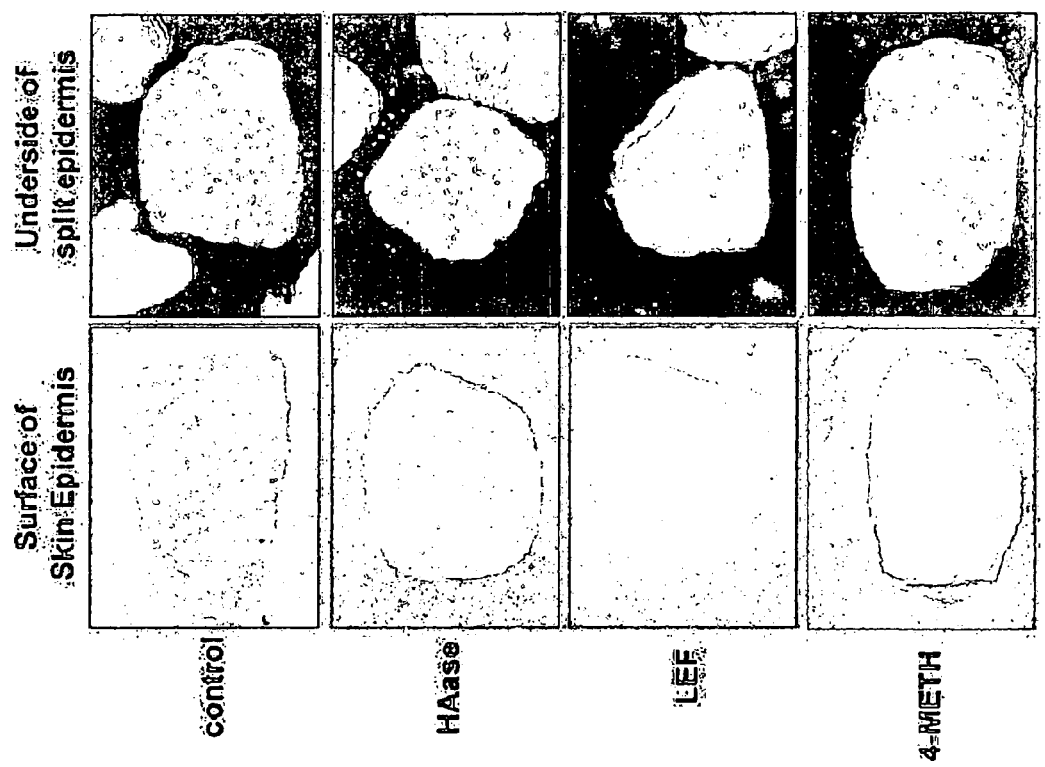
FIG. 21 represents light microscopy images depicting the surface or underside of enzymatically separated skins obtained from embryonic skin cultured for 72 hrs in the presence of BSA (control), hyaluronanase (HAase), or one of two HAS inhibitors, leflunomide (Lef) or 4-methylumbelliferone. Visible follicles would be located on the surface of the skin (left column). Developing epidermal hair germs would be located on the underside of the skin (right column).

The effects of HA synthesis downregulation of hair follicle morphogenesis was investigated. Embryonic skin was cultured for 72 hrs in the presence of BSA (control) or one of two HAS inhibitors, leflunomide (Lef) (50 nM) or 4-methylumbelliferone (30 mM). In the presence of BSA, CD44 was localized predominantly to the dermal condensate, while HA remained absent from the dermal condensate (FIG. 20). Thus, BSA did not alter protein expression nor did it disrupt cellular mechanisms (such as CD44 mediated HA uptake). Visualization of the surface of 4-methylumbelliferone-treated skins (n=6) revealed no effect on the number of visible follicles. Lef treatment, however, resulted in a reduction in the number of visible follicle on the surface of the skin (FIG. 21) (n=6). To ascertain whether this reduction was due to an actual inhibitory effect of Lef on hair follicle morphogenesis and development, cultured skin from all treatments and control groups were enzymatically split and the separated epidermis inverted to allow the visualization of the developing epidermal hair germs. The epidermal germs of the Lef-treated cultures were clearly visible, however they appeared smaller and sparser than those of the control or the 4-methylumbelliferone-treated skin cultures (FIG. 21).

To explore the effects of a global degradation of HA protein on hair follicle morphogenesis within the skin cultures, embryonic skin was cultured for 72 hrs in the presence of either BSA (control) or hyaluronanase (HAase) (25 units/ml). As with the Lef-treated skin cultures, the number of epidermal germs could be distinguished on the skin surface and their numbers appeared reduced. Interestingly, separation of the epidermis and dermis as above revealed that HAase treatment had little or no effect on the size or number of epidermal hair germs, indicating that the lack of visible follicle on the skin surface may have been due to an effect other than that of hair follicle inhibition (i.e. epidermal thickening) (FIG. 21).

Characterization of the Effects of HAS Inhibition and HASase Treatment

Figure 22:
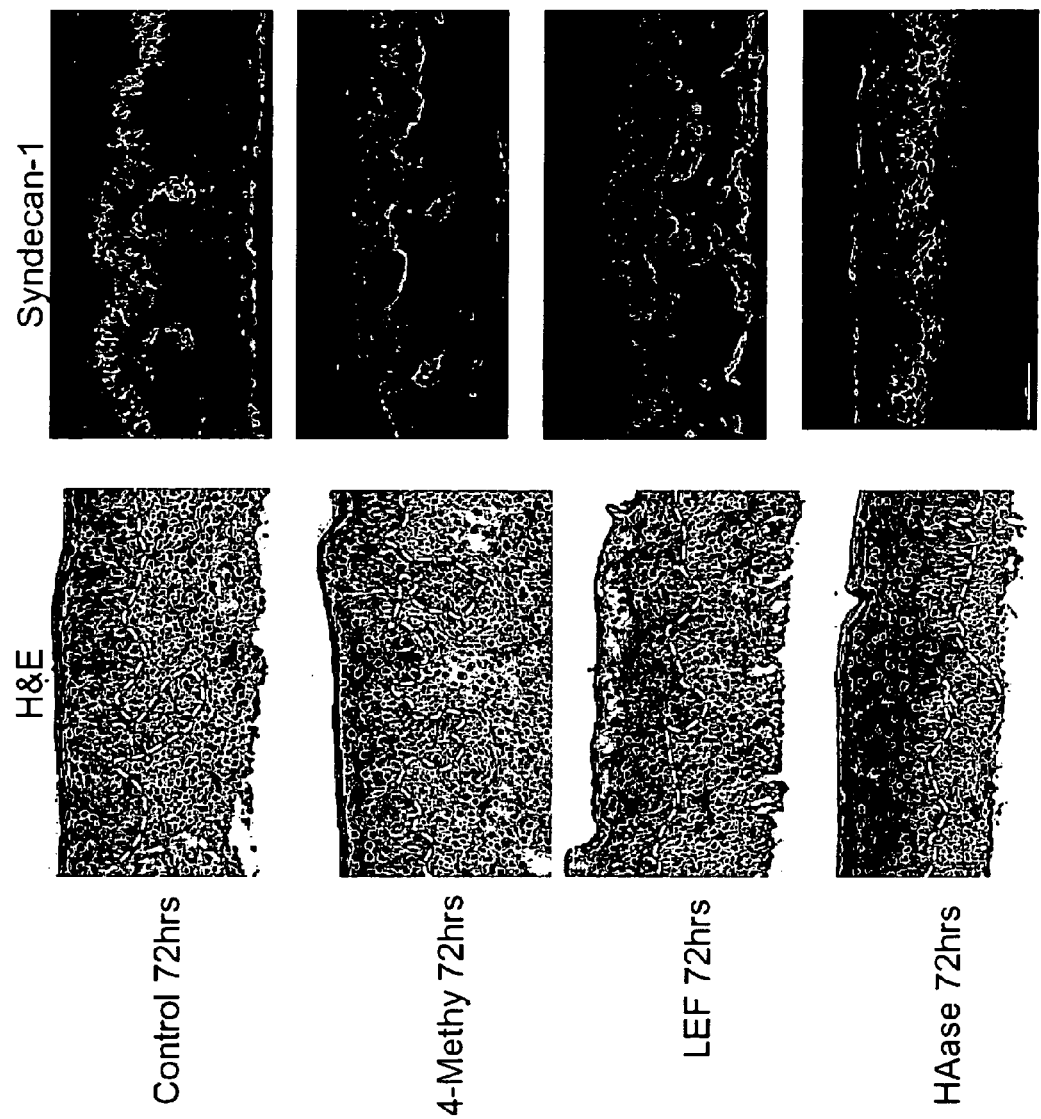
FIG. 22 represents light and immunofluorescent microscopy images depicting the surface or underside of enzymatically separated skins obtained from embryonic skin cultured for 72 hrs in the presence of BSA (control), hyaluronanase (HAase), or one of two HAS inhibitors, leflunomide (Lef) or 4-methylumbelliferone. Hematoxylin and eosin (H&E) staining is found in the left column), Syndecan-1 (red; marker of dermal condensation) localization is depicted in the right column. Laminin (green; marker for Basement Membrane); DAPI (Blue; depicts nuclei staining).

Following 72 hrs in culture, embryonic skin from the four treatments described above were cryo-embedded, sectioned, and stained with hematoxylin and eosin (H&E) for histological study. Skin cultured in the presence of 4-methylumbelliferone once again appeared indistinguishable from the control skin, corresponding to 16.5 dpc in vivo backskin (FIG. 22). Further characterization using antibodies specific for Syndecan-1, a marker of the dermal condensation, revealed normal hair follicle development. H&E staining along with syndecan-1 expression analysis of the Lef-treated skins revealed that an inhibition of HAS1 inhibition resulted in the inhibition of follicle development (FIG. 22). After 72 hr in culture, follicles corresponded to those found in 14.5 dpc skin in vivo, both histologically and in their syndecan-1 expression patterns (FIG. 22).

HAase treatment resulted in the formation of a dense dermis, making it difficult to distinguish the dermal condensation from the surrounding interfollicular dermis. However, syndecan-1 expression remained localized, suggesting that the dermal condensation had formed and remained as a discreet biological unit (FIG. 22).

Example 10

Alginate Microencapsulated Human DP Aggregates Implanted into the Epithelium of a Footpad Preparing Cells to Make Aggregates.

DP cells were isolated from rat whiskers and were cultured up through 3-5 passages. DP cells were first washed while in their T25 flask and subsequently trypsinized within the flask. Media containing 10% FBS was added to the cells to stop trypsinisation and were then centrifuged at 1000 rpm for 5 minutes. After the excess media was poured off, the pellet of cells was washed with serum free/antibiotic free media in order to remove any remaining trypsin and was centrifuged at 1000 rpm for 5 minutes. After the excess media was poured off, the pellet of cells was resuspended in 1 ml of dMEM media containing 10% FBS. Cells were counted using a haemocytometer to count cells. Cells were diluted to 300 cells/µl by adding dMEM media containing 10% FBS.

Alginate Matrix and Aggregate Formation.

Alginate, which is extracted from the cell walls of brown seaweed, is a type of hydrogel that forms linear co-polymers of 1,4-linked D-mannuronic acid (M), L-guluronic acid (G). The alginate bead can comprise a semi-permeable membrane and its gel properties allow for diffusion of biologically active species both into and out of the beads (such as nutrients, $CO_2$ and $O_2$). Thus, the bead ensures cell viability and can allow for secretion of therapeutic molecules as well as the proper excretion of waste molecules. While allowing for fast diffusion, alginate gels maintain the proper mechanical strength and stability to house cells, such as DP cells, DS cells, and the like. The gel in alginate beads enable cells to be suspended within thus can create a three-dimensional micro-environment.

Figure 23:
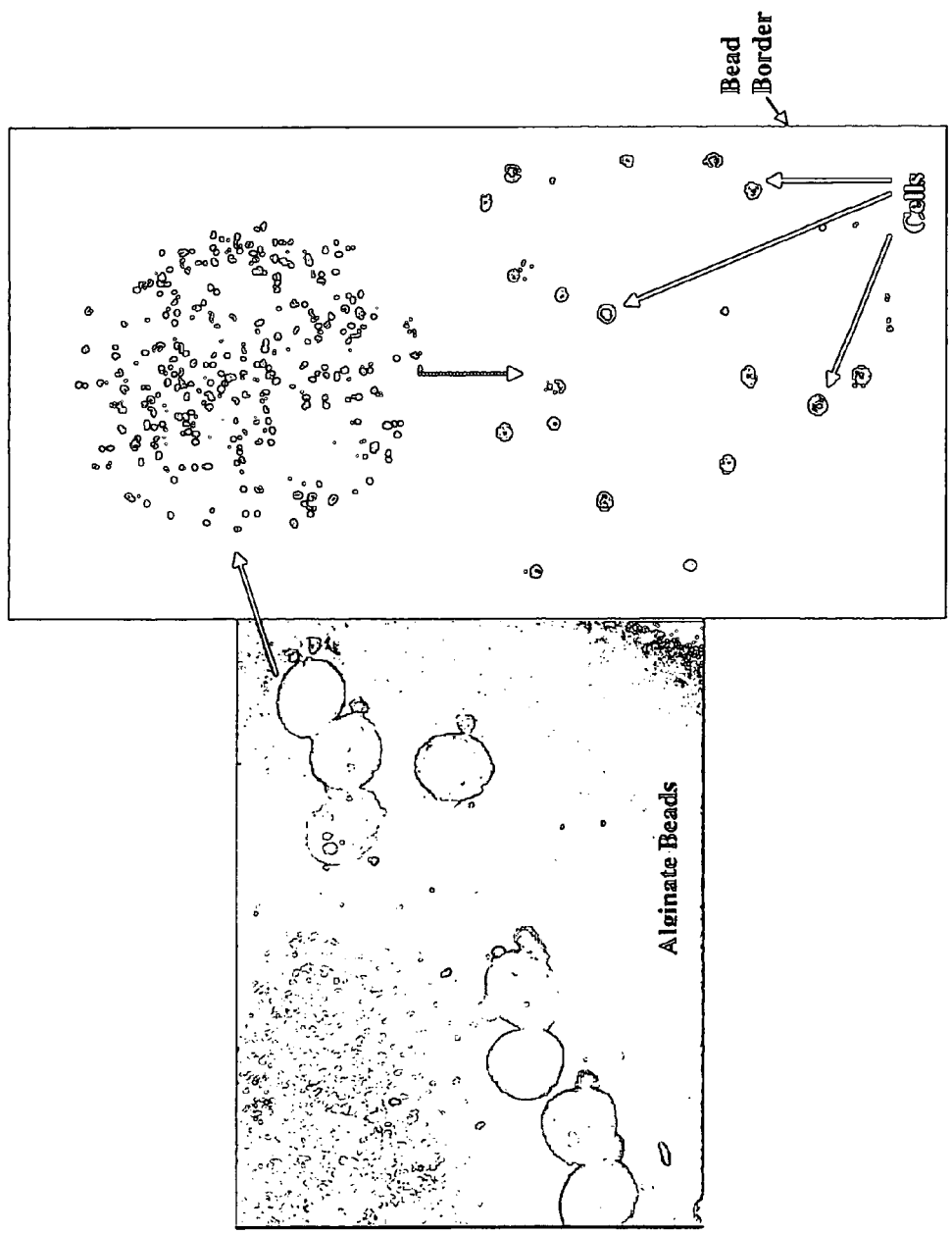
FIG. 23 is a schematic of alginate beads used to microencapsulate DP cells.

DP cells were microencapsulated in alginate beads via using a 22 g needle. Approximately 3000 cells were introduced into a bead (See FIG. 23). The alginate beads were incubated at 37° C. for 30 hours. This method can also be carried out to generate aggregates of dermal sheath cells.

Viability Cytotoxicity Assay.

Cell survival and viability of DP cells encapsulated in the beads during in vitro culturing was examined according to the manufacturer's directions at days 0, 2, 4, 10, and 42 using 2 probes, calcein AM and ethidium homodimer-1 from Molecular Probes (Catalog #L3224; Invitrogen Corp., CA) that can be visualized using standard confocal microscopy imaging techniques (Molecular Probes, *The Handbook: A Guide to Fluorescent Probes and Labelling Technologies*, 10th edition (Invitrogen Corp., CA). Even after 10 days culture while encapsulated in alginate beads, DP cells maintained viability comparable to that of initial culturing on Day 0 (viable cells depicted as green images, dead cells depicted as red images; FIG. 24).

Footpad Epithelium.

Figure 25:
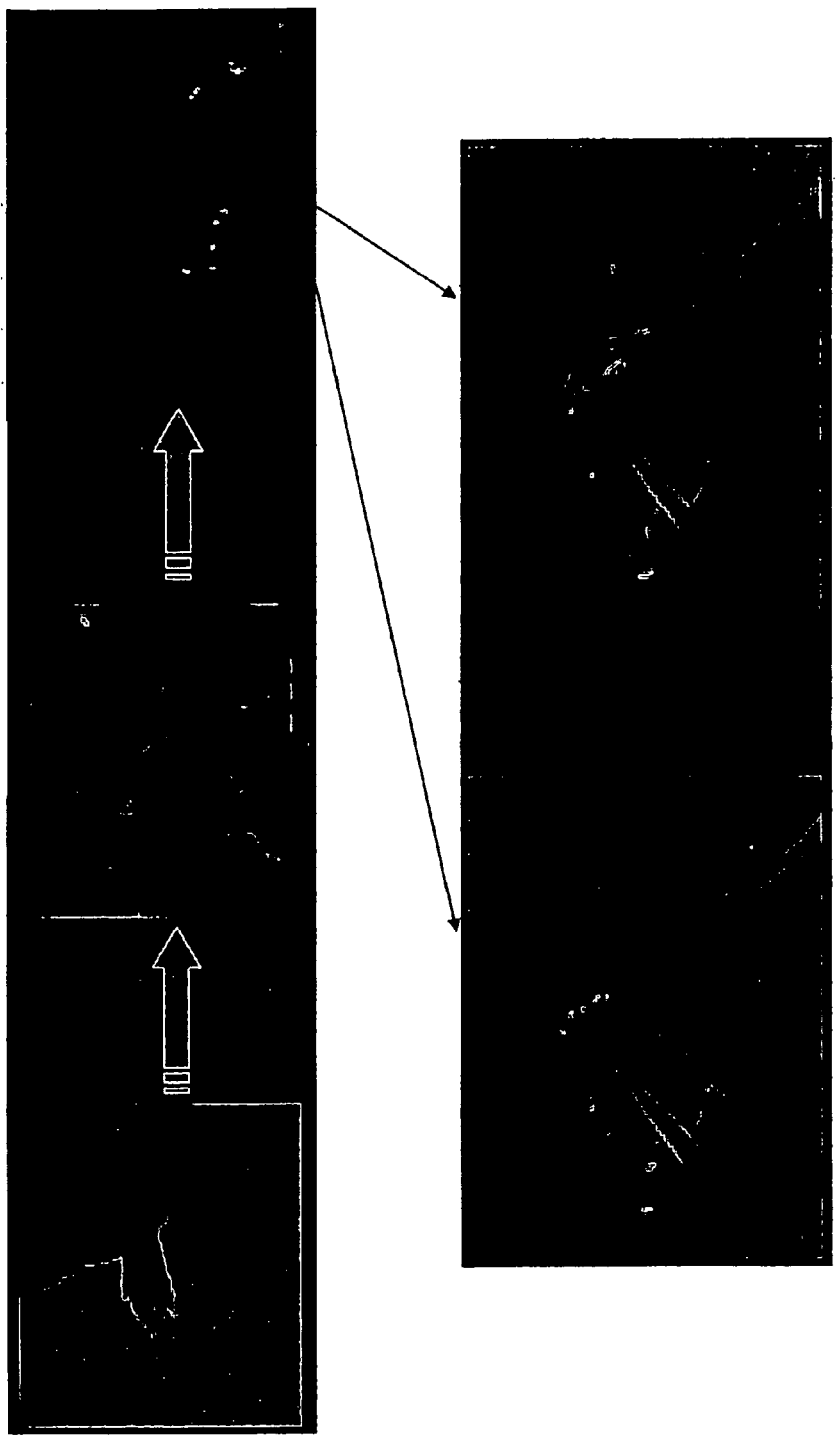
FIG. 25 is a photographic representation of human DP aggregates microencapsulated by alginate beads that were inserted into an enzymatically separated foot-pad skin sample.
Figure 26:
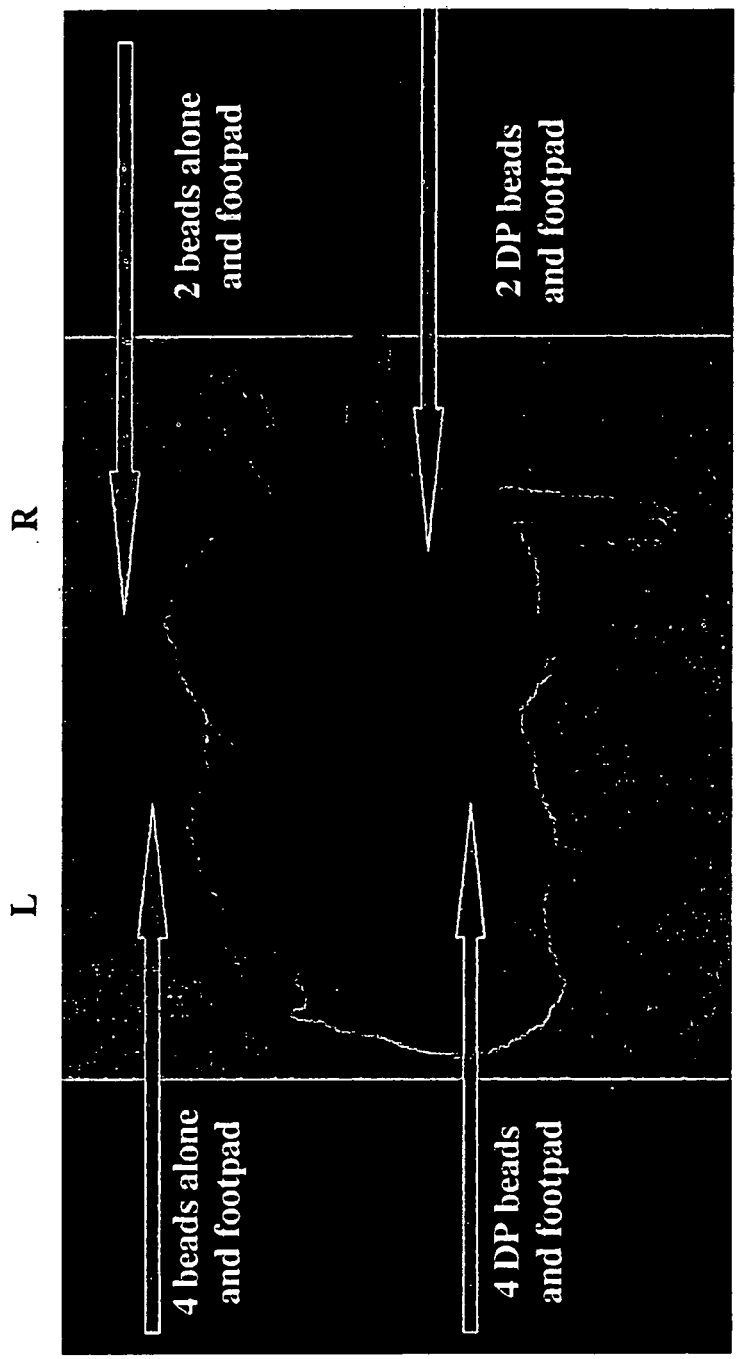
FIG. 26 is a photographic representation of human DP aggregates microencapsulated by alginate beads that were implanted according to the scheme laid out in the image into a mouse model.

The footpad epidermis and dermis was separated over half the skin using pancreatin and tryspin in Earles MEM medium. This was placed on Gey's agar with the epidermis folded back on itself. Alginate-encapsulated DP beads were subsequently removed from culture and placed in a drop of MEM medium. Alginate-encapsulated DP beads were picked up one at a time with forceps and placed onto the dermis. Two to four alginate-encapsulated DP beads were placed on each skin bit. The epidermis was then folded back to sandwich the alginate-encapsulated DP beads and were subsequently incubated 37° C. for 2 hours. The DP balls were then placed under the kidney capsule of nude mice (see schematics depicted in FIG. 25 and FIG. 26), were removed and photographed, and subsequently sectioned for microscopy analysis (such as H&E staining (Cat# SS007: Biogenex, San Ramon, Calif.); immunohistochemistry such as DAB staining (Molecular Probes, *The Handbook: A Guide to Fluorescent Probes and Labelling Technologies*, 10th edition (Invitrogen Corp., CA); and immunofluorescence microscopy (Molecular Probes, *The Handbook: A Guide to Fluorescent Probes and Labelling Technologies*, 10th edition (Invitrogen Corp., CA)).

Results.

Figure 27:
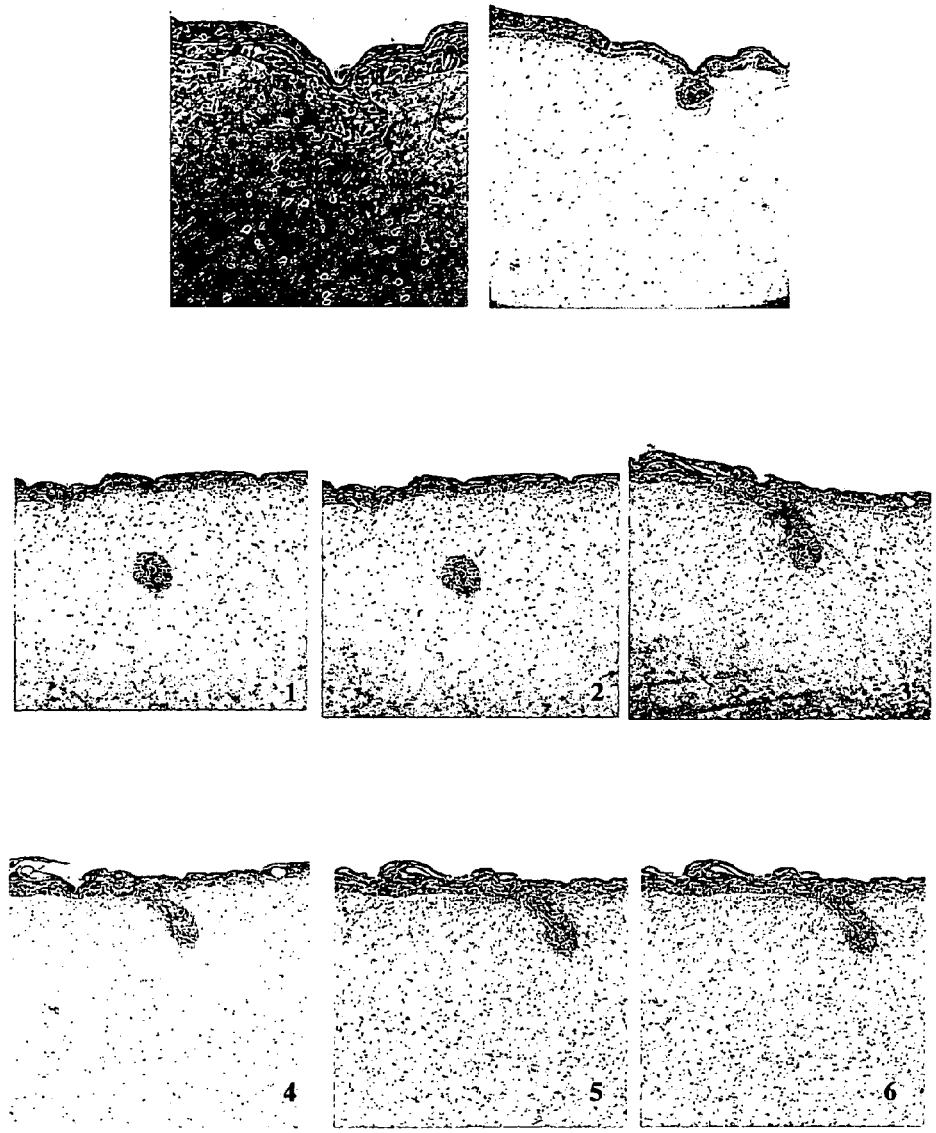
FIG. 27 represents light microscopy images of hematoxylin and eosin (H&E) serial stained sections of murine epidermis obtained from human DP aggregates microencapsulated by alginate beads that were inserted into an enzymatically separated foot-pad skin sample, which depicts hair follicle induction (panels 1-6). The top 2 panels depict H&E staining of hair follicle.

The alginate-encapsulated DP beads used in this method were deemed "too big" in that the alginate-encapsulated DP beads did not "fit" in the footpad. In several instances, the alginate-encapsulated DP beads dislodged from the footpad epithelium and failed to remain within the implantation site. Despite that obstacle, preliminary results show some evidence of hair follicle induction (FIG. 27, panels 1-6). DP cells appear to have maintained their hair inductive activity within the alginate-encapsulated DP beads in the absence of stimulation and/or signals arising from epithelial cells (FIG. 27). Thus, using a smaller alginate bead size to encapsulate DP cells would more than likely enhance induction of hair follicles.

What is claimed:

1. A method for maintaining hair inductive activity of dermal papilla cells or dermal sheath cells or a combination thereof, the method comprising: growing dermal papilla cells or dermal sheath cells or a combination thereof in suspension culture so as to obtain a compact aggregate of cells, wherein the suspension culture is a hanging drop culture.

2. The method of claim 1, further comprising: admixing with the suspension culture an effective amount of a substance capable of reducing the amount of extracellular matrix in the suspension culture.

3. The method of claim 1 or 2, wherein the suspension culture comprises a soluble factor.

4. The method of claim 3, wherein the soluble factor is added exogenously.

5. The method of claim 3, wherein the soluble factor is administered in an amount of from about 5 ng/ml of culture media to about 300 ng/ml of culture media.

6. The method of claim 3, wherein the soluble factor comprises periostin, follistatin, Wise, Wnt10b, any one or more soluble factors in Table 1 and Table 2, or any combination thereof.

7. The method of claim 2, wherein the substance is a protein.

8. The method of claim 7, wherein the protein is an enzyme.

9. The method of claim 8, wherein a substrate of the enzyme is an extracellular matrix molecule in the suspension culture.

10. The method of claim 8, wherein the enzyme is a hyaluronidase, a collagenase, a chondroitinase, or a combination thereof.

11. The method of claim 10, wherein the hyaluronidase is admixed with the suspension culture in an amount of from about 20 U/ml of culture media to about 50 U/ml of culture media for up to about 15 days.

12. The method of claim 10, wherein the hyaluronidase is Hyal-1, Hyal-2, Hyal-3, or a combination thereof.

13. The method of claim 7, wherein the protein degrades one or more molecules in the extracellular matrix.

14. The method of claim 1, wherein the hanging drop culture contains less than about 9,000 cells.

15. The method of claim 1, wherein the hanging drop culture contains less than about 7,000 cells.

16. The method of claim 1, wherein the hanging drop culture contains less than about 5,000 cells.

17. The method of claim 1, wherein the hanging drop culture contains less than about 3,000 cells.

18. The method of claim 1, wherein the suspension culture further comprises epithelial cells.

19. The method of claim 18, wherein the epithelial cells are derived from hair follicle or skin.

20. The method of claim 18, wherein the epithelial cell is a keratinocyte.

21. The method of claim 1, wherein the hanging drop is cultured for at least 24 hours.

22. The method of claim 1, wherein the hanging drop is cultured for at least 48 hours.

23. The method of claim 1, wherein the hanging drop is cultured up to about 3, 4, 5, 6, 7, 8, 9, 10, 11, 12, 13, 14, or 15 days.

24. The method of claim 1, wherein the hanging drop is cultured until expression of an inductivity marker gene is reduced.

25. The method of claim 24, wherein the inductivity marker gene comprises Wnt10b, WISE, versican, or a combination thereof.

26. The method of claim 1 or 2, further comprising grafting the compact aggregate of cells into the skin of a subject.

27. The method of claim 26, wherein the subject is a mammal.

28. The method of claim 27, wherein the mammal is a human, a mouse, a dog, a cat, a horse, a cow, or a bird.

29. The method of claim 26, wherein the cells are autologous to the subject.

30. The method of claim 1 or 2, wherein the cells comprise primary cells, secondary cells, passaged secondary cells, or a cell line.

31. The method of claim 30, wherein the cells are obtained or derived from a mammal.

32. The method of claim 31, wherein the mammal is a human, a mouse, a dog, a cat, a horse, or a cow.

33. The method of claim 1, further comprising promoting formation of hair follicles from the aggregated dermal papilla cells or dermal sheath cells or a combination thereof, the method comprising: admixing hyaluronidase with the culture for a time of from about 1 day to about 15 days; and growing the culture for a sufficient time so as form hair follicles.

34. The method of claim 33, wherein the suspension culture comprises a soluble factor.

35. The method of claim 34, wherein the soluble factor is added to the growing suspension culture.

36. The method of claim 34, wherein the soluble factor is admixed to the suspension culture in an amount of from about 5 ng/ml of culture media to about 300 ng/ml of culture media.

37. The method of claim 34, wherein the soluble factor comprises periostin, follistatin, Wise, Wnt10b, any one or more soluble factors in Table 1 and Table 2, or any combination thereof.

38. The method of claim 33, wherein the hanging drop culture contains less than about 9,000 cells.

39. The method of claim 33, wherein the hanging drop culture contains less than about 7,000 cells.

40. The method of claim 33, wherein the hanging drop culture contains less than about 5,000 cells.

41. The method of claim 33, wherein the hanging drop culture contains less than about 3,000 cells.

42. The method of claim 33, wherein the suspension culture further comprises epithelial cells.

43. The method of claim 42, wherein the epithelial cells are derived from a hair follicle or skin.

44. The method of claim 42, wherein the epithelial cell is a keratinocyte.

45. The method of claim 33, wherein the hyaluronidase is admixed in an amount of from about 20 U/ml of culture media to about 50 U/ml of culture media.

46. The method of claim 33, wherein the hyaluronidase is Hyal-1, Hyal-2, Hyal-3, or a combination thereof.

47. The method of claim 33, wherein the suspension culture is grown for at least 24 hours.

48. The method of claim 33, wherein the suspension culture is cultured until expression of an inductivity marker gene is reduced.

49. The method of claim 48, wherein the inductivity marker gene comprises Wnt10b, WISE, versican, or a combination thereof.

50. The method of claim 33, further comprising grafting the hair follicles into the skin of a subject.

51. The method of claim 50, wherein the subject is a mammal.

52. The method of claim 50, wherein the cells are autologous to the subject.

53. The method of claim 51, wherein the mammal is a human, mouse, dog, or cat.

54. The method of claim 33, wherein the cells comprise primary cells, secondary cells, passaged secondary cells, or a cell line.

55. The method of claim 54, wherein the cells are from a mammal.

56. The method of claim 55, wherein the mammal is a human, a mouse, a dog, a cat, a horse, or a cow.

* * * * *